United States Patent
Quay et al.

(10) Patent No.: US 7,186,692 B2
(45) Date of Patent: *Mar. 6, 2007

(54) COMPOSITIONS AND METHODS FOR ENHANCED MUCOSAL DELIVERY AND NON-INFUSED ADMINISTRATION OF Y2 RECEPTOR-BINDING PEPTIDES AND METHODS FOR TREATING AND PREVENTING OBESITY

(75) Inventors: Steven C. Quay, Edmonds, WA (US); Gordon Brandt, Issaquah, WA (US)

(73) Assignee: Nastech Pharmaceutical Company Inc., Bothell, WA (US)

( * ) Notice: Subject to any disclaimer, the term of this patent is extended or adjusted under 35 U.S.C. 154(b) by 233 days.

This patent is subject to a terminal disclaimer.

(21) Appl. No.: 10/869,649

(22) Filed: Jun. 16, 2004

(65) Prior Publication Data

US 2005/0002927 A1 Jan. 6, 2005

Related U.S. Application Data

(63) Continuation-in-part of application No. 10/745,069, filed on Dec. 23, 2003, which is a continuation-in-part of application No. 10/322,266, filed on Dec. 17, 2002.

(60) Provisional application No. 60/518,812, filed on Nov. 10, 2003, provisional application No. 60/517,290, filed on Nov. 4, 2003, provisional application No. 60/510,785, filed on Oct. 10, 2003, provisional application No. 60/501,170, filed on Sep. 8, 2003, provisional application No. 60/493,226, filed on Aug. 7, 2003.

(51) Int. Cl.
- A61K 38/17 (2006.01)
- A61K 38/28 (2006.01)
- C07K 14/435 (2006.01)

(52) U.S. Cl. .................... 514/12; 530/324; 530/303

(58) Field of Classification Search .............. 514/12; 530/324, 303

See application file for complete search history.

(56) References Cited

U.S. PATENT DOCUMENTS 5,308,620 A 5/1994 Yen
5,574,010 A 11/1996 McFadden (Continued)

FOREIGN PATENT DOCUMENTS

EP 1 288 223 A1 3/2003

(Continued)

OTHER PUBLICATIONS

Batterham et al., "Gut hormone PYY(3-36) physiologically inhibits food intake," Nature 418:650-654, 2002.*

(Continued)

Primary Examiner—Jon Weber
Assistant Examiner—Rosanne Kosson
(74) Attorney, Agent, or Firm—Peter J. Knudsen

(57) ABSTRACT

Pharmaceutical compositions and methods are described comprising at least one Y2 receptor-binding peptide, such as peptide YY(PYY), Neuropeptide Y (NPY) or Pancreatic Peptide (PP) and one or more mucosal delivery-enhancing agents for enhanced nasal mucosal delivery of the peptide YY, for treating a variety of diseases and conditions in mammalian subjects, including obesity.

50 Claims, 14 Drawing Sheets

U.S. PATENT DOCUMENTS

| | | | |
|---|---|---|---|
| 5,604,203 | A | 2/1997 | Balasubramaniam |
| 5,616,311 | A | 4/1997 | Yen |
| 5,696,093 | A | 12/1997 | Tseng |
| 5,716,643 | A | 2/1998 | Yen |
| 5,725,804 | A | 3/1998 | Yen |
| 5,759,656 | A | 6/1998 | Collette |
| 5,912,227 | A | 6/1999 | Croom, Jr. et al. |
| 5,945,033 | A | 8/1999 | Yen |
| 5,968,748 | A | 10/1999 | Bennett et al. |
| 5,977,175 | A | 11/1999 | Lin |
| 5,980,945 | A | 11/1999 | Ruiz |
| 6,013,285 | A | 1/2000 | Yen |
| 6,013,633 | A | 1/2000 | Balasubramanium |
| 6,017,879 | A | 1/2000 | Mutter et al. |
| 6,046,167 | A | 4/2000 | Balasubramaniam |
| 6,191,102 | B1 | 2/2001 | DiMarchi et al. |
| 6,235,718 | B1 | 5/2001 | Balasubramanium et al. |
| 6,264,988 | B1 | 7/2001 | Yen |
| 6,391,343 | B1 | 5/2002 | Yen |
| 6,558,708 | B1 | 5/2003 | Lin |
| 6,583,111 | B1 | 6/2003 | DiMarchi et al. |
| 6,737,408 | B1 | 5/2004 | Balasubramanium et al. |
| 2004/0228846 | A1* | 11/2004 | Pang et al. ............... 424/93.7 |
| 2005/0176630 | A1* | 8/2005 | Cowley et al. ............. 514/12 |

FOREIGN PATENT DOCUMENTS

| | | |
|---|---|---|
| EP | 1 288 224 A1 | 3/2003 |
| EP | 0 678 018 B1 | 4/2003 |
| EP | 1 051 194 B1 | 5/2003 |
| EP | 1 466 610 A1 | 10/2004 |
| WO | WO 94/22467 A1 | 10/1994 |
| WO | WO 96/20885 A1 | 5/1998 |
| WO | WO 99/02135 A1 | 1/1999 |
| WO | WO 09915516 A1 | 4/1999 |
| WO | WO 00/47219 A2 | 8/2000 |
| WO | WO 02/47712 A2 | 6/2002 |
| WO | WO 03/026591 A2 | 4/2003 |
| WO | WO 03/057235 A2 | 7/2003 |
| WO | WO 03/105763 A2 | 12/2003 |

OTHER PUBLICATIONS

Mei-Huei Chen; Balasubramanian; Murphy; Tabata; Fischer; Chen; Joffe, Sensitive Radioimmunoassay for Measurement of Ci'rculating Peptide YY, Gastroenterology, 1984, pp. 1332-1338, vol. 87, Publisher: American Gastroenterological Association, Published in: Cincinnati, Ohio.

Morley, John E.; Levine, Allen S.; Grace, Martha; Kneip, Julie, "Peptide YY (PYY), a potent orexigenic agent," Brain Research, 1985, vol. 341, pp. 200-203. Elsevier Science Publishers.

John E. Morley and James F. Flood, An Investigation of Tolerance to the actions of Leptogenic and Anorexigenic Drugs in Mice, Life Sciences, Sep. 10, 1987, pp. 22157-22165, vol. 41, Publisher: Pergamon Journals, Published in: Sepulveda, CA, US.

Kazuhiko Tatemoto; Nakano; Makk; Angwin; Mann; Schilling; Go, Isolation and Primary Structure of Human Peptide YY Biochemical and Biophysical Research Communications, Oct. 31, 1988, pp. 713-717, vol. 157(2), Publisher: Academic Press, Inc., Published in: Los Angeles, California, US.

Balasubramaniam, A.; Servin, A. L.; Rigel, D. F.; Rouyer-Fessard, C. R.; Laburthe, M. Syntheses and receptor affinities of partial sequences of peptide YY (PYY) Peptide.Research. date- 1988, vol. 1, No. 1, pp. 32-35.

John E. Morley, An approach to the development of drugs for appetite disorders, Neuropsychobiology, Date 1989, vol. 21, issue 1, pp. 22-30, Karger AG, Basel.

Eberlein, G. A.;Eysselein, V. E.;Schaeffer, M.; Layer, P.;Grandt, D.;Goebell, H.;Niebel, W.;Davis, M.;Lee, T. D.; Shively, J. E.; Reeve, J. R., Jr.; A new molecular form of PYY: structural characterization of human PYY(3-36) and PYY(1-36) Peptides, DATE-1989, vol. 10, No. 4, pp. 797-803, Pergamon Press, US.

Eysselein V. E.;Eberlein, G. A.;Grandt, D.;Schaeffer, M.;Zehres, B.; Behn, U.;Schaeffer, D.;Goebell, H.;Davis, M.; Lee,T. D.; Shively, J. E.; Meyer, H. E.; Reeve, J. R., Jr, Structural characterization of canine PYY, Peptides, Jun. 15, 1989, vol. 11 pp. 111-116, Pergamon Press, US.

Hiroyuki Minakata, Takashi Iwashita, Synthesis of analogues of peptide YY with modified N-terminal regions: relationships of amphipihlic secondary structures and activity in rat vas deferens, Journal: Biopolymers, vol. 29, Jan. 29, 1990, pp. 61-67, John Wiley & Sons, Inc.

Ramo, O. J.; Balasubramaniam, A.; Sheriff, S.; Rogers, D. H.; McCullough, P. J.;Bell, R. H., Jr., Neuropeptide Y and peptide YY stimulate the growth of exocrine pancreatic carcinoma cells, Neuropeptides, 1990, vol. 15, pp. 101-106, Longman Group UK.

S.F. Leibowitz, J.T. Alexander, Analysis of Neuropeptide Y-Induced Feeding: Dissociation of Y1 and Y2 Receptor Effects on Natural Meal Patterns, Peptides, Jul. 25, 1991, pp. 1251-1260, vol. 12, Publisher: Pergamon Press, Published in: New York, NY, US.

Marc Laburthe, Peptide YY et neuropeptide Y dans L'intesin: disponibilite, effets biologiques et recepteurs epitheliaux, [translated title: Peptide YY and neutopeptide Y in the intestine: availability, biologic effects and epithelial receptors] Arch Int. Physiol Biochim Biophys, Reunion Complementaire de Physiologie, Association des Physiologistes, Toulouse 26-27, Apr. 1991, France.

Inui Akio, Minoru Okita, Masaharu Nakajima, Toru Inoue, Noriaki Sakatani, Manabu Oya, Hideki Morioka, Yasuhiko Okimura, Kazuo Chihara, and Shigeaki Baba, Neuropeptide regulation of feeing in dogs, Neuropeptides and Food Intake, 1991, pp. R5888-R594, 0363-6119, The Amerian Physiologial Society.

Grandt, D.; Teyssen, S.; Schimiczek, M.; Reeve, J. R., Jr.; Feth, F.; Rascher, W.; Hirche, H.; Singer, M. V.; Layer, P.; Goebell, H.; Ho, F.J.; Eysselein, V.E.: Novel generation of hormone receptor specificity by amino terminal processing of peptide YY, Biochemical and Biophysical Research Communications, Aug. 14, 1992, vol. 186, No. 3, pp. 1299-1306, Academic Press, Inc.

S. Okada, Ohshima, Mori, K. Tatemoto, Peripherally not Centrally Administered Peptide YY(PYY) Decreases High Fat Diet Intake, Jun. 9, 1993, vol. 520, Publisher: Endocrinology, Published in: Gunmo, Japan.

Grandt, D.; Schimiczek, M.; Struk, K.; Shively, J.; Eysselein, V. E.; Goebell, H.; Reeve, J. R., Jr—Characterization of two forms of peptide YY, PYY(1-36) and PYY(93-36), in the rabbit, Peptides, Jul. 29, 1994, vol. 15, No. 5, pp. 815-820, Pergamon, Elsevier Science Ltd, US.

Dumont, Yvan.; Cadieux, Alain.; Pheng, L. H.; Fournier, A.; St Pierre, S.; Quirion, R., Peptide YY derivatives as selective neuropeptide Y/peptide YY $Y^1$ and $Y^2$ agonists devoided of activity for the $Y^3$ receptor sub-type, Brain Research.Molecular.Brain Research, —Jun. 28, 1994, vol. 26, No. 1-2, pp. 320-324, Elsevier Science B.V.

Wlodarczyk-Bisaga K.; Bisaga A., Biologiczne aspekty zaburzeń odżywiania się—wybrane zagadnienia [Selected issues of biological aspects of eating disorders], Psychiatria Polska, Sep.-Oct. 1994; vol. 28, No. 5: pp. 579-591. Poland.

Margaret Dos Santos Medeiros, M. D.; Anthony J. Turner, Processing and metabolism of peptide-YY: pivotal roles of dipeptidylpeptidase-IV, aminopeptidase-P, and endopeptidase-24. 11, Endocrinology 1994, Vo 134, No. 5, pp. 2088-2094, the Endocrine Society, US.

Grandt, D.; Schimiczek, M.; Beglinger, C.; Layer, P.; Goebell, H.; Eysselein, V. E.; Reeve, J. R., Jr, Two molecular forms of peptide YY (PYY) are abundant in human blood: characterization of a radioimmunoassay recognizing PYY 1-36 and PYY 3-36, Regulatory Peptides, May 5, 1994, vol. 51, No. 2, pp. 151-159, Elsevier Sciences B.V.

Kazuhiko Tatemono, New Developments in Research on digestive tract hormones, Progress in Medicine, vol. 15, No. 9, date Sep. 1995, pp. 1793-1804, 46th Pepsin Research Meeting (translated from Japanese) JP.

Norio Tani, Digestive Tract Hormones, Digestive Tract, 1996, Article Ser. No. 0012 (translated from Japanese) JP.

Gue, M.; Junien, J. L.; Reeve, J. R., Jr.; Rivier, J.; Grandt, D.; Tache, Y, Reversal by NPY, PYY and 3-36 molecular forms of NPY and PYY of Intracisternal CRF-induced inhibition of gastric acid secretion in rats, British Journal of Pharmacology, May 1996, pp. 118(2), 237-242, Stockton Press.

Rachel L. Batterham, Michael A. Cowley, Caroline S. Small, Herbert Herzog, Mark A. Cohen, Catherine L. Dakin, Alison M. Wren, Audrey E. Brynes, Malcom J. Low, Mohammad A. Ghatei, Roger D. Cone, Stephen R. Bloom. "Gut hormone PYY3-36 physiologically inhibits food intake," Nature, 2002, vol. 418, pp. 650-654, Nature Publishing Group.

Herbert Herzog, Hypothalamic Y2 Receptors: Central Coordination of Energy Homeostasis and Bone Mass Regulation, Drug News Perspect. Oct. 2002, pp. 506-510, vol. 15 (8), Prous Science.

Batterham, Rachel, L.; Cohen, Mark. A.; Ellis, Sandra. M.; Le Roux, Carel. W.; Withers, Dominic. J.; Frost, Gary. S.; Ghatei, M. A.; Bloom. S. R., Inhibition of food intake in obese subjects by peptide YY3-36, The New.England.Journal of Medicine, DATE-Sep 4, 2003, pp. 941-948, vol. 349.

Rachel L. Batterham, Stephen R. Bloom,. The gut hormone peptide YY regulates appetite , N.Y.Academy.of Sciences, 2003, pp. 162-168, vol. 994.

R. L. Batterham, C.W. Le Roux, M.A. Choen, A.J. Park, S.M. Ellis, M. Patterson, G.S. Frost, M.A.Ghatei and S.R. Bloom, Pancreatic polypeptide reduces appetite and food intake in humans, The Journal of Clincal Endocrinology and Metobolism, 2003, pp. 3989-3992, vol. 88(8), the Endocrine Society, US.

Von E. Niebergall-Roth, S. Teyssen K. Rippel Und M.V. Singer, Die wirkungen von peptide yy auf funktionen des gastrointestinaltrakies, Dtsch. Tierarztl, Wschr 104, pp. 85-124, Heft, 3, Mar. 1997, National Library of Medicine (article in German).

Kazuhiko Tatemoto, Chemical and clinical Applications of Digestive Tract hormones, Digestive Tract hormones, 1994, pp. 38-45, vol. 2, No. 4, G. I. Research (translated Japanese article) JP.

Chen, C. H.; Stephens, R. L. Jr.; Rogers, R. C., PYY and NPY: control of gastric motility via action on Y1 and Y2 receptors in the DVC, Neurogastroenlarol.Motil. 1997, pp. 109-116, vol. 9, Blackwell Science Ltd., US.

Xiao, Q.; Han, X.; Arany, E.; Hill, D.; Challis, J. R.; McDonald, T. J. Human placenta and fetal membranes contain peptide YY1-36 and peptide YY3-36, Journal of Enocrinology, 1998, pp. 485-492, vol. 156, Journal of Endiocrinology Ltd, UK.

Naruto Yamawaki, Yasuaki Okamoto, Is there a biological case for eating disorders? From the perspective of neurochemistry, Brian Science, 1998, pp. 29-38, Article Ser. No. 0003, vol. 20, Special Ediiton (Eating Disorders and Obesity) Think also presented at conference Apr. 24, 1998 at Showa University, Yokohama, Japan (translated Japanese artilce) JP.

Noboru Yanaihara, VIP, PYY and Others, All About Hormone Illustrated No. 381, 1998, pp. 382-387, Article Ser. No. 0033, vol. 46, VI. Gastrointestinal Hormones, (translated Japanese article) JP.

Kazuhiko Tatemoto, Development of Neuropeptide Y Receptor Antagonists, Research on Biologically Active Substances, Research Papers of the Suzuken Memorial Foundation, vol. 14, pp. 243-244 (translated Japanese article) JP, publication date not available.

David A. Keire, Mitsuo Kobayashi, Travis E. Solomon, Joseph R. Reeve, Jr., Solution structure of monomeric peptide YY supports the functional significance of the PP-Fold, Biochemistry 2000, pp. 9935-9942, Nov. 8, 1999, American Chemical Society, published on web Jul. 21, 2000, US.

Philippe Naveilhan, Hessameh Hassani, Josep M. Canals, A. Jonas Ekstrand, ASA Larefalk, Vijay Chhajlani Ernest Arenas, Karin Gedda, Lennart Svensson, Peter Thoren, and Patrik Ernfors, Normal feeding behavior, body weight and leptin response require the neuropeptide Y Y2 receptor, Nature America Inc. Oct. 1999, pp. 1188-1193, vol. 5, No. 10, Nature Medicine.

Akihiro Asakawa, Akio Inui, Naohiko Ueno, Mineko Fujimiya, Masayuki A. Fujino, Masato Kasuga, Mouse pancreatic polypeptide modulated food intake, while not influencing anxiety in mice, Peptides, 1999, pp. 1445-1448, vol. 20, Elsevier Science Inc.

Keire, D. A.; Mannon, P.; Kobayashi, M.; Walsh, J. H.; Solomon, T. E.; Reeve, J. R., Jr. Primary structures of PYY, [Pro $^{34}$]PYY, and PYY-(3-36) confer different conformations and receptor selectivity, Am.J.Physiol Gastrointest.Liver Physiol, Feb. 1, 2000, pp. G126-G131, vol. 279.

Anonymous: "Nastech Begins a Clinical Trial with Intranasal PYY in Overweight Adults," Dailydrugnews.com, Daily Essentials, Jan. 23, 2004, XP001207998.

Cervin, Anders, et al.: "Functional Effects of Neuropeptide Y Receptors on Blood Flow and Nitric Oxide Levels in the Human Nose," American Journal of Respiratory and Critical Care Medicine, pp. 1724-1728 v. 160, No. 5, Part I, Nov. 1999, XP002376387; ISSN: 1073-449X.

Suman, Julie D. et al.; "Validity of In Vitro Tests on Aqueous Spray Pumps as Surrogates for Nasal Deposition," Pharmaceutical Research (New York), pp. 1-6, v. 19, No. 1, Jan. 2002, XP002376388, ISSN: 0724-8741.

* cited by examiner

Group 1: 20 Micrograms Intranasal Dose
Pharmacokinetic Profile

Group 2: 50 Micrograms Intranasal Dose
Pharmacokinetic Profile

Group 3: 100 Micrograms Intranasal Dose
Pharmacokinetic Profile

Visual Analog Scale (VAS) results:

FIGURE 21 A
FIGURE 21 B
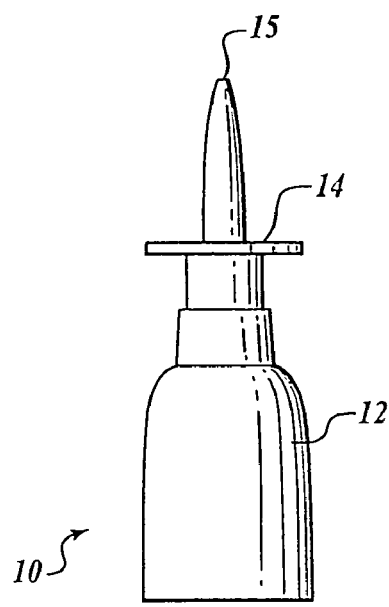
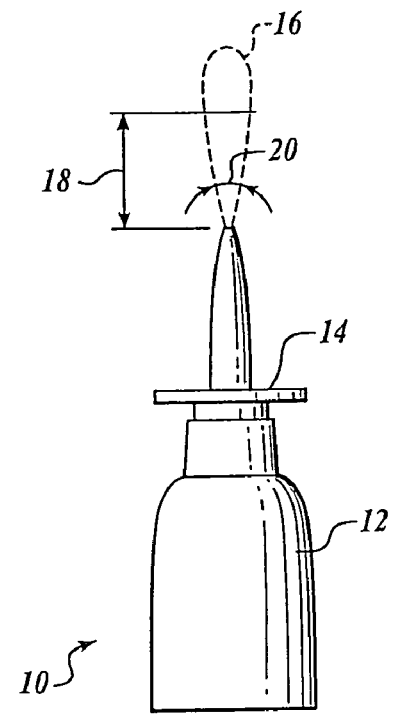
FIGURE 22,
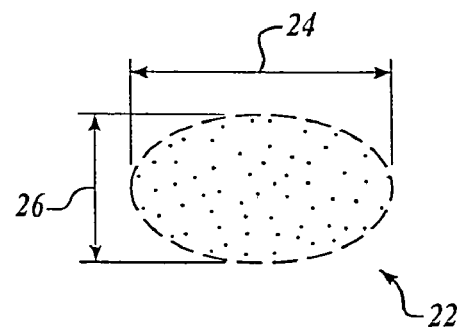

COMPOSITIONS AND METHODS FOR ENHANCED MUCOSAL DELIVERY AND NON-INFUSED ADMINISTRATION OF Y2 RECEPTOR-BINDING PEPTIDES AND METHODS FOR TREATING AND PREVENTING OBESITY

CROSS REFERENCE TO RELATED APPLICATIONS

This is a continuation-in-part application and claims priority under 35 U.S.C. §120 of co-pending, U.S. patent application Ser. No. 10/745,069 filed Dec. 23, 2003, which is a continuation-in-part of U.S. patent application Ser. No. 10/322,266, filed Dec. 17, 2002, and claims priority under 35 U.S.C. §119 (e) of:
U.S. Provisional Application No. 60/493,226, filed Aug. 7, 2003,
U.S. Provisional Application No. 60/501,170, filed Sep. 8, 2003,
U.S. Provisional Application No. 60/510,785, filed Oct. 10, 2003,
U.S. Provisional Application No. 60/517,290, filed Nov. 4, 2003;
U.S. Provisional Application No. 60/518,812, filed on Nov. 10, 2003; the entire contents of these applications are incorporated herein by reference

BACKGROUND OF THE INVENTION

The teachings of all the references cited in the present specification are incorporated in their entirety by reference.

Obesity and its associated disorders are common and very serious public health problems in the United States and throughout the world. Upper body obesity is the strongest risk factor known for type-2 diabetes mellitus, and is a strong risk factor for cardiovascular disease. Obesity is a recognized risk factor for hypertension, arteriosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia. It reduces life-span and carries a serious risk of co-morbidities above, as well disorders such as infections, varicose veins, acanthosis nigricans, eczema, exercise intolerance, insulin resistance, hypertension hypercholesterolemia, cholelithiasis, orthopedic injury, and thromboembolic disease. Obesity is also a risk factor for the group of conditions called insulin resistance syndrome, or "Syndrome X."

It has been shown that certain peptides that bind to the Y2 receptor when administered peripherally to a mammal induce weight loss. The Y2 receptor-binding peptides are neuropeptides that bind to the Y2 receptor. Neuropeptides are small peptides originating from large precursor proteins synthesized by peptidergic neurons and endocrine/paracrine cells. Often the precursors contain multiple biologically active peptides. There is great diversity of neuropeptides in the brain caused by alternative splicing of primary gene transcripts and differential precursor processing. The neuropeptide receptors serve to discriminate between ligands and to activate the appropriate signals. These Y2 receptor-binding peptides belong to a family of peptides including peptide YY (PYY), neuropeptide Y (NPY) and pancreatic peptide (PP).

NPY is a 36-amino acid peptide and is the most abundant neuropeptide to be identified in mammalian brain. NPY is an important regulator in both the central and peripheral nervous systems and influences a diverse range of physiological parameters, including effects on psychomotor activity, food intake, central endocrine secretion, and vasoactivity in the cardiovascular system. High concentrations of NPY are found in the sympathetic nerves supplying the coronary, cerebral, and renal vasculature and have contributed to vasoconstriction. NPY binding sites have been identified in a variety of tissues, including spleen, intestinal membranes, brain, aortic smooth muscle, kidney, testis, and placenta.

Neuropeptide Y (NPY) receptor pharmacology is currently defined by structure activity relationships within the pancreatic polypeptide family. This family includes NPY, which is synthesized primarily in neurons; PYY, which is synthesized primarily by endocrine cells in the gut; and PP, which is synthesized primarily by endocrine cells in the pancreas. These approximately 36 amino acid peptides have a compact helical structure involving a "PP-fold" in the middle of the peptide. Specific features include a polyproline helix in residues 1 through 8, a β-turn in residues 9 through 14, an α-helix in residues 15 through 30, an outward-projecting C-terminus in residues 30 through 36, and a carboxyl terminal amide, which appears to be critical for biological activity. The peptides have been used to define at least five receptor subtypes known as Y1, Y2, Y3, Y4 and Y5. Y1 receptor recognition by NPY involves both N- and C-terminal regions of the peptide; exchange of $Gln^{34}$ with $Pro^{34}$ is fairly well tolerated. Y2 receptor recognition by NPY depends primarily upon the four C-terminal residues of the peptide ($Arg^{33}$-$Gln^{34}$-$Arg^{35}$-$Tyr^{36}$-$NH_2$) preceded by an amphipathic an α-helix ; exchange of $Gln^{34}$ with $Pro^{34}$ is not well tolerated. One of the key pharmacological features which distinguish Y1 and Y2 is the fact that the Y2 receptor (and not the Y1 receptor) has high affinity for the NPY peptide carboxyl-terminal fragment NPY-(13–36) and the PYY fragment PYY(22–36).

It has been shown that a 36 amino acid peptide called Peptide YY(1–36) [PYY(1–36)] [YPIKPEAPGE-DASPEELNRYYASLRHYLNLVTRQRY, SEQ ID NO.: 1]. when administered peripherally by injection to an individual produces weight loss and thus can be used as a drug to treat obesity and related diseases, Morley, J. *Neuropsychobiology* 21:22–30 (1989). It was later found that to produce this effect PYY bound to a Y2 receptor, and the binding of a Y2 agonist to the Y2 receptor caused a decrease in the ingestion of carbohydrate, protein and meal size, Leibowitz, S. F. et al. *Peptides*, 12: 1251–1260 (1991). An alternate molecular form of PYY is PYY(3–36) IKPEAPGEDASPEELNRY-YASLRHYLNLVTRQRY [SEQ ID NO.: 2], Eberlein, Eysselein et al. *Peptides* 10: 797–803, 1989). This fragment constitutes approximately 40% of total PYY-like immunoreactivity in human and canine intestinal extracts and about 36% of total plasma PYY immunoreactivity in a fasting state to slightly over 50% following a meal. It is apparently a dipeptidyl peptidase-IV (DPP4) cleavage product of PYY. PYY3–36 is reportedly a selective ligand at the Y2 and Y5 receptors, which appear pharmacologically unique in preferring N-terminally truncated (i.e. C-terminal fragments of) NPY analogs. It has also been shown that a PYY fragment having only residues 22–36 will still bind to the Y2 receptor. However, if any of the carboxyl terminus of the peptide is cleaved, the peptide looses its ability to bind to the Y2 receptor. Hence a PYY agonist is a peptide, which has a partial sequence of full-length PYY and is able to bind to a Y2 receptor in the arcuate nucleus of the hypothalamus. Hereinafter the term PYY refers to full-length PYY and any fragment of PYY that binds to a Y2 receptor.

It is known that PYY and PYY3–36 can be administered by intravenous infusion or injection to treat life-threatening hypotension as encountered in shock, especially that caused by endotoxins (U.S. Pat. No. 4,839,343), to inhibit proliferation of pancreatic tumors in mammals by perfusion, parenteral, intravenous, or subcutaneous administration, and by implantation (U.S. Pat. No. 5,574,010) and to treat obesity (Morley, J. *Neuropsychobiology* 21:22–30 (1989) and U.S. Patent Application 20020141985). It is also claimed that PYY can be administered by parenteral, oral, nasal, rectal and topical routes to domesticated animals or humans in an amount effective to increase weight gain of said subject by enhancing gastrointestinal absorption of a sodium dependent cotransported nutrient (U.S. Pat. No. 5,912,227). However, for the treatment of obesity and related diseases, including diabetes, the mode of administration has been limited to intravenous IV infusion with no effective formulations optimized for alternative administration of PYY3–36. None of these prior art teachings provide formulations that contain PYY or PYY(3–36) combined with excipients designed to enhance mucosal (i.e., nasal, buccal, oral) delivery nor do they teach the value of endotoxin-free Y2-receptor binding peptide formulations for non-infused administration. Thus, there is a need to develop formulations and methods for administering PYY3–36.

The generation of aerosol formulations can enhance absorption of formulations on mucosal (nasal, buccal, oral, vaginal and rectal) surfaces as well as skin surfaces. Review: O'Riordan TG. Formulations and Nebulizer performance. Respir Care 2000 November; 47(11):1305–12; discussion 1312–3.

However, the physical forces associated with droplet formation often destroy or denature proteins and peptides. For example, recombinant human deoxyribonuclease (rhDNase) was substantially denatured during processing as shown by the significantly reduced monomer content. Similarly, albumin was affected by processing and only 50–75% of the monomer was retained compared with 86% in the original material. Bustami R T, Chan H K, Dehghani F, Foster N R. Generation of micro-particles of proteins for aerosol delivery using high pressure modified carbon dioxide. Pharm Res. 2000 November; 17(11):1360–6.

The physical stability of a peptide hormone human growth hormone (hGH) formulation upon exposure to air/water interfaces (with vortex mixing) has been investigated. The effect of this stress on the formation of soluble and insoluble aggregates has been studied. The aggregates were characterized and quantified by size exclusion-HPLC and UV spectrophotometry. Vortex mixing of hGH solutions (0.5 mg/mL) in phosphate buffer, pH 7.4, for just 1 min caused 67% of the drug to precipitate as insoluble aggregates. These aggregates were noncovalent in nature. Katakam M, Bell L N, Banga A K. J Pharm Sci. 1995 June; 84(6):713–6.

SUMMARY OF THE INVENTION

The present invention fulfills the foregoing needs and satisfies additional objects and advantages by providing novel, effective methods and compositions for delivery, especially mucosal, most especially intranasal, delivery of a Y2 receptor-binding peptide such as PYY, Pancreatic Peptide (PP) and NPY, to treat obesity, induce satiety in an individual and to promote weight-loss in an individual and prevent or cure diabetes. In certain aspects of the invention, the Y2 receptor-binding peptide is delivered in formulations to the intranasal mucosa so as to be able to increase the concentration of the Y2 receptor-binding peptide by at least 5 pmol, preferably by at least 10 pmol, in the blood plasma of a mammal when a dose of the formulations of the Y2 receptor agonist is administered intranasally. Furthermore preferred formulations would be able to raise the concentration of the Y2 receptor-binding peptide in the plasma of a mammal by 10 pmol, preferably 20 pmol, when the Y2 receptor-binding peptide is administered intranasally. When 150 μg is administered intranasally the preferred formulation would be able to raise the concentration of the Y2 receptor agonist in the plasma of the mammal by at least 40 pmol per liter of plasma. When 200 μg of the Y2 receptor-binding peptide is administered intranasally, the formulations of the present invention induce at least 80 pmol, per liter of plasma increase of the Y2 receptor-binding peptide. In preferred embodiments, the elevated concentrations of the Y2-receptor-binding peptide remains elevated in the plasma of the mammal for at least 30 minutes, preferably at least 60 minutes following a single intranasal dose of the Y2 receptor-binding peptide.

Preferably the Y2 receptor-binding peptide is a PP, PYY or NPY peptide and the mammal is a human. In a most preferred embodiment the Y2 receptor-binding peptide is a PYY peptide, preferably PYY(3–36) and the mammal is human.

The present invention is also related to a Y2 receptor-binding peptide formulation that is able to raise the concentration of the Y2 receptor-binding peptide in the blood plasma of a mammal by at least 5 pM when a dose containing at least 50 μg of the Y2 receptor-binding peptide is administered to the mammal. In preferred embodiments, the elevated concentrations of the Y2-receptor-binding peptide remains elevated in the plasma of the mammal for at least 30 minutes, preferably at least 60 minutes following a single intranasal dose of the Y2 receptor-binding peptide.

The present invention is also related to a Y2 receptor-binding peptide formulation that is able to raise the concentration of the Y2 receptor-binding peptide in the blood-plasma of a mammal by at least 20 pM when a dose containing at least 100 μg of the Y2 receptor-binding peptide is administered to the mammal. In preferred embodiments, the elevated concentrations of the Y2-receptor-binding peptide remains elevated in the plasma of the mammal for at least 30 minutes, preferably at least 60 minutes following a single intranasal dose of the Y2 receptor-binding peptide.

The present invention is also related to a Y2 receptor-binding peptide formulation that when administered intranasally to a mammal is able to raise the concentration of the Y2 receptor-binding peptide in blood plasma of the mammal by at least 30 pM when a dose containing at least 150 μg of the Y2 receptor-binding peptide is administered. In preferred embodiments, the elevated concentrations of the Y2-receptor-binding peptide remains elevated in the plasma of the mammal for at least 30 minutes, preferably at least 60 minutes following a single intranasal dose of the Y2 receptor-binding peptide. Preferably the mammal is a human.

The present invention is also related to a Y2 receptor-binding peptide formulation that when administered intranasally to a mammal is able to raise the concentration of the Y2 receptor-binding peptide by at least 60 pM when a dose containing at least 200 μg is administered to the mammal. In preferred embodiments, the elevated concentrations of the Y2-receptor-binding peptide remains elevated in the plasma of the mammal for at least 30 minutes, preferably at least 60 minutes following a single intranasal dose of the Y2 receptor-binding peptide. Preferably the mammal is a human.

The present invention is also directed to an intranasal formulation of a Y2 receptor-agonist that is substantially free of proteins or polypeptides that stabilize the formulation. In particular, the preferred formulation is free of such proteins as albumin, and collagen-derived proteins such as gelatin.

In other aspects of the present invention a transmucosal Y2 receptor-binding peptide formulation is comprised of a Y2 receptor-binding peptide, water and a solubilizing agent having a pH of 3–6.5. In a preferred embodiment, the solubilization agent is a cyclodextrin.

In another embodiment of the present invention a transmucosal Y2 receptor-binding peptide formulation is comprised of a Y2 receptor-binding peptide, water, a solubilizing agent, preferably a cyclodextrin, and at least one polyol, preferably 2 polyols. In alternate embodiments the formulation may contain one or all of the following: a chelating agent, a surface-acting agent and a buffering agent.

In another embodiment of the present invention the formulation is comprised of a Y2 receptor-binding peptide, water, chelating agent and a solubilization agent.

In another embodiment of the present invention the formulation is comprised of a Y2 receptor-binding peptide, water and a chelating agent having a pH of 3–6.5.

In another embodiment of the present invention the formulation is comprised of a Y2 receptor-binding peptide, water, chelating agent and at least one polyol, preferably two polyols. Additional embodiments may include one or more of the following: a surface-active agent, a solubilizing agent and a buffering agent.

In another embodiment of the present invention the formulation is comprised of a Y2 receptor-binding peptide, water, and at least two polyols, such as lactose and sorbitol. Additional agents, which can be added to the formulation, include, but are not limited to, a solubilization agent, a chelating agent, one or more buffering agents and a surface-acting agent.

In another embodiment of the present invention the formulation is comprised of a Y2 receptor-binding peptide, water, and a tonicifying agent, such as a salt. Such salts include, but are not limited to, sodium acetate, sodium bicarbonate, sodium carbonate, sodium chloride, potassium acetate, potassium bicarbonate, potassium carbonate, and potassium chloride. Additional agents, which can be added to the formulation, include, but are not limited to, a solubilization agent, a chelating agent, one or more buffering agents and a surface-acting agent. Other salts include gluconate, lactate, glucarate, benzoate, salicylate, tartrate, mesylate, tosylate, maleate, fumarate, stearate and citrate. Another appropriate salt are the salts of methylglucamine including the methyglucaminemethylglucamine acetate, gluconate, lactate, glucarate, benzoate, salicylate, tartrate, mesylate, tosylate, maleate, fumarate, stearate and citrate salts.

The enhancement of intranasal delivery of a Y2 receptor-binding peptide agonist according to the methods and compositions of the invention allows for the effective pharmaceutical use of these agents to treat a variety of diseases and conditions in mammalian subjects.

The present invention fills this need by providing for a liquid or dehydrated Y2 receptor-binding peptide formulation wherein the formulation is substantially free of a stabilizer that is a polypeptide or a protein. The liquid PYY formulation is comprised of water, PYY and at least one of the following additives selected from the group consisting of polyols, surface-active agents, solubilizing agents, chelating agents and tonicifying agents. The pH of the formulation is preferably 3 to about 7.0, preferably 3.8 to about 6.0, most preferably about 4.5±0.5.

Another embodiment of the present invention is an aqueous Y2 receptor-binding formulation of the present invention is comprised of water, a Y2 receptor-binding peptide, a polyol and a surface-active agent wherein the formulation has a pH of about 3.0 to about 6.5, and the formulation is substantially free of a stabilizer that is a protein or polypeptide.

Another embodiment of the present invention is an aqueous Y2 receptor-binding peptide formulation comprised of water, Y2 receptor-binding peptide, a polyol and a solubilizing agent wherein the formulation has a pH of about 3.0 to about 6.5, and the formulation is substantially free of a stabilizer that is a protein or polypeptide.

Another embodiment of the present invention is an aqueous Y2 receptor-binding peptide formulation comprised of water, Y2 receptor-binding peptide, a solubilizing agent and a surface-active agent wherein the formulation has a pH of about 3.0 to about 6.5, and the formulation is substantially free of a stabilizer that is a protein or polypeptide.

Another embodiment of the invention is a aqueous Y2 receptor-binding peptide formulation comprised of water, a Y2 receptor-binding peptide, a solubilizing agent, a polyol and a surface-active agent wherein the formulation has a pH of about 3.0 to about 6.5, and the formulation is substantially free of a stabilizer that is a protein or polypeptide.

In another aspect of the present invention, the stable aqueous formulation is dehydrated to produce a dehydrated Y2 receptor-binding peptide formulation comprised of Y2 receptor-binding peptide and at least one of the following additives selected from the group consisting of polyols, surface-active agents, solubilizing agents, chelating agents, and tonicitytonicifying agents wherein said dehydrated Y2 receptor-binding peptide formulation is substantially free of a stabilizer that is a protein or polypeptide such as albumin, collagen or collagen-derived protein such as gelatin. The dehydration can be achieved by various means such as lyophilization, spray-drying, salt-induced precipitation and drying, vacuum drying, rotary evaporation, or supercritical $CO_2$ precipitation.

In one embodiment, the dehydrated Y2 receptor-binding peptide is comprised of Y2 receptor-binding peptide, a polyol and a solubilizing agent, wherein the formulation is substantially free of a stabilizer that is a protein.

In another embodiment, the dehydrated Y2 receptor-binding peptide formulation is comprised of a Y2 receptor-binding peptide, a polyol, and a surface-active agent wherein the Y2 receptor-binding peptide formulation is substantially free of a stabilizer that is a protein or polypeptide.

In another embodiment, the dehydrated Y2 receptor-binding peptide formulation is comprised of a Y2 receptor-binding peptide, a surface-active agent, and a solubilizing agent wherein the Y2 receptor-binding peptide formulation is substantially free of a stabilizer that is a protein or polypeptide.

In another embodiment of the present invention, the dehydrated Y2 receptor-binding peptide formulation is comprised of a Y2 receptor-binding peptide, a polyol, a surface-active agent and a solubilizing agent wherein the Y2 receptor-binding peptide formulation is substantially free of a stabilizer that is a protein or polypeptide.

Any solubilizing agent can be used but a preferred one is selected from the group consisting of hydroxypropyl-β-cyclodextrin, sulfobutylether-β-cyclodextrin, methyl-β-cyclodextrin and chitosan.

Generally a polyol is selected from the group consisting of lactose, sorbitol, trehalose, sucrose, mannose and maltose, the non-reducing polyol derivatives thereof and other derivatives and homologs thereof.

A satisfactory surface-active agent is selected from the group consisting of L-α-phosphatidylcholine didecanoyl (DDPC), polysorbate 20 (Tween 20), polysorbate 80 (Tween 80), polyethylene glycol (PEG), cetyl alcohol, polyvinylpyrolidone (PVP), polyvinyl alcohol (PVA), lanolin alcohol, and sorbitan monooleate. Any surface-active agent that lowers the surface tension of pure water from about 60 dynes-cm2 to less than 50 dynes-cm2 is suitable for use herein.

Appropraite tonifying salts include, but are not limited to sodium acetate, sodium bicarbonate, sodium carbonate, sodium chloride, potassium acetate, potassium bicarbonate, potassium carbonate, and potassium chloride.

A satisfactory surface-active agent is selected from the group consisting of L-α-phosphatidylcholine didecanoyl (DDPC), sphingomyelin, phosphatidylethanolamine, polysorbate 20 (Tween 20), polysorbate 80 (Tween 80), polyethylene glycol (PEG), cetyl alcohol, polyvinylpyrolidone (PVP), polyvinyl alcohol (PVA), lanolin alcohol, and sorbitan monooleate.

Appropriate tonicifying salts include, but are not limited to sodium acetate, sodium bicarbonate, sodium carbonate, sodium chloride, potassium acetate, potassium bicarbonate, potassium carbonate, and potassium chloride.

In a preferred formulation, the Y2 receptor-binding peptide formulation is also comprised of a chelating agent such as diethylene triamine tetraacetic acid (DTPA), ethylene diamine tetraacetic acid (EDTA) (including edetate calcium disodium, edetate disodium, and edetate trisodium), deferiprone, deferoxamine, ditiocarb sodium, penicillamine, pentetate calcium trisodium, pentetic acid, succimer, trientine or ethylene glycol tetraacetic acid (EGTA). Also a preservative such as chlorobutanol, methyl paraben, propyl paraben, sodium benzoate (0.5%), phenol, cresol, p-chloro-m-cresol, phenylethyl alcohol, benzyl alcohol, phenylmercuric acetate, phenylmercuric borate, phenylmercuric nitrate, thimerosal, sorbic acid, benzethonium chloride or benzylkonium chloride can be added to the formulation to inhibit microbial growth.

The pH is generally regulated using a buffer such as a system comprised of citric acid and a citrate salt(s), such as sodium citrate. Additional suitable buffer systems include acetic acid and an acetate salt system, succinic acid and a succinate salt system, malic acid and a malic salt system, and gluconic acid and a gluconate salt system. Alternatively, buffer systems comprised of mixed acid/salt systems can be employed, such as an acetic acid and sodium citrate system, a citrate acid, sodium acetate system, and a citric acid, sodium citrate, sodium benzoate system. For any buffer system, additional acids, such as hydrochloric acid, and additional bases, such as sodium hydroxide, may be added for final pH adjustment.

The preferred Y2 receptor-binding peptide is a PYY, PP or NPY peptide, preferably a PYY(3–36) peptide. The Y2 receptor-binding peptide can be made by chemical synthesis. Alternatively, it can be made by recombinant technology. PYY can be expressed in mammalian cells such as Chinese Hamster Ovary (CHO) cells or in bacteria using techniques well-known in the art. One form of recombinant technology comprises a production system based on producing PYY as a fusion protein with a partner that has been used successfully with many different proteins/peptides. Separation can be by a chemical cleavage process. Any number of methods can be used for C-terminal amidation including two chemical methods. Chemical modification would be preferable to a method involving the production of the C-terminal glycine derivative of PYY followed by reaction with the enzyme peptidylglycine alpha-amidating enzyme. One can get yields that range between 5 and 15 grams per liter. Because of the properties of a fusion system the purification process is very efficient; using mostly batch processes, and does not require expensive steps such as affinity chromatography. Any other recombinant technology that can produce the Y2 receptor agonists can be used.

The present invention also comprehends a formulation wherein the concentration of the Y2 receptor-binding peptide is 0.1–15.0 mg/mL, preferably 1.0–2 mg/mL and the pH of the aqueous solution is 3.0–6.5 preferably about 4.5±0.5.

The present invention further includes Y2 receptor-binding peptide formulation wherein the concentration of the polyol is between about 0.1% and 10% (w/v) and additionally wherein the concentration of the polyol is in the range from about 0.1% to about 3% (w/v).

The instant invention also includes a formulation, wherein the concentration of the surface-active agent is between about 0.00001% and about 5% (w/v), and wherein the concentration of the surface-active agent is between about 0.0002% and about 0.1% (w/v).

The instant invention also includes a formulation, wherein the concentration of the solubilization agent is 1%–10% (w/v), and wherein the concentration of the solubilizing agent is 2% to 5% (w/v).

The finished solution can be filtered and freeze-dried, lyophilized, using methods well known to one of ordinary skill in the art, and by following the instructions of the manufacturer of the lyophilizing equipment. This produces a dehydrated Y2 receptor-binding peptide formulation substantially free of a stabilizer that is a protein.

In another embodiment of the present invention, a Y2 receptor-binding peptide formulation is comprised of an Y2 receptor-binding peptide and a pharmaceutically acceptable carrier wherein the Y2 receptor-bind peptide formulation has at least 1%, preferably 3% and most preferably at least 6% higher permeation in an in vitro tissue permeation assay than a control formulation consisting of water, sodium chloride, a buffer and the Y2 receptor-binding peptide, as determined by the transepithelial electrical resistance assay shown in Examples 2 & 7. In a preferred embodiment, the Y2 receptor-binding formulation is further comprised of at least one excipient selected from the group consisting of a surface-active agent, a solubilization agent, a polyol, and a chelating agent. Preferably the Y2 receptor-binding peptide is a PYY peptide, an NPY peptide or a PP peptide.

In another embodiment of the present invention a Y2 receptor-binding peptide formulation is provided that is capable of raising the concentration of the Y2 receptor-binding peptide in the plasma of a mammal by at least 5 preferably 10, 20 40, 60, 80 or more pmoles per liter of plasma when 100 μL of the formulation is administered intranasally to said mammal.

In exemplary embodiments, the enhanced delivery methods and compositions of the present invention provide for therapeutically effective mucosal delivery of the Y2 receptor-binding peptide agonist for prevention or treatment of obesity and eating disorders in mammalian subjects. In one aspect of the invention, pharmaceutical formulations suitable for intranasal administration are provided that comprise a therapeutically effective amount of a Y2 receptor-binding peptide and one or more intranasal delivery-enhancing agents as described herein, which formulations are effective in a nasal mucosal delivery method of the invention to prevent the onset or progression of obesity or eating disorders in a mammalian subject. Nasal mucosal delivery of a therapeutically effective amount of a Y2 receptor-binding peptide agonist and one or more intranasal delivery-enhancing agents yields elevated therapeutic levels of the Y2 receptor-binding peptide agonist in the subject and inhibits food intake in the mammalian subject, reducing symptoms of obesity or an eating disorder.

The enhanced delivery methods and compositions of the present invention provide for therapeutically effective mucosal delivery of a Y2 receptor-binding peptide for prevention or treatment of a variety of diseases and conditions in mammalian subjects. Y2 receptor-binding peptide can be administered via a variety of mucosal routes, for example by contacting the Y2 receptor-binding peptide to a nasal mucosal epithelium, a bronchial or pulmonary mucosal epithelium, the oral buccal surface or the oral and small intestinal mucosal surface. In exemplary embodiments, the methods and compositions are directed to or formulated for intranasal delivery (e.g., nasal mucosal delivery or intranasal mucosal delivery).

In one aspect of the invention, pharmaceutical formulations suitable for intranasal administration are provided that comprise a therapeutically effective amount of a Y2 receptor-binding peptide agonist and one or more intranasal delivery-enhancing agents as described herein, which formulations are effective in a nasal mucosal delivery method of the invention to prevent the onset or progression of obesity, diabetes, cancer, or malnutrition or wasting related to cancer in a mammalian subject, or to alleviate one or more clinically well-recognized symptoms of obesity, as well as treating Alzheimer's disease, colon carcinoma, colon adenocarcinoma, pancreatic carcinoma, pancreatic adenocarcinoma, breast carcinoma.

In another aspect of the invention, pharmaceutical formulations and methods are directed to administration of a Y2 receptor-binding peptide agonist in combination with vitamin E succinate. A Y2 receptor-binding peptide agonist in combination with vitamin E succinate may be administered to alleviate symptoms or prevent the onset or lower the incidence or severity of cancer, for example, colon adenocarcinoma, pancreatic adenocarcinoma, or breast cancer.

In another aspect of this invention, it was surprisingly found that the use of endotoxin-free Y2 receptor binding peptides, for example PYY(3–36), produced increased mucosal delivery compared to peptides in which endotoxin is not removed. The use of endotoxin-free Y2 receptor peptides in pharmaceutical formulations is thus enabled for administration by non-infusion routes, including mucosal delivery, nasal, oral, pulmonary, vaginal, rectal and the like.

The foregoing mucosal Y2 receptor-binding peptide formulations and preparative and delivery methods of the invention provide improved mucosal delivery of a Y2 receptor-binding peptide to mammalian subjects. These compositions and methods can involve combinatorial formulation or coordinate administration of one or more Y2 receptor-binding peptides with one or more mucosal delivery-enhancing agents. Among the mucosal delivery-enhancing agents to be selected from to achieve these formulations and methods are (A) solubilization agents; (B) charge modifying agents; (C) pH control agents; (D) degradative enzyme inhibitors; (E) mucolytic or mucus clearing agents; (F) ciliostatic agents; (G) membrane penetration-enhancing agents (e.g., (i) a surfactant, (ii) a bile salt, (iii) a phospholipid or fatty acid additive, mixed micelle, liposome, or carrier, (iv) an alcohol, (v) an enamine, (iv) an NO donor compound, (vii) a long-chain amphipathic molecule (viii) a small hydrophobic penetration enhancer; (ix) sodium or a salicylic acid derivative; (x) a glycerol ester of acetoacetic acid (xi) a cyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis, (xviii) an inhibitor of cholesterol synthesis; or (xiv) any combination of the membrane penetration enhancing agents of (i)–(xviii)); (H) modulatory agents of epithelial junction physiology, such as nitric oxide (NO) stimulators, chitosan, and chitosan derivatives; (I) vasodilator agents; (J) selective transport-enhancing agents; and (K) stabilizing delivery vehicles, carriers, supports or complex-forming species with which the Y2 receptor-binding peptide (s) is/are effectively combined, associated, contained, encapsulated or bound to stabilize the active agent for enhanced mucosal delivery.

In various embodiments of the invention, a Y2 receptor-binding peptide is combined with one, two, three, four or more of the mucosal delivery-enhancing agents recited in (A)–(K), above. These mucosal delivery-enhancing agents may be admixed, alone or together, with the Y2 receptor-binding peptide, or otherwise combined therewith in a pharmaceutically acceptable formulation or delivery vehicle. Formulation of a Y2 receptor-binding peptide with one or more of the mucosal delivery-enhancing agents according to the teachings herein (optionally including any combination of two or more mucosal delivery-enhancing agents selected from (A)–(K) above) provides for increased bioavailability of the y2 receptor-binding peptide following delivery thereof to a mucosal surface of a mammalian subject.

Thus, the present invention is a method for suppressing appetite, promoting weight loss, decreasing food intake, or treating obesity and/or diabetes in a mammal comprising transmucosally administering a formulation comprised of a Y2 receptor-binding peptide, such that when at 50 µg of the Y2 receptor is administered transmucosally to the mammal the concentration of the Y2 receptor-binding peptide in the plasma of the mammal increases by at least 5 pmol, preferably at least 10 pmol per liter of plasma. Examples of such formulations are described above.

The present invention further provides for the use of a Y2 receptor-binding peptide for the production of medicament for the transmucosal, administration of a Y2 receptor-binding peptide for suppressing appetite, promoting weight loss, decreasing food intake, or treating obesity in a mammal such that when about 50 µg of the Y2 receptor is administered transmucosally to the mammal the concentration of the Y2 receptor-binding peptide in the plasma of the mammal increases by at least 5 pmol per liter of plasma. When 100 µg of the Y2 receptor-binding peptide is administered intranasally to the mammal, the concentration of the Y2 receptor agonist increases by at least 20 pmol per liter of plasma in the mammal. When 150 µg is administered intranasally, the concentration of the Y2 receptor-binding peptide in blood plasma of the mammal increases by at least 30 pM. When 200 µg is administered intranasally, the concentration of the Y2 receptor-binding peptide in blood plasma of the mammal increases by at least 60 pM. In preferred embodiments, the elevated concentrations of the Y2-receptor-binding peptide remains elevated in the plasma of the mammal for at least 30 minutes, preferably at least 60 minutes following a single intranasal dose of the Y2 receptor-binding peptide. Preferably the mammal is a human.

A mucosally An effective dose of peptide YY for mucosal administration within the pharmaceutical formulations of the present invention comprises, for example, between about 0.001 pmol to about 100 pmol per kg body weight, between about 0.01 pmol to about 10 pmol per kg body weight, or between about 0.1 pmol to about 5 pmol per kg body weight. In further exemplary embodiments, dosage of peptide YY is between about 0.5 pmol to about 1.0 pmol per kg body weight. In a preferred embodiment an intranasal dose will range from 40 µg to 200 µg, or from 45 µg to 150 µg, from about 50 µg to 100 µg, from about 55 µg to about 85 µg, from 65 µg to about 75 µg, from 45 µg to about 55 µg. The pharmaceutical formulations of the present invention may be administered one or more times per day (for example, before a meal), or 3 times per week or once per week for between one week and at least 96 weeks or even for the life of the individual patient or subject. In certain embodiments, the pharmaceutical formulations of the invention are administered at least one or more times daily, at least two times daily, at least four times daily, at least six times daily, or at least eight times daily. Preferably, the Y2 receptor-binding peptide should be administered from 30 to 90 minutes prior to eating.

Intranasal delivery-enhancing agents are employed which enhance delivery of peptide YY into or across a nasal mucosal surface. For passively absorbed drugs, the relative contribution of paracellular and transcellular pathways to drug transport depends upon the pKa, partition coefficient, molecular radius and charge of the drug, the pH of the luminal environment in which the drug is delivered, and the area of the absorbing surface. The intranasal delivery-enhancing agent of the present invention may be a pH control agent. The pH of the pharmaceutical formulation of the present invention is a factor affecting absorption of peptide YY via paracellular and transcellular pathways to drug transport. In one embodiment, the pharmaceutical formulation of the present invention is pH adjusted to between about pH 3.0 to 6.5. In a further embodiment, the pharmaceutical formulation of the present invention is pH adjusted to between about pH 3.0 to 5.0. In a further embodiment, the pharmaceutical formulation of the present invention is pH adjusted to between about pH 4.0 to 5.0. Generally, the pH is 4.5±0.5.

The instant invention also describes the surprising ability to successfully aerosolize the Y2 receptor binding compound, PYY(3–36), from an aqueous formulation.

BRIEF DESCRIPTION OF THE DRAWINGS

In FIGS. 2–4
EN1=PBS pH 5.0
EN2=L-Arginine (10% w/v)
EN3=Poly-L-Arginine (0.5% w/v)
EN4=Gamma-Cyclodextrin (1% w/v)
EN5=Alpha-Cyclodextrin (5% w/v)
EN6=Methyl-Beta-Cyclodextrin (3% w/v)
EN7=n-Capric Acid Sodium (0.075% w/v)
EN8=Chitosan (0.5% w/v)
EN9=L-Alpha-phosphatidylcholine didecanoyl (3.5% w/v)
EN10=S-Nitroso-N-acetylpenicillamine, (0.02% w/v)
EN11=Palmotoyl-DL-Carnitine (0.5% w/v)
EN12=Pluronic-127 (0.3% w/v)
EN13=Sodium Nitroprusside (0.3% w/v)
EN14=Sodium Glycocholate (1% w/v)

In FIG. 5 EN1 is DDPC, EN2 is methyl-β-cyclodextrin, and EX1 is EDTA.

FIG. 21A shows a nasal spray pump/actuator that is not engaged.

FIG. 21B shows the nasal spray pump/actuator that is engaged and expelling a spray plume.

FIG. 22 shows an example of a spray pattern of a PYY nasal spray of the present invention.

DETAILED DESCRIPTION OF THE INVENTION

Figure 1:
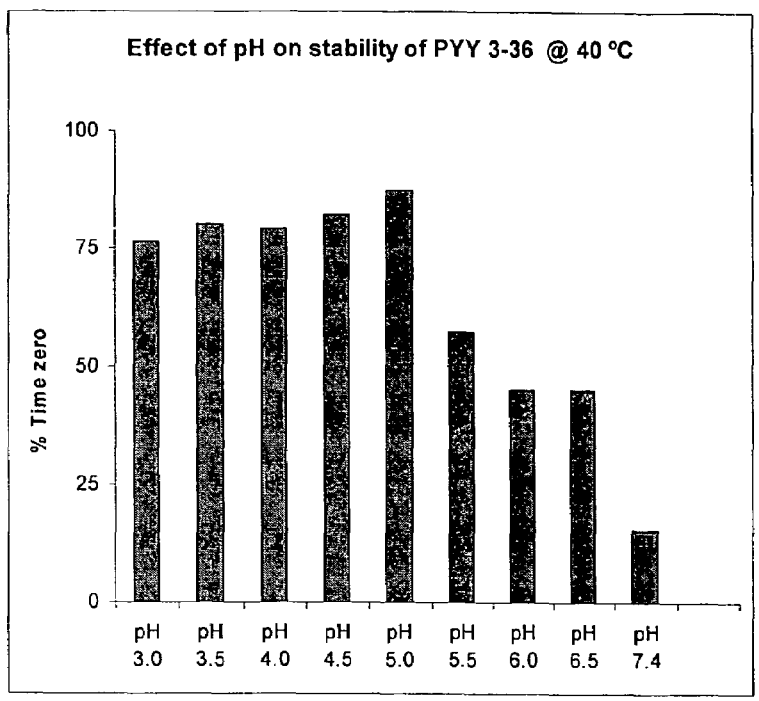
FIG. 1 shows the stability of PYY3–36 at high temperature (40° C.) at various pHs from 3.0 to 7.4.

As noted above, the present invention provides improved methods and compositions for mucosal delivery of Y2 receptor-binding peptide to mammalian subjects for treatment or prevention of a variety of diseases and conditions. Examples of appropriate mammalian subjects for treatment and prophylaxis according to the methods of the invention include, but are not restricted to, humans and non-human primates, livestock species, such as horses, cattle, sheep, and goats, and research and domestic species, including dogs, cats, mice, rats, guinea pigs, and rabbits.

In order to provide better understanding of the present invention, the following definitions are provided:

Y2 Receptor-Binding Peptides

The Y2 receptor-binding peptides used in the mucosal formulations of the present invention include the "pancreatic polypeptide family," as used herein, which is comprised of three naturally occurring bioactive peptide families, PP, NPY, and PYY. Examples of Y2 receptor-binding peptides and their uses are described in U.S. Pat. No. 5,026,685; U.S. Pat. No. 5,574,010; U.S. Pat. No. 5,604,203; U.S. Pat. No. 5,696,093; U.S. Pat. No. 6,046,167; Gehlert et. al., *Proc Soc Exp Biol Med* 218:7–22 (1998); Sheikh et al. *Am J Physiol*, 261:701–15(1991); Fournier et al., *Mol Pharmacol* 45:93–101 (1994); Kirby et al., *J Med Chem* 38:4579–4586 (1995); Rist et al., *Eur J Biochem* 247: 1019–1028 (1997); Kirby et al., *J Med Chem* 36:3802–3808 (1993); Grundemar et al., *Regulatory Peptides* 62: 131–136 (1996); U.S. Pat. No. 5,696,093 (examples of PYY agonists), U.S. Pat. No. 6,046,167, all of which are incorporated in their entirety herein by reference. According to the present invention a Y2 receptor-binding peptide includes the free bases, acid addition salts or metal salts, such as potassium or sodium salts, or divalent salts, including zinc, calcium, magnesium, and others, or the peptides Y2 receptor-binding peptides that have been modified by such processes as amidation, glycosylation, acylation, sulfation, phosphorylation, acetylation and cyclization, (U.S. Pat. No. 6,093,692; and U.S. Pat. No. 6,225,445, incorporated in their entirety herein by reference, and pegylation.

Peptide YY Agonists

As used herein, "PYY" refers to PYY(1–36) in native-sequence or in variant form, as well as derivatives, fragments, and analogs of PYY from any source, whether natural, synthetic, or recombinant. The PYY must be comprised at least the last 10 amino acid residues and preferably 15 amino acid residues or analogues thereof of the PYY sequence, PYY(22–36) (SEQ ID NO: 3). Other PYY peptides, which may be used are PYY(1–36) (SEQ ID NO: 1) PYY(3–36) SEQ ID NO: 2) PYY(4–36)(SEQ ID NO:4) PYY(5–36) (SEQ ID NO: 5), PYY(6–36) (SEQ ID NO:6), PYY(7–36) (SEQ ID NO:7) PYY(8–36) (SEQ ID NO: 8), PYY9–36 (SEQ ID NO: 9) PYY(10–36) (SEQ ID NO: 10), PYY(11–36) (SEQ ID NO: 11), PYY(12–36) (SEQ ID NO: 12), PYY(13–36) (SEQ ID NO:13), PYY(14–36) (SEQ ID NO: 14), PYY(15–36) (SEQ ID NO: 15), PYY(16–36) (SEQ ID NO: 16), PYY(17–36) (SEQ ID NO: 17), PYY (18–36) (SEQ ID NO: 18), PYY(19–36) (SEQ ID NO: 19), PYY(20–36) (SEQ ID NO: 20) and PYY(21–36) (SEQ ID NO: 21). These peptides typically bind to the Y receptors in the brain and elsewhere, especially the Y2 and/or Y5 receptors. Typically these peptides are synthesized in endotoxin-free or pyrogen-free forms although this is not always necessary.

Other PYY peptides include those PYY peptides in which conservative amino acid residue changes have been made, for example, site specific mutation of a PYY peptide including [Asp$^{15}$] PYY(15–36) (SEQ ID NO: 90), [Thr$^{13}$] PYY (13–36) (SEQ ID NO: 91), [Val$^{12}$] PYY(12–36)(SEQ ID NO: 92), [Glu$^{11}$] PYY(11–36) (SEQ ID NO: 93), [Asp$^{10}$] PYY(10–36) (SEQ ID NO: 94), [Val$^{7}$] PYY(7–36) (SEQ ID NO: 95), [Asp$^{6}$] PYY(6–36) (SEQ ID NO: 96), [Gln$^{4}$] PYY(4–36) (SEQ ID NO: 97), [Arg$^{4}$] PYY(4–36) (SEQ ID NO: 98), [Asn$^{4}$] PYY(4–36) (SEQ ID NO: 99), [Val$^{3}$] PYY(3–36) (SEQ ID NO: 100) and [Leu$^{3}$] PYY(3–36) (SEQ ID NO: 101). Other PYY peptides include those peptides in which at least two conservative amino acid residue changes have been made including [Asp$^{10}$, Asp$^{15}$] PYY(10–36) (SEQ ID NO: 102), [Asp$^{6}$, Thr$^{13}$] PYY(6–36) (SEQ ID NO: 103), [Asn$^{4}$, Asp$^{15}$] PYY(4–36) (SEQ ID NO: 104) and [Leu$^{3}$, Asp$^{10}$] PYY(3–36) (SEQ ID NO: 105. Also included are analogues of a PYY for example those disclosed in U.S. Pat. Nos. 5,604,203 and 5,574,010; Balasubramaniam, et al., *Peptide Research* 1: 32 (1988); Japanese Patent Application 2,225,497 (1990); Balasubramaniam, et al., *Peptides* 14: 1011, 1993; Grandt, et at., *Reg. Peptides* 51: 151, (1994); PCT International Application 94/03380, U.S. Pat. Nos. 5,604,203 and 5,574,010. These peptides typically bind to the Y receptors in the brain and elsewhere, especially the Y2 and/or Y5 receptors. Typically these peptides are synthesized in endotoxin-free or pyrogen-free forms although this is not always necessary.

PYY agonists include rat PYY (SEQ ID NO: 72) and the amino terminus truncated forms corresponding to the human, pig PYY (SEQ ID NO: 73) and the amino terminus truncated forms corresponding to the human and guinea pig PYY (SEQ ID NO: 74) and the amino terminus truncated forms corresponding to the human.

According to the present invention a PYY peptide also includes the free bases, acid addition salts or metal salts, such as potassium or sodium salts of the peptides, and PYY peptides that have been modified by such processes as amidation, glycosylation, acylation, sulfation, phosphorylation, acetylation, cyclization and other well known covalent modification methods. These peptides typically bind to the Y receptors in the brain and elsewhere, especially the Y2 and/or Y5 receptors. Typically these peptides are synthesized in endotoxin-free or pyrogen-free forms although this is not always necessary.

Neuropeptide Y Agonists

NPY is another Y2 receptor-binding peptide. NPY peptides include full-length NPY(1–36) (SEQ ID NO: 22) as well as well as fragments of NPY(1–36), which have been truncated at the amino terminus. To be effective in binding the Y2 receptor, the NPY agonist should have at least the last11 amino acid residues at the carboxyl terminus, i.e., be comprised of NPY(26–36) (SEQ ID NO: 23). Other examples of NPY agonists that bind to the Y2 receptor are NPY(3–36) (SEQ ID NO: 24), NPY(4–36) (SEQ ID NO: 25), NPY(5–36) (SEQ ID NO: 26), NPY(6–36) (SEQ ID NO: 27), NPY(7–36) (SEQ ID NO: 28), NPY(8–36) (SEQ ID NO: 29), NPY(9–36) (SEQ ID NO: 30), NPY(10–36) (SEQ ID NO: 31), NPY(11–36) (SEQ ID NO: 32), NPY (12–36) (SEQ ID NO: 33), NPY(13–36) (SEQ ID NO: 34), NPY(14–36) (SEQ ID NO: 35), NPY(15–36) (SEQ ID NO: 36), NPY(16–36) (SEQ ID NO: 37), NPY(17–36) (SEQ ID NO: 38), NPY(18–36) (SEQ ID NO: 39), NPY(19–36) (SEQ ID NO: 40), NPY(20–36) (SEQ ID NO: 41), NPY (21–36) (SEQ ID NO: 42), NPY(22–36) (SEQ ID NO: 43), NPY(23–36) (SEQ ID NO: 44), NPY(24–36) (SEQ ID NO: 45) and NPY(25–36) (SEQ ID NO: 46).

Other NPY agonists include rat NPY (SEQ ID NO: 75) and the amino terminus truncated forms from NPY(3–36) to NPY(26–36) as in the human form, rabbit NPY (SEQ ID NO: 76) and the amino terminus truncated forms from NPY(3–36) to NPY(26–36) as in the human form, dog NPY (SEQ ID NO: 77) and the amino terminus truncated forms NPY(3–36) to NPY(26–36) as in the human form, pig NPY (SEQ ID NO: 78) and the amino terminus truncated forms from NPY(3–36) to NPY(26–36) as in the human form, cow NPY (SEQ ID NO: 79) and the amino terminus truncated forms from NPY(3–36) to NPY26–36 as in the human form, sheep NPY (SEQ ID NO:80) and the amino terminus truncated forms from NPY(3–36) to NPY(26–36) as in the human form and guinea pig (SEQ 81) and the amino terminus truncated forms from NPY(3–36) to NPY(26–36) as in the human form.

According to the present invention a NPY peptide also includes the free bases, acid addition salts or metal salts, such as potassium or sodium salts of the peptides, and NPY peptides that have been modified by such processes as amidation, glycosylation, acylation, sulfation, phosphorylation, acetylation, cyclization and other known covalent modification methods. These peptides typically bind to the Y receptors in the brain and elsewhere, especially the Y2 and/or Y5 receptors. Typically these peptides are synthesized in endotoxin-free or pyrogen-free forms although this is not always necessary.

Pancreatic Peptide

Pancreatic Peptide (PP) and PP agonist also bind to the Y2 receptor. Examples of the PP agonists are the full-length PP(1–36) (SEQ ID NO: 47) and a number of PP fragments, which are truncated at the amino-terminus. To bind to the Y2 receptor the PP agonist must have the last 11 amino acid residues at the carboxyl-terminus, PP(26–36), (SEQ ID NO: 48). Examples of other PP, which bind to the Y2 receptor, are PP(3–36) (SEQ ID NO: 49), PP(4–36) (SEQ ID NO: 50), PP(5–36) (SEQ ID NO: 51), PP(6–36) (SEQ ID NO: 52), PP(7–36) (SEQ ID NO: 53), PP(8–36) (SEQ ID NO: 54), PP(9–36) (SEQ ID NO: 55), PP(10–36) (SEQ ID NO: 56), PP(11–36) (SEQ ID NO: 57), PP(12–36) (SEQ ID NO: 58), PP(13–36) (SEQ ID NO: 59), PP(14–36) (SEQ ID NO: 60), PP(15–36) (SEQ ID NO: 61), PP(16–36) (SEQ ID NO: 62), PP(17–36) (SEQ ID NO: 63), PP(18–36) (SEQ ID NO: 64), PP(19–36) (SEQ ID NO: 65), PP(20–36) (SEQ ID NO: 66), PP(21–36) (SEQ ID NO: 67), PP(22–36) (SEQ ID NO: 68), PP(23–36) (SEQ ID NO: 69), PP(24–36) (SEQ ID NO: 70) and PP(25–36) (SEQ ID NO: 71).

Other PP agonists include sheep PP (SEQ ID NO: 82) and the amino terminus truncated forms from PP(3–36) to PP(26–36) as in the human form, pig PP (SEQ ID NO: 83) and the amino terminus truncated forms from PP(3–36) to PP(26–36) as in the human form, dog PP (SEQ ID NO: 84) and the amino terminus truncated forms PP(3–36) to PP(26–36) as in the human form, cat PP (SEQ ID NO: 85) and the amino terminus truncated forms from PP(3–36) to PP(26–36) as in the human form, cow PP (SEQ ID NO: 86) and the amino terminus truncated forms from PP(3–36) to PP(26–36) as in the human form, rat PP (SEQ ID NO:87) and the amino terminus truncated forms from PP(3–36) to PP(26–36) as in the human form, mouse (SEQ 88) and the amino terminus truncated forms from PP(3–36) to PP(26–36) as in the human form, and guinea pig PP (SEQ ID NO: 89).

According to the present invention a PP peptide also includes the free bases, acid addition salts or metal salts, such as potassium or sodium salts of the peptides, and PP peptides that have been modified by such processes as amidation, glycosylation, acylation, sulfation, phosphorylation, acetylation, cyclization, and other known covalent modification methods. These peptides typically bind to the Y receptors in the brain and elsewhere, especially the Y2 and/or Y5 receptors. Typically these peptides are synthesized in endotoxin-free or pyrogen-free forms although this is not always necessary.

Mucosal Delivery Enhancing Agents

"Mucosal delivery enhancing agents" are defined as chemicals and other excipients that, when added to a formulation comprising water, salts and/or common buffers and Y2 receptor-binding peptide (the control formulation) produce a formulation that produces a significant increase in transport of Y2 receptor-binding peptide across a mucosa as measured by the maximum blood, serum, or cerebral spinal fluid concentration ($C_{max}$) or by the area under the curve, AUC, in a plot of concentration versus time. A mucosa includes the nasal, oral, intestinal, buccal, bronchopulmonary, vaginal, and rectal mucosal surfaces and in fact includes all mucus-secreting membranes lining all body cavities or passages that communicate with the exterior. Mucosal delivery enhancing agents are sometimes called carriers.

Endotoxin-Free Formulation

"Endotoxin-free formulation" means a formulation which contains a Y2-receptor-binding peptide and one or more mucosal delivery enhancing agents that is substantially free of endotoxins and/or related pyrogenic substances. Endotoxins include toxins that are confined inside a microorganism and are released only when the microorganisms are broken down or die. Pyrogenic substances include fever-inducing, thermostable substances (glycoproteins) from the outer membrane of bacteria and other microorganisms. Both of these substances can cause fever, hypotension and shock if administered to humans. Producing formulations that are endotoxin-free can require special equipment, expert artisans, and can be significantly more expensive than making formulations that are not endotoxin-free. Because intravenous administration of NPY or PYY simultaneously with infusion of endotoxin in rodents has been shown to prevent the hypotension and even death associated with the administration of endotoxin alone (U.S. Pat. No. 4,839,343), producing endotoxin-free formulations of these therapeutic agents would not be expected to be necessary for non-parental (non-injected) administration.

Non-Infused Administration

"Non-infused administration" means any method of delivery that does not involve an injection directly into an artery or vein, a method which forces or drives (typically a fluid) into something and especially to introduce into a body part by means of a needle, syringe or other invasive method. Non-infused administration includes subcutaneous injection, intramuscular injection, intraperitoneal injection and the non-injection methods of delivery to a mucosa. Non-infused Administration can be to a human or a non-human animal.

Treatment and Prevention of Obesity

As noted above, the instant invention provides improved and useful methods and compositions for nasal mucosal delivery of a Y2 receptor-binding peptide to prevent and treat obesity in mammalian subjects. As used herein, prevention and treatment of obesity mean prevention of the onset or lowering the incidence or severity of clinical obesity by reducing food intake during meals and/or reducing body weight during administration or maintaining a reduced body weight following weight loss or before weight gain has occurred.

The instant invention provides improved and useful methods and compositions for nasal mucosal delivery of Y2 receptor-binding peptide to regions of the brain, for example, the hypothalamus or the proopiomelanocortin (POMC) and NPY arcuate neurons, to prevent and treat obesity in mammalian subjects. The Y2 receptor-binding peptide can also be administered in conjunction with a Y1 receptor antagonist such as dihyropyridine.

Methods and Compositions of Delivery

Improved methods and compositions for mucosal administration of Y2 receptor-binding peptide to mammalian subjects optimize Y2 receptor-binding peptide dosing schedules. The present invention provides mucosal delivery of Y2 receptor-binding peptide formulated with one or more mucosal delivery-enhancing agents wherein Y2 receptor-binding peptide dosage release is substantially normalized and/or sustained for an effective delivery period of Y2 receptor-binding peptide release ranges from approximately 0.1 to 2.0 hours; 0.4 to 1.5 hours; 0.7 to 1.5 hours; or 0.8 to 1.0 hours; following mucosal administration. The sustained release of Y2 receptor-binding peptide achieved may be facilitated by repeated administration of exogenous Y2 receptor-binding peptide utilizing methods and compositions of the present invention.

Compositions and Methods of Sustained Release

Improved compositions and methods for mucosal administration of Y2 receptor-binding peptide to mammalian subjects optimize Y2 receptor-binding peptide dosing schedules. The present invention provides improved mucosal (e.g., nasal) delivery and non-infused administration of a formulation comprising Y2 receptor-binding peptide in combination with one or more mucosal delivery-enhancing agents and an optional sustained release-enhancing agent or agents. Mucosal delivery-enhancing agents of the present invention yield an effective increase in delivery, e.g., an increase in the maximal plasma concentration ($C_{max}$) to enhance the therapeutic activity of mucosally-administered Y2 receptor-binding peptide. A second factor affecting therapeutic activity of Y2 receptor-binding peptide in the blood plasma and CNS is residence time (RT). Sustained release-enhancing agents, in combination with intranasal delivery-enhancing agents, increase $C_{max}$ and increase residence time (RT) of Y2 receptor-binding peptide. Polymeric delivery vehicles and other agents and methods of the present invention that yield sustained release-enhancing formulations, for example, polyethylene glycol (PEG), are disclosed herein. The present invention provides an improved Y2 receptor-binding peptide delivery method and dosage form for treatment of symptoms related to obesity, colon cancer, pancreatic cancer, or breast cancer in mammalian subjects.

Within the mucosal delivery formulations and methods of the invention, the Y2 receptor-binding peptide is frequently combined or coordinately administered with a suitable carrier or vehicle for mucosal delivery. As used herein, the term "carrier" means a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, can be found in the *U.S. Pharmacopeia National Formulary*, 1857–1859, (1990). Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other non toxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator. Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like. The amount of active ingredient that can be combined with the carrier materials to produce a single dosage form will vary depending upon the particular mode of administration.

Within the mucosal delivery compositions and methods of the invention, various delivery-enhancing agents are employed which enhance delivery of Y2 receptor-binding peptide into or across a mucosal surface. In this regard, delivery of Y2 receptor-binding peptide across the mucosal epithelium can occur "transcellularly" or "paracellularly". The extent to which these pathways contribute to the overall flux and bioavailability of the Y2 receptor-binding peptide depends upon the environment of the mucosa, the physicochemical properties the active agent, and on the properties of the mucosal epithelium. Paracellular transport involves only passive diffusion, whereas transcellular transport can occur by passive, facilitated or active processes. Generally, hydrophilic, passively transported, polar solutes diffuse through the paracellular route, while more lipophilic solutes use the transcellular route. Absorption and bioavailability (e.g., as reflected by a permeability coefficient or physiological assay), for diverse, passively and actively absorbed solutes, can be readily evaluated, in terms of both paracellular and transcellular delivery components, for any selected Y2 receptor-binding peptide within the invention. For passively absorbed drugs, the relative contribution of paracellular and transcellular pathways to drug transport depends upon the pKa, partition coefficient, molecular radius and charge of the drug, the pH of the luminal environment in which the drug is delivered, and the area of the absorbing surface. The paracellular route represents a relatively small fraction of accessible surface area of the nasal mucosal epithelium. In general terms, it has been reported that cell membranes occupy a mucosal surface area that is a thousand times greater than the area occupied by the paracellular spaces. Thus, the smaller accessible area, and the size- and charge-based discrimination against macromolecular permeation would suggest that the paracellular route would be a generally less favorable route than transcellular delivery for drug transport. Surprisingly, the methods and compositions of the invention provide for significantly enhanced transport of biotherapeutics into and across mucosal epithelia via the paracellular route. Therefore, the methods and compositions of the invention successfully target both paracellular and transcellular routes, alternatively or within a single method or composition.

As used herein, "mucosal delivery-enhancing agents" include agents which enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery, or at a selected target site of activity such as the bloodstream or central nervous system) of Y2 receptor-binding peptide or other biologically active compound(s). Enhancement of mucosal delivery can thus occur by any of a variety of mechanisms, for example by increasing the diffusion, transport, persistence or stability of Y2 receptor-binding peptide, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, and other mechanisms.

As used herein, a "mucosally effective amount of Y2 receptor-binding peptide" contemplates effective mucosal delivery of Y2 receptor-binding peptide to a target site for drug activity in the subject that may involve a variety of delivery or transfer routes. For example, a given active agent may find its way through clearances between cells of the mucosa and reach an adjacent vascular wall, while by another route the agent may, either passively or actively, be taken up into mucosal cells to act within the cells or be discharged or transported out of the cells to reach a secondary target site, such as the systemic circulation. The methods and compositions of the invention may promote the translocation of active agents along one or more such alternate routes, or may act directly on the mucosal tissue or proximal vascular tissue to promote absorption or penetration of the active agent(s). The promotion of absorption or penetration in this context is not limited to these mechanisms.

As used herein "peak concentration ($C_{max}$) of Y2 receptor-binding peptide in a blood plasma", "area under concentration vs. time curve (AUC) of Y2 receptor-binding peptide in a blood plasma", "time to maximal plasma concentration ($t_{max}$) of Y2 receptor-binding peptide in a blood plasma" are pharmacokinetic parameters known to one skilled in the art. Laursen et al., Eur. J. Endocrinology, 135: 309–315, 1996. The "concentration vs. time curve" measures the concentration of Y2 receptor-binding peptide in a blood serum of a subject vs. time after administration of a dosage of Y2 receptor-binding peptide to the subject either by intranasal, intramuscular, subcutaneous, or other parenteral route of administration. "$C_{max}$" is the maximum concentration of Y2 receptor-binding peptide in the blood serum of a subject following a single dosage of Y2 receptor-binding peptide to the subject. "$t_{max}$" is the time to reach maximum concentration of Y2 receptor-binding peptide in a blood serum of a subject following administration of a single dosage of Y2 receptor-binding peptide to the subject.

As used herein, "area under concentration vs. time curve (AUC) of Y2 receptor-binding peptide in a blood plasma" is calculated according to the linear trapezoidal rule and with addition of the residual areas. A decrease of 23% or an increase of 30% between two dosages would be detected with a probability of 90% (type II error $\beta=10\%$). The "delivery rate" or "rate of absorption" is estimated by comparison of the time ($t_{max}$) to reach the maximum concentration ($C_{max}$). Both $C_{max}$ and $t_{max}$ are analyzed using non-parametric methods. Comparisons of the pharmacokinetics of intramuscular, subcutaneous, intravenous and intranasal Y2 receptor-binding peptide administrations were performed by analysis of variance (ANOVA). For pair wise comparisons a Bonferroni-Holmes sequential procedure was used to evaluate significance. The dose-response relationship between the three nasal doses was estimated by regression analysis. $P<0.05$ was considered significant. Results are given as mean values +/−SEM.

While the mechanism of absorption promotion may vary with different mucosal delivery-enhancing agents of the invention, useful reagents in this context will not substantially adversely affect the mucosal tissue and will be selected according to the physicochemical characteristics of the particular Y2 receptor-binding peptide or other active or delivery-enhancing agent. In this context, delivery-enhancing agents that increase penetration or permeability of mucosal tissues will often result in some alteration of the protective permeability barrier of the mucosa. For such delivery-enhancing agents to be of value within the invention, it is generally desired that any significant changes in permeability of the mucosa be reversible within a time frame appropriate to the desired duration of drug delivery. Furthermore, there should be no substantial, cumulative toxicity, nor any permanent deleterious changes induced in the barrier properties of the mucosa with long-term use.

Within certain aspects of the invention, absorption-promoting agents for coordinate administration or combinatorial formulation with Y2 receptor-binding peptide of the invention are selected from small hydrophilic molecules, including but not limited to, dimethyl sulfoxide (DMSO), dimethylformamide, ethanol, propylene glycol, and the 2-pyrrolidones. Alternatively, long-chain amphipathic molecules, for example, deacylmethyl sulfoxide, azone, sodium lauryl sulfate, oleic acid, and the bile salts, may be employed to enhance mucosal penetration of the Y2 receptor-binding peptide. In additional aspects, surfactants (e.g., polysorbates) are employed as adjunct compounds, processing agents, or formulation additives to enhance intranasal delivery of the Y2 receptor-binding peptide. Agents such as DMSO, polyethylene glycol, and ethanol can, if present in sufficiently high concentrations in delivery environment (e.g., by pre-administration or incorporation in a therapeutic formulation), enter the aqueous phase of the mucosa and alter its solubilizing properties, thereby enhancing the partitioning of the Y2 receptor-binding peptide from the vehicle into the mucosa.

Additional mucosal delivery-enhancing agents that are useful within the coordinate administration and processing methods and combinatorial formulations of the invention include, but are not limited to, mixed micelles; enamines; nitric oxide donors (e.g., S-nitroso-N-acetyl-DL-penicillamine, NOR1, NOR4—which are preferably co-administered with an NO scavenger such as carboxy-PITO or doclofenac sodium); sodium salicylate; glycerol esters of acetoacetic acid (e.g., glyceryl-1,3-diacetoacetate or 1,2-isopropylideneglycerine-3-acetoacetate); and other release-diffusion or intra- or trans-epithelial penetration-promoting agents that are physiologically compatible for mucosal delivery. Other absorption-promoting agents are selected from a variety of carriers, bases and excipients that enhance mucosal delivery, stability, activity or trans-epithelial penetration of the Y2 receptor-binding peptide. These include, inter alia, α,β, or γ-cyclodextrins and derivatives and especially β-cyclodextrin derivatives (e.g., 2-hydroxypropyl-β-cyclodextrin and heptakis(2,6-di-O-methyl-β-cyclodextrin) methylated cyclodextrins (methyl-β-cyclodextrin and dimethyl-β-cyclodextrin), ethylated cyclodextrins, hydroxypropylated cyclodextrins, polymeric cyclodextrins. These compounds, optionally conjugated with one or more of the active ingredients and further optionally formulated in an oleaginous base, enhance bioavailability in the mucosal formulations of the invention. Yet additional absorption-enhancing agents adapted for mucosal delivery include medium-chain fatty acids, including mono- and diglycerides (e.g., sodium caprate—extracts of coconut oil, Capmul), and triglycerides (e.g., amylodextrin, Estaram 299, Miglyol 810).

Additional mucosal delivery-enhancing agents that are useful within the coordinate administration and processing methods and combinatorial formulations of the invention include, but are not limited to, mixed micelles; enamines; nitric oxide donors (e.g., S-nitroso-N-acetyl-DL-penicillamine, NOR1, NOR4—which are preferably co-administered with an NO scavenger such as carboxy-PITO or doclofenac sodium); sodium salicylate; glycerol esters of acetoacetic acid (e.g., glyceryl-1,3-diacetoacetate or 1,2-isopropylideneglycerine-3-acetoacetate); and other release-diffusion or intra- or trans-epithelial penetration-promoting agents that are physiologically compatible for mucosal delivery. Other absorption-promoting agents are selected from a variety of carriers, bases and excipients that enhance mucosal delivery, stability, activity or trans-epithelial penetration of the Y2 receptor-binding peptide. These include, inter alia, α, β, or γ-cyclodextrins and β-cyclodextrin derivatives (e.g., 2-hydroxypropyl-β-cyclodextrins and heptakis(2,6-di-O-methyl-β-cyclodextrin) methylated cyclodextrins (methyl-β-cyclodextrin and dimethyl-β-cyclodextrin), ethylated cyclodextrins, hydroxypropylated cyclodextrins, polymeric cyclodextrins. These compounds, optionally conjugated with one or more of the active ingredients and further optionally formulated in an oleaginous base, enhance bioavailability in the mucosal formulations of the invention. Yet additional absorption-enhancing agents adapted for mucosal delivery include medium-chain fatty acids, including mono- and diglycerides (e.g., sodium caprate—extracts of coconut oil, Capmul), and triglycerides (e.g., amylodextrin, Estaram 299, Miglyol 810).

The mucosal therapeutic and prophylactic compositions of the present invention may be supplemented with any suitable penetration-promoting agent that facilitates absorption, diffusion, or penetration of Y2 receptor-binding peptide across mucosal barriers. The penetration promoter may be any promoter that is pharmaceutically acceptable. Thus, in more detailed aspects of the invention compositions are provided that incorporate one or more penetration-promoting agents selected from sodium salicylate and salicylic acid derivatives (acetyl salicylate, choline salicylate, salicylamide, etc.); amino acids and salts thereof (e.g. monoaminocarboxylic acids such as glycine, alanine, phenylalanine, proline, hydroxyproline, etc.; hydroxyamino acids such as serine; acidic amino acids such as aspartic acid, glutamic acid, etc; and basic amino acids such as lysine etc—inclusive of their alkali metal or alkaline earth metal salts); and N-acetylamino acids (N-acetylalanine, N-acetylphenylalanine, N-acetylserine, N-acetylglycine, N-acetyllysine, N-acetylglutamic acid, N-acetylproline, N-acetylhydroxyproline, etc.) and their salts (alkali metal salts and alkaline earth metal salts). Also provided as penetration-promoting agents within the methods and compositions of the invention are substances which are generally used as emulsifiers (e.g. sodium oleyl phosphate, sodium lauryl phosphate, sodium lauryl sulfate, sodium myristyl sulfate, polyoxyethylene alkyl ethers, polyoxyethylene alkyl esters, etc.), caproic acid, lactic acid, malic acid and citric acid and alkali metal salts thereof, pyrrolidonecarboxylic acids, alkylpyrrolidonecarboxylic acid esters, N-alkylpyrrolidones, proline acyl esters, and the like.

Within various aspects of the invention, improved nasal mucosal delivery formulations and methods are provided that allow delivery of Y2 receptor-binding peptide and other therapeutic agents within the invention across mucosal barriers between administration and selected target sites. Certain formulations are specifically adapted for a selected target cell, tissue or organ, or even a particular disease state. In other aspects, formulations and methods provide for efficient, selective endo- or transcytosis of Y2 receptor-binding peptide specifically routed along a defined intracellular or intercellular pathway. Typically, the Y2 receptor-binding peptide is efficiently loaded at effective concentration levels in a carrier or other delivery vehicle, and is delivered and maintained in a stabilized form, e.g., at the nasal mucosa and/or during passage through intracellular compartments and membranes to a remote target site for drug action (e.g., the blood stream or a defined tissue, organ, or extracellular compartment). The Y2 receptor-binding peptide may be provided in a delivery vehicle or otherwise modified (e.g., in the form of a prodrug), wherein release or activation of the Y2 receptor-binding peptide is triggered by a physiological stimulus (e.g. pH change, lysosomal enzymes, etc.) Often, the Y2 receptor-binding peptide is pharmacologically inactive until it reaches its target site for activity. In most cases, the Y2 receptor-binding peptide and other formulation components are non-toxic and non-immunogenic. In this context, carriers and other formulation components are generally selected for their ability to be rapidly degraded and excreted under physiological conditions. At the same time, formulations are chemically and physically stable in dosage form for effective storage.

Peptide and Protein Analogs and Mimetics

Included within the definition of biologically active peptides and proteins for use within the invention are natural or synthetic, therapeutically or prophylactically active, peptides (comprised of two or more covalently linked amino acids), proteins, peptide or protein fragments, peptide or protein analogs, and chemically modified derivatives or salts of active peptides or proteins. A wide variety of useful analogs and mimetics of Y2 receptor-binding peptide are contemplated for use within the invention and can be produced and tested for biological activity according to known methods. Often, the peptides or proteins of Y2 receptor-binding peptide or other biologically active peptides or proteins for use within the invention are muteins that are readily obtainable by partial substitution, addition, or deletion of amino acids within a naturally occurring or native (e.g., wild-type, naturally occurring mutant, or allelic variant) peptide or protein sequence. Additionally, biologically active fragments of native peptides or proteins are included. Such mutant derivatives and fragments substantially retain the desired biological activity of the native peptide or proteins. In the case of peptides or proteins having carbohydrate chains, biologically active variants marked by alterations in these carbohydrate species are also included within the invention.

As used herein, the term "conservative amino acid substitution" refers to the general interchangeability of amino acid residues having similar side chains. For example, a commonly interchangeable group of amino acids having aliphatic side chains is alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Examples of conservative substitutions include the substitution of a non-polar (hydrophobic) residue such as isoleucine, valine, leucine or methionine for another. Likewise, the present invention contemplates the substitution of a polar (hydrophilic) residue such as between arginine and lysine, between glutamine and asparagine, and between threonine and serine. Additionally, the substitution of a basic residue such as lysine, arginine or histidine for another or the substitution of an acidic residue such as aspartic acid or glutamic acid for another is also contemplated. Exemplary conservative amino acids substitution groups are: valine-leucine-isoleucine, phenylalanine-tyrosine, lysine-arginine, alanine-valine, and asparagine-glutamine. By aligning a peptide or protein analog optimally with a corresponding native peptide or protein, and by using appropriate assays, e.g., adhesion protein or receptor binding assays, to determine a selected biological activity, one can readily identify operable peptide and protein analogs for use within the methods and compositions of the invention. Operable peptide and protein analogs are typically specifically immunoreactive with antibodies raised to the corresponding native peptide or protein.

An approach for stabilizing solid protein formulations of the invention is to increase the physical stability of purified, e.g., lyophilized, protein. This will inhibit aggregation via hydrophobic interactions as well as via covalent pathways that may increase as proteins unfold. Stabilizing formulations in this context often include polymer-based formulations, for example a biodegradable hydrogel formulation/delivery system. As noted above, the critical role of water in protein structure, function, and stability is well known. Typically, proteins are relatively stable in the solid state with bulk water removed. However, solid therapeutic protein formulations may become hydrated upon storage at elevated humidity or during delivery from a sustained release composition or device. The stability of proteins generally drops with increasing hydration. Water can also play a significant role in solid protein aggregation, for example, by increasing protein flexibility resulting in enhanced accessibility of reactive groups, by providing a mobile phase for reactants, and by serving as a reactant in several deleterious processes such as beta-elimination and hydrolysis.

Protein preparations containing between about 6% to 28% water are the most unstable. Below this level, the mobility of bound water and protein internal motions are low. Above this level, water mobility and protein motions approach those of full hydration. Up to a point, increased susceptibility toward solid-phase aggregation with increasing hydration has been observed in several systems. However, at higher water content, less aggregation is observed because of the dilution effect.

In accordance with these principles, an effective method for stabilizing peptides and proteins against solid-state aggregation for mucosal delivery is to control the water content in a solid formulation and maintain the water activity in the formulation at optimal levels. This level depends on the nature of the protein, but in general, proteins maintained below their "monolayer" water coverage will exhibit superior solid-state stability.

A variety of additives, diluents, bases and delivery vehicles are provided within the invention that effectively controls water content to enhance protein stability. These reagents and carrier materials effective as anti-aggregation agents in this sense include, for example, polymers of various functionalities, such as polyethylene glycol, dextran, diethylaminoethyl dextran, and carboxymethyl cellulose, which significantly increase the stability and reduce the solid-phase aggregation of peptides and proteins admixed therewith or linked thereto. In some instances, the activity or physical stability of proteins can also be enhanced by various additives to aqueous solutions of the peptide or protein drugs. For example, additives, such as polyols (including sugars), amino acids, proteins such as collagen and gelatin, and various salts may be used.

Certain additives, in particular sugars and other polyols, also impart significant physical stability to dry, e.g., lyophilized proteins. These additives can also be used within the invention to protect the proteins against aggregation not only during lyophilization but also during storage in the dry state. For example sucrose and Ficoll 70 (a polymer with sucrose units) exhibit significant protection against peptide or protein aggregation during solid-phase incubation under various conditions. These additives may also enhance the stability of solid proteins embedded within polymer matrices.

Yet additional additives, for example sucrose, stabilize proteins against solid-state aggregation in humid atmospheres at elevated temperatures, as may occur in certain sustained-release formulations of the invention. Proteins such as gelatin and collagen also serve as stabilizing or bulking agents to reduce denaturation and aggregation of unstable proteins in this context. These additives can be incorporated into polymeric melt processes and compositions within the invention. For example, polypeptide microparticles can be prepared by simply lyophilizing or spray drying a solution containing various stabilizing additives described above. Sustained release of unaggregated peptides and proteins can thereby be obtained over an extended period of time.

Various additional preparative components and methods, as well as specific formulation additives, are provided herein which yield formulations for mucosal delivery of aggregation-prone peptides and proteins, wherein the peptide or protein is stabilized in a substantially pure, unaggregated form using a solubilization agent. A range of components and additives are contemplated for use within these methods and formulations. Exemplary of these solubilization agents are cyclodextrins (CDs), which selectively bind hydrophobic side chains of polypeptides. These CDs have been found to bind to hydrophobic patches of proteins in a manner that significantly inhibits aggregation. This inhibition is selective with respect to both the CD and the protein involved. Such selective inhibition of protein aggregation provides additional advantages within the intranasal delivery methods and compositions of the invention. Additional agents for use in this context include CD dimers, trimers and tetramers with varying geometries controlled by the linkers that specifically block aggregation of peptides and protein. Yet solubilization agents and methods for incorporation within the invention involve the use of peptides and peptide mimetics to selectively block protein-protein interactions. In one aspect, the specific binding of hydrophobic side chains reported for CD multimers is extended to proteins via the use of peptides and peptide mimetics that similarly block protein aggregation. A wide range of suitable methods and anti-aggregation agents are available for incorporation within the compositions and procedures of the invention.

Charge Modifying and pH Control Agents and Methods

To improve the transport characteristics of biologically active agents (including Y2 receptor-binding peptide, other active peptides and proteins, and macromolecular and small molecule drugs) for enhanced delivery across hydrophobic mucosal membrane barriers, the invention also provides techniques and reagents for charge modification of selected biologically active agents or delivery-enhancing agents described herein. In this regard, the relative permeability of macromolecules is generally related to their partition coefficients. The degree of ionization of molecules, which is dependent on the $pK_a$ of the molecule and the pH at the mucosal membrane surface, also affects permeability of the molecules. Permeation and partitioning of biologically active agents, including Y2 receptor-binding peptide and analogs of the invention, for mucosal delivery may be facilitated by charge alteration or charge spreading of the active agent or permeabilizing agent, which is achieved, for example, by alteration of charged functional groups, by modifying the pH of the delivery vehicle or solution in which the active agent is delivered, or by coordinate administration of a charge- or pH-altering reagent with the active agent.

Consistent with these general teachings, mucosal delivery of charged macromolecular species, including Y2 receptor-binding peptide and other biologically active peptides and proteins, within the methods and compositions of the invention is substantially improved when the active agent is delivered to the mucosal surface in a substantially un-ionized, or neutral, electrical charge state.

Certain Y2 receptor-binding peptide and other biologically active peptide and protein components of mucosal formulations for use within the invention will be charge modified to yield an increase in the positive charge density of the peptide or protein. These modifications extend also to cationization of peptide and protein conjugates, carriers and other delivery forms disclosed herein. Cationization offers a convenient means of altering the biodistribution and transport properties of proteins and macromolecules within the invention. Cationization is undertaken in a manner that substantially preserves the biological activity of the active agent and limits potentially adverse side effects, including tissue damage and toxicity.

Degradative Enzyme Inhibitory Agents and Methods

Another excipient that may be included in a trans-mucosal preparation is a degradative enzyme inhibitor. Exemplary mucoadhesive polymer-enzyme inhibitor complexes that are useful within the mucosal delivery formulations and methods of the invention include, but are not limited to: Carboxymethylcellulose-pepstatin (with anti-pepsin activity); Poly(acrylic acid)-Bowman-Birk inhibitor (anti-chymotrypsin); Poly(acrylic acid)-chymostatin (anti-chymotrypsin); Poly(acrylic acid)-elastatinal (anti-elastase); Carboxymethylcellulose-elastatinal (anti-elastase); Polycarbophil—lastatinal (anti-elastase); Chitosan—antipain (anti-trypsin); Poly(acrylic acid)—bacitracin (anti-aminopeptidase N); Chitosan—EDTA (anti-aminopeptidase N, anti-carboxypeptidase A); Chitosan—EDTA—antipain (anti-trypsin, anti-chymotrypsin, anti-elastase). As described in further detail below, certain embodiments of the invention will optionally incorporate a novel chitosan derivative or chemically modified form of chitosan. One such novel derivative for use within the invention is denoted as a β-[1→4]-2-guanidino-2-deoxy-D-glucose polymer (poly-GuD).

Any inhibitor that inhibits the activity of an enzyme to protect the biologically active agent(s) may be usefully employed in the compositions and methods of the invention. Useful enzyme inhibitors for the protection of biologically active proteins and peptides include, for example, soybean trypsin inhibitor, pancreatic trypsin inhibitor, chymotrypsin inhibitor and trypsin and chrymotrypsin inhibitor isolated from potato (solanum tuberosum L.) tubers. A combination or mixtures of inhibitors may be employed. Additional inhibitors of proteolytic enzymes for use within the invention include ovomucoid-enzyme, gabaxate mesylate, alpha1-antitrypsin, aprotinin, amastatin, bestatin, puromycin, bacitracin, leupepsin, alpha2-macroglobulin, pepstatin and egg white or soybean trypsin inhibitor. These and other inhibitors can be used alone or in combination. The inhibitor(s) may be incorporated in or bound to a carrier, e.g., a hydrophilic polymer, coated on the surface of the dosage form which is to contact the nasal mucosa, or incorporated in the superficial phase of the surface, in combination with the biologically active agent or in a separately administered (e.g., pre-administered) formulation.

The amount of the inhibitor, e.g., of a proteolytic enzyme inhibitor that is optionally incorporated in the compositions of the invention will vary depending on (a) the properties of the specific inhibitor, (b) the number of functional groups present in the molecule (which may be reacted to introduce ethylenic unsaturation necessary for copolymerization with hydrogel forming monomers), and (c) the number of lectin groups, such as glycosides, which are present in the inhibitor molecule. It may also depend on the specific therapeutic agent that is intended to be administered. Generally speaking, a useful amount of an enzyme inhibitor is from about 0.1 mg/ml to about 50 mg/ml, often from about 0.2 mg/ml to about 25 mg/ml, and more commonly from about 0.5 mg/ml to 5 mg/ml of the of the formulation (i.e., a separate protease inhibitor formulation or combined formulation with the inhibitor and biologically active agent).

In the case of trypsin inhibition, suitable inhibitors may be selected from, e.g., aprotinin, BBI, soybean trypsin inhibitor, chicken ovomucoid, chicken ovoinhibitor, human pancreatic trypsin inhibitor, camostat mesilate, flavonoid inhibitors, antipain, leupeptin, p-aminobenzamidine, AEBSF, TLCK (tosyllysine chloromethylketone), APMSF, DFP, PMSF, and poly(acrylate) derivatives. In the case of chymotrypsin inhibition, suitable inhibitors may be selected from, e.g., aprotinin, BBI, soybean trypsin inhibitor, chymostatin, benzyloxycarbonyl-Pro-Phe-CHO, FK-448, chicken ovoinhibitor, sugar biphenylboronic acids complexes, DFP, PMSF, β-phenylpropionate, and poly(acrylate) derivatives. In the case of elastase inhibition, suitable inhibitors may be selected from, e.g., elastatinal, methoxysuccinyl-Ala-Ala-Pro-Val-chloromethylketone (MPCMK), BBI, soybean trypsin inhibitor, chicken ovoinhibitor, DFP, and PMSF.

Additional enzyme inhibitors for use within the invention are selected from a wide range of non-protein inhibitors that vary in their degree of potency and toxicity. As described in further detail below, immobilization of these adjunct agents to matrices or other delivery vehicles, or development of chemically modified analogues, may be readily implemented to reduce or even eliminate toxic effects, when they are encountered. Among this broad group of candidate enzyme inhibitors for use within the invention are organophosphorous inhibitors, such as diisopropylfluorophosphate (DFP) and phenylmethylsulfonyl fluoride (PMSF), which are potent, irreversible inhibitors of serine proteases (e.g., trypsin and chymotrypsin). The additional inhibition of acetylcholinesterase by these compounds makes them highly toxic in uncontrolled delivery settings. Another candidate inhibitor, 4-(2-Aminoethyl)-benzenesulfonyl fluoride (AEBSF), has an inhibitory activity comparable to DFP and PMSF, but it is markedly less toxic. (4-Aminophenyl)-methanesulfonyl fluoride hydrochloride (APMSF) is another potent inhibitor of trypsin, but is toxic in uncontrolled settings. In contrast to these inhibitors, 4-(4-isopropylpiperadinocarbonyl)phenyl 1,2,3,4,-tetrahydro-1-naphthoate methanesulphonate (FK-448) is a low toxic substance, representing a potent and specific inhibitor of chymotrypsin. Further representatives of this non-protein group of inhibitor candidates, and also exhibiting low toxic risk, are camostat mesilate (N,N'-dimethyl carbamoylmethyl-p-(p'-guanidinobenzoyloxy)phenylacetate methane-sulphonate).

Yet another type of enzyme inhibitory agent for use within the methods and compositions of the invention are amino acids and modified amino acids that interfere with enzymatic degradation of specific therapeutic compounds. For use in this context, amino acids and modified amino acids are substantially non-toxic and can be produced at a low cost. However, due to their low molecular size and good solubility, they are readily diluted and absorbed in mucosal environments. Nevertheless, under proper conditions, amino acids can act as reversible, competitive inhibitors of protease enzymes. Certain modified amino acids can display a much stronger inhibitory activity. A desired modified amino acid in this context is known as a 'transition-state' inhibitor. The strong inhibitory activity of these compounds is based on their structural similarity to a substrate in its transition-state geometry, while they are generally selected to have a much higher affinity for the active site of an enzyme than the substrate itself. Transition-state inhibitors are reversible, competitive inhibitors. Examples of this type of inhibitor are α-aminoboronic acid derivatives, such as boro-leucine, boro-valine and boro-alanine. The boron atom in these derivatives can form a tetrahedral boronate ion that is believed to resemble the transition state of peptides during their hydrolysis by aminopeptidases. These amino acid derivatives are potent and reversible inhibitors of aminopeptidases and it is reported that boro-leucine is more than 100-times more effective in enzyme inhibition than bestatin and more than 1000-times more effective than puromycin. Another modified amino acid for which a strong protease inhibitory activity has been reported is N-acetylcysteine, which inhibits enzymatic activity of aminopeptidase N. This adjunct agent also displays mucolytic properties that can be employed within the methods and compositions of the invention to reduce the effects of the mucus diffusion barrier.

Still other useful enzyme inhibitors for use within the coordinate administration methods and combinatorial formulations of the invention may be selected from peptides and modified peptide enzyme inhibitors. An important representative of this class of inhibitors is the cyclic dodecapeptide, bacitracin, obtained from *Bacillus licheniformis*. In addition to these types of peptides, certain dipeptides and tripeptides display weak, non-specific inhibitory activity towards some protease. By analogy with amino acids, their inhibitory activity can be improved by chemical modifications. For example, phosphinic acid dipeptide analogues are also 'transition-state' inhibitors with a strong inhibitory activity towards aminopeptidases. They have reportedly been used to stabilize nasally administered leucine enkephalin. Another example of a transition-state analogue is the modified pentapeptide pepstatin, which is a very potent inhibitor of pepsin. Structural analysis of pepstatin, by testing the inhibitory activity of several synthetic analogues, demonstrated the major structure-function characteristics of the molecule responsible for the inhibitory activity. Another special type of modified peptide includes inhibitors with a terminally located aldehyde function in their structure. For example, the sequence benzyloxycarbonyl-Pro-Phe-CHO, which fulfills the known primary and secondary specificity requirements of chymotrypsin, has been found to be a potent reversible inhibitor of this target proteinase. The chemical structures of further inhibitors with a terminally located aldehyde function, e.g. antipain, leupeptin, chymostatin and elastatinal, are also known in the art, as are the structures of other known, reversible, modified peptide inhibitors, such as phosphoramidon, bestatin, puromycin and amastatin.

Due to their comparably high molecular mass, polypeptide protease inhibitors are more amenable than smaller compounds to concentrated delivery in a drug-carrier matrix. Additional agents for protease inhibition within the formulations and methods of the invention involve the use of complexing agents. These agents mediate enzyme inhibition by depriving the intranasal environment (or preparative or therapeutic composition) of divalent cations, which are co-factors for many proteases. For instance, the complexing agents EDTA and DTPA as coordinately administered or combinatorially formulated adjunct agents, in suitable concentration, will be sufficient to inhibit selected proteases to thereby enhance intranasal delivery of biologically active agents according to the invention. Further representatives of this class of inhibitory agents are EGTA, 1,10-phenanthroline and hydroxychinoline. In addition, due to their propensity to chelate divalent cations, these and other complexing agents are useful within the invention as direct, absorption-promoting agents.

As noted in more detail elsewhere herein, it is also contemplated to use various polymers, particularly mucoadhesive polymers, as enzyme inhibiting agents within the coordinate administration, multi-processing and/or combinatorial formulation methods and compositions of the invention. For example, poly(acrylate) derivatives, such as poly (acrylic acid) and polycarbophil, can affect the activity of various proteases, including trypsin, chymotrypsin. The inhibitory effect of these polymers may also be based on the complexation of divalent cations such as $Ca^{2+}$ and $Zn^{2+}$. It is further contemplated that these polymers may serve as conjugate partners or carriers for additional enzyme inhibitory agents, as described above. For example, a chitosan-EDTA conjugate has been developed and is useful within the invention that exhibits a strong inhibitory effect towards the enzymatic activity of zinc-dependent proteases. The mucoadhesive properties of polymers following covalent attachment of other enzyme inhibitors in this context are not expected to be substantially compromised, nor is the general utility of such polymers as a delivery vehicle for biologically active agents within the invention expected to be diminished. On the contrary, the reduced distance between the delivery vehicle and mucosal surface afforded by the mucoadhesive mechanism will minimize presystemic metabolism of the active agent, while the covalently bound enzyme inhibitors remain concentrated at the site of drug delivery, minimizing undesired dilution effects of inhibitors as well as toxic and other side effects caused thereby. In this manner, the effective amount of a coordinately administered enzyme inhibitor can be reduced due to the exclusion of dilution effects.

Exemplary mucoadhesive polymer-enzyme inhibitor complexes that are useful within the mucosal formulations and methods of the invention include, but are not limited to: Carboxymethylcellulose-pepstatin (with anti-pepsin activity); Poly(acrylic acid)-Bowman-Birk inhibitor (anti-chymotrypsin); Poly(acrylic acid)-chymostatin (anti-chymotrypsin); Poly(acrylic acid)-elastatinal (anti-elastase); Carboxymethylcellulose-elastatinal (anti-elastase); Polycarbophil—elastatinal (anti-elastase); Chitosan—antipain (anti-trypsin); Poly(acrylic acid)—bacitracin (anti-aminopeptidase N); Chitosan—EDTA (anti-aminopeptidase N, anti-carboxypeptidase A); Chitosan—EDTA—antipain (anti-trypsin, anti-chymotrypsin, anti-elastase).

Mucolytic and Mucus-Clearing Agents and Methods

Effective delivery of biotherapeutic agents via intranasal administration must take into account the decreased drug transport rate across the protective mucus lining of the nasal mucosa, in addition to drug loss due to binding to glycoproteins of the mucus layer. Normal mucus is a viscoelastic, gel-like substance consisting of water, electrolytes, mucins, macromolecules, and sloughed epithelial cells. It serves primarily as a cytoprotective and lubricative covering for the underlying mucosal tissues. Mucus is secreted by randomly distributed secretory cells located in the nasal epithelium and in other mucosal epithelia. The structural unit of mucus is mucin. This glycoprotein is mainly responsible for the viscoelastic nature of mucus, although other macromolecules may also contribute to this property. In airway mucus, such macromolecules include locally produced secretory IgA, IgM, IgE, lysozyme, and bronchotransferrin, which also play an important role in host defense mechanisms.

The coordinate administration methods of the instant invention optionally incorporate effective mucolytic or mucus-clearing agents, which serve to degrade, thin or clear mucus from intranasal mucosal surfaces to facilitate absorption of intranasally administered biotherapeutic agents. Within these methods, a mucolytic or mucus-clearing agent is coordinately administered as an adjunct compound to enhance intranasal delivery of the biologically active agent. Alternatively, an effective amount of a mucolytic or mucus-clearing agent is incorporated as a processing agent within a multi-processing method of the invention, or as an additive within a combinatorial formulation of the invention, to provide an improved formulation that enhances intranasal delivery of biotherapeutic compounds by reducing the barrier effects of intranasal mucus.

A variety of mucolytic or mucus-clearing agents are available for incorporation within the methods and compositions of the invention. Based on their mechanisms of action, mucolytic and mucus clearing agents can often be classified into the following groups: proteases (e.g., pronase, papain) that cleave the protein core of mucin glycoproteins; sulfhydryl compounds that split mucoprotein disulfide linkages; and detergents (e.g., Triton X-100, Tween 20) that break non-covalent bonds within the mucus. Additional compounds in this context include, but are not limited to, bile salts and surfactants, for example, sodium deoxycholate, sodium taurodeoxycholate, sodium glycocholate, and lysophosphatidylcholine.

The effectiveness of bile salts in causing structural breakdown of mucus is in the order deoxycholate>taurocholate>glycocholate. Other effective agents that reduce mucus viscosity or adhesion to enhance intranasal delivery according to the methods of the invention include, e.g., short-chain fatty acids, and mucolytic agents that work by chelation, such as N-acylcollagen peptides, bile acids, and saponins (the latter function in part by chelating $Ca^{2+}$ and/or $Mg^{2+}$ which play an important role in maintaining mucus layer structure).

Additional mucolytic agents for use within the methods and compositions of the invention include N-acetyl-L-cysteine (ACS), a potent mucolytic agent that reduces both the viscosity and adherence of bronchopulmonary mucus and is reported to modestly increase nasal bioavailability of human growth hormone in anesthetized rats (from 7.5 to 12.2%). These and other mucolytic or mucus-clearing agents are contacted with the nasal mucosa, typically in a concentration range of about 0.2 to 20 mM, coordinately with administration of the biologically active agent, to reduce the polar viscosity and/or elasticity of intranasal mucus.

Still other mucolytic or mucus-clearing agents may be selected from a range of glycosidase enzymes, which are able to cleave glycosidic bonds within the mucus glycoprotein. α-amylase and β-amylase are representative of this class of enzymes, although their mucolytic effect may be limited. In contrast, bacterial glycosidases which allow these microorganisms to permeate mucus layers of their hosts.

For combinatorial use with most biologically active agents within the invention, including peptide and protein therapeutics, non-ionogenic detergents are generally also useful as mucolytic or mucus-clearing agents. These agents typically will not modify or substantially impair the activity of therapeutic polypeptides.

Ciliostatic Agents and Methods

Because the self-cleaning capacity of certain mucosal tissues (e.g., nasal mucosal tissues) by mucociliary clearance is necessary as a protective function (e.g., to remove dust, allergens, and bacteria), it has been generally considered that this function should not be substantially impaired by mucosal medications. Mucociliary transport in the respiratory tract is a particularly important defense mechanism against infections. To achieve this function, ciliary beating in the nasal and airway passages moves a layer of mucus along the mucosa to removing inhaled particles and microorganisms.

Ciliostatic agents find use within the methods and compositions of the invention to increase the residence time of mucosally (e.g., intranasally) administered Y2 receptor-binding peptide, analogs and mimetics, and other biologically active agents disclosed herein. In particular, the delivery these agents within the methods and compositions of the invention is significantly enhanced in certain aspects by the coordinate administration or combinatorial formulation of one or more ciliostatic agents that function to reversibly inhibit ciliary activity of mucosal cells, to provide for a temporary, reversible increase in the residence time of the mucosally administered active agent(s). For use within these aspects of the invention, the foregoing ciliostatic factors, either specific or indirect in their activity, are all candidates for successful employment as ciliostatic agents in appropriate amounts (depending on concentration, duration and mode of delivery) such that they yield a transient (i.e., reversible) reduction or cessation of mucociliary clearance at a mucosal site of administration to enhance delivery of Y2 receptor-binding peptide, analogs and mimetics, and other biologically active agents disclosed herein, without unacceptable adverse side effects.

Within more detailed aspects, a specific ciliostatic factor is employed in a combined formulation or coordinate administration protocol with one or more Y2 receptor-binding peptide proteins, analogs and mimetics, and/or other biologically active agents disclosed herein. Various bacterial ciliostatic factors isolated and characterized in the literature may be employed within these embodiments of the invention. Ciliostatic factors from the bacterium *Pseudomonas aeruginosa* include a phenazine derivative, a pyo compound (2-alkyl-4-hydroxyquinolines), and a rhamnolipid (also known as a hemolysin). The pyo compound produced ciliostasis at concentrations of 50 μg/ml and without obvious ultrastructural lesions. The phenazine derivative also inhibited ciliary motility but caused some membrane disruption, although at substantially greater concentrations of 400 μg/ml. Limited exposure of tracheal explants to the rhamnolipid resulted in ciliostasis, which was associated with altered ciliary membranes. More extensive exposure to rhamnolipid was associated with removal of dynein arms from axonemes.

Surface Active Agents and Methods

Within more detailed aspects of the invention, one or more surface active membrane penetration-enhancing agents may be employed within a mucosal delivery method or formulation of the invention to enhance mucosal delivery of Y2 receptor-binding peptide proteins, analogs and mimetics, and other biologically active agents disclosed herein. Membrane penetration enhancing agents in this context can be selected from: (i) a surfactant, (ii) a bile salt, (iii) a phospholipid additive, mixed micelle, liposome, or carrier, (iv) an alcohol, (v) an enamine, (vi) an NO donor compound, (vii) a long-chain amphipathic molecule (viii) a small hydrophobic penetration enhancer; (ix) sodium or a salicylic acid derivative; (x) a glycerol ester of acetoacetic acid (xi) a cyclodextrin or beta-cyclodextrin derivative, (xii) a medium-chain fatty acid, (xiii) a chelating agent, (xiv) an amino acid or salt thereof, (xv) an N-acetylamino acid or salt thereof, (xvi) an enzyme degradative to a selected membrane component, (xvii) an inhibitor of fatty acid synthesis, or (xviii) an inhibitor of cholesterol synthesis; or (xix) any combination of the membrane penetration enhancing agents recited in (i)–(xix). A surface active agent includes any chemical or group of chemicals that lowers the normal surface tension of pure water from about 60 dynes-cm2 to from about 50 to about 0 dynes-cm2.

Certain surface-active agents are readily incorporated within the mucosal delivery formulations and methods of the invention as mucosal absorption enhancing agents. These agents, which may be coordinately administered or combinatorially formulated with Y2 receptor-binding peptide proteins, analogs and mimetics, and other biologically active agents disclosed herein, may be selected from a broad assemblage of known surfactants. Surfactants, which generally fall into three classes: (1) nonionic polyoxyethylene ethers; (2) bile salts such as sodium glycocholate (SGC) and deoxycholate (DOC); and (3) derivatives of fusidic acid such as sodium taurodihydrofusidate (STDHF). The mechanisms of action of these various classes of surface-active agents typically include solubilization of the biologically active agent. For proteins and peptides which often form aggregates, the surface active properties of these absorption promoters can allow interactions with proteins such that smaller units such as surfactant coated monomers may be more readily maintained in solution. Examples of other surface-active agents are L-α-Phosphatidylcholine Didecanoyl (DDPC), polysorbate 80, and polysorbate 20. These monomers are presumably more transportable units than aggregates. A second potential mechanism is the protection of the peptide or protein from proteolytic degradation by proteases in the mucosal environment. Both bile salts and some fusidic acid derivatives reportedly inhibit proteolytic degradation of proteins by nasal homogenates at concentrations less than or equivalent to those required to enhance protein absorption. This protease inhibition may be especially important for peptides with short biological half-lives.

Degradation Enzymes and Inhibitors of Fatty Acid and Cholesterol Synthesis

In related aspects of the invention, Y2 receptor-binding peptide proteins, analogs and mimetics, and other biologically active agents for mucosal administration are formulated or coordinately administered with a penetration enhancing agent selected from a degradation enzyme, or a metabolic stimulatory agent or inhibitor of synthesis of fatty acids, sterols or other selected epithelial barrier components, U.S. Pat. No. 6,190,894. For example, degradative enzymes such as phospholipase, hyaluronidase, neuraminidase, and chondroitinase may be employed to enhance mucosal penetration of Y2 receptor-binding peptide proteins, analogs and mimetics, and other biologically active agent without causing irreversible damage to the mucosal barrier. In one embodiment, chondroitinase is employed within a method or composition as provided herein to alter glycoprotein or glycolipid constituents of the permeability barrier of the mucosa, thereby enhancing mucosal absorption of Y2 receptor-binding peptide proteins, analogs and mimetics, and other biologically active agents disclosed herein.

With regard to inhibitors of synthesis of mucosal barrier constituents, it is noted that free fatty acids account for 20–25% of epithelial lipids by weight. Two rate-limiting enzymes in the biosynthesis of free fatty acids are acetyl CoA carboxylase and fatty acid synthetase. Through a series of steps, free fatty acids are metabolized into phospholipids. Thus, inhibitors of free fatty acid synthesis and metabolism for use within the methods and compositions of the invention include, but are not limited to, inhibitors of acetyl CoA carboxylase such as 5-tetradecyloxy-2-furancarboxylic acid (TOFA); inhibitors of fatty acid synthetase; inhibitors of phospholipase A such as gomisin A, 2-(p-amylcinnamyl) amino-4-chlorobenzoic acid, bromophenacyl bromide, monoalide, 7,7-dimethyl-5,8-eicosadienoic acid, nicergoline, cepharanthine, nicardipine, quercetin, dibutyryl-cyclic AMP, R-24571, N-oleoylethanolamine, N-(7-nitro-2,1, 3-benzoxadiazol-4-yl)-phosphostidyl serine, cyclosporine A, topical anesthetics, including dibucaine, prenylamine, retinoids, such as all-trans and 13-cis-retinoic acid, W-7, trifluoperazine, R-24571 (calmidazolium), 1-hexadocyl-3-trifluoroethyl glycero-sn-2-phosphomenthol (MJ33); calcium channel blockers including nicardipine, verapamil, diltiazem, nifedipine, and nimodipine; antimalarials including quinacrine, mepacrine, chloroquine and hydroxychloroquine; beta blockers including propanalol and labetalol; calmodulin antagonists; EGTA; thimersol; glucocorticosteroids including dexamethasone and prednisolone; and non-steroidal antiinflammatory agents including indomethacin and naproxen.

Free sterols, primarily cholesterol, account for 20–25% of the epithelial lipids by weight. The rate limiting enzyme in the biosynthesis of cholesterol is 3-hydroxy-3-methylglutaryl (HMG) CoA reductase. Inhibitors of cholesterol synthesis for use within the methods and compositions of the invention include, but are not limited to, competitive inhibitors of (HMG) CoA reductase, such as simvastatin, lovastatin, fluindostatin (fluvastatin), pravastatin, mevastatin, as well as other HMG CoA reductase inhibitors, such as cholesterol oleate, cholesterol sulfate and phosphate, and oxygenated sterols, such as 25-OH— and 26-OH— cholesterol; inhibitors of squalene synthetase; inhibitors of squalene epoxidase; inhibitors of DELTA7 or DELTA24 reductases such as 22,25-diazacholesterol, 20,25-diazacholestenol, AY9944, and triparanol.

Each of the inhibitors of fatty acid synthesis or the sterol synthesis inhibitors may be coordinately administered or combinatorially formulated with one or more Y2 receptor-binding peptide proteins, analogs and mimetics, and other biologically active agents disclosed herein to achieve enhanced epithelial penetration of the active agent(s). An effective concentration range for the sterol inhibitor in a therapeutic or adjunct formulation for mucosal delivery is generally from about 0.0001% to about 20% by weight of the total, more typically from about 0.01% to about 5%.

Nitric Oxide Donor Agents and Methods

Within other related aspects of the invention, a nitric oxide (NO) donor is selected as a membrane penetration-enhancing agent to enhance mucosal delivery of one or more Y2 receptor-binding peptide proteins, analogs and mimetics, and other biologically active agents disclosed herein. Various NO donors are known in the art and are useful in effective concentrations within the methods and formulations of the invention. Exemplary NO donors include, but are not limited to, nitroglycerine, nitroprusside, NOC5 [3-(2-hydroxy-1-(methyl-ethyl)-2-nitrosohydrazino)-1-propanamine], NOC12 [N-ethyl-2-(1-ethyl-hydroxy-2-nitrosohydrazino)-ethanamine], SNAP [S-nitroso-N-acetyl-DL-penicillamine], NOR1 and NOR4. Within the methods and compositions of the invention, an effective amount of a selected NO donor is coordinately administered or combinatorially formulated with one or more Y2 receptor-binding peptide proteins, analogs and mimetics, and/or other biologically active agents disclosed herein, into or through the mucosal epithelium.

Agents for Modulating Epithelial Junction Structure and/or Physiology

The present invention provides pharmaceutical composition that contains one or more Y2 receptor-binding peptide proteins, analogs or mimetics, and/or other biologically active agents in combination with mucosal delivery enhancing agents disclosed herein formulated in a pharmaceutical preparation for mucosal delivery.

The permeabilizing agent reversibly enhances mucosal epithelial paracellular transport, typically by modulating epithelial junctional structure and/or physiology at a mucosal epithelial surface in the subject. This effect typically involves inhibition by the permeabilizing agent of homotypic or heterotypic binding between epithelial membrane adhesive proteins of neighboring epithelial cells. Target proteins for this blockade of homotypic or heterotypic binding can be selected from various related junctional adhesion molecules (JAMs), occludins, or claudins. Examples of this are antibodies, antibody fragments or single-chain antibodies that bind to the extracellular domains of these proteins.

In yet additional detailed embodiments, the invention provides permeabilizing peptides and peptide analogs and mimetics for enhancing mucosal epithelial paracellular transport. The subject peptides and peptide analogs and mimetics typically work within the compositions and methods of the invention by modulating epithelial junctional structure and/or physiology in a mammalian subject. In certain embodiments, the peptides and peptide analogs and mimetics effectively inhibit homotypic and/or heterotypic binding of an epithelial membrane adhesive protein selected from a junctional adhesion molecule (JAM), occludin, or claudin.

One such agent that has been extensively studied is the bacterial toxin from Vibrio cholerae known as the "zonula occludens toxin" (ZOT). This toxin mediates increased intestinal mucosal permeability and causes disease symptoms including diarrhea in infected subjects. Fasano et al, *Proc. Nat. Acad. Sci., U.S.A.,* 8:5242–5246 (1991). When tested on rabbit ileal mucosa, ZOT increased the intestinal permeability by modulating the structure of intercellular tight junctions. More recently, it has been found that ZOT is capable of reversibly opening tight junctions in the intestinal mucosa. It has also been reported that ZOT is capable of reversibly opening tight junctions in the nasal mucosa. U.S. Pat No. 5,908,825.

Within the methods and compositions of the invention, ZOT, as well as various analogs and mimetics of ZOT that function as agonists or antagonists of ZOT activity, are useful for enhancing intranasal delivery of biologically active agents—by increasing paracellular absorption into and across the nasal mucosa. In this context, ZOT typically acts by causing a structural reorganization of tight junctions marked by altered localization of the junctional protein ZO1. Within these aspects of the invention, ZOT is coordinately administered or combinatorially formulated with the biologically active agent in an effective amount to yield significantly enhanced absorption of the active agent, by reversibly increasing nasal mucosal permeability without substantial adverse side effects Vasodilator Agents and Methods Yet another class of absorption-promoting agents that shows beneficial utility within the coordinate administration and combinatorial formulation methods and compositions of the invention are vasoactive compounds, more specifically vasodilators. These compounds function within the invention to modulate the structure and physiology of the submucosal vasculature, increasing the transport rate of Y2 receptor-binding peptide, analogs and mimetics, and other biologically active agents into or through the mucosal epithelium and/or to specific target tissues or compartments (e.g., the systemic circulation or central nervous system.).

Vasodilator agents for use within the invention typically cause submucosal blood vessel relaxation by either a decrease in cytoplasmic calcium, an increase in nitric oxide (NO) or by inhibiting myosin light chain kinase. They are generally divided into 9 classes: calcium antagonists, potassium channel openers, ACE inhibitors, angiotensin-II receptor antagonists, α-adrenergic and imidazole receptor antagonists, β1-adrenergic agonists, phosphodiesterase inhibitors, eicosanoids and NO donors.

Despite chemical differences, the pharmacokinetic properties of calcium antagonists are similar. Absorption into the systemic circulation is high, and these agents therefore undergo considerable first-pass metabolism by the liver, resulting in individual variation in pharmacokinetics. Except for the newer drugs of the dihydropyridine type (amlodipine, felodipine, isradipine, nilvadipine, nisoldipine and nitrendipine), the half-life of calcium antagonists is short. Therefore, to maintain an effective drug concentration for many of these may require delivery by multiple dosing, or controlled release formulations, as described elsewhere herein. Treatment with the potassium channel opener minoxidil may also be limited in manner and level of administration due to potential adverse side effects.

ACE inhibitors prevent conversion of angiotensin-I to angiotensin-II, and are most effective when renin production is increased. Since ACE is identical to kininase-II, which inactivates the potent endogenous vasodilator bradykinin, ACE inhibition causes a reduction in bradykinin degradation. ACE inhibitors provide the added advantage of cardioprotective and cardioreparative effects, by preventing and reversing cardiac fibrosis and ventricular hypertrophy in animal models. The predominant elimination pathway of most ACE inhibitors is via renal excretion. Therefore, renal impairment is associated with reduced elimination and a dosage reduction of 25 to 50% is recommended in patients with moderate to severe renal impairment.

With regard to NO donors, these compounds are particularly useful within the invention for their additional effects on mucosal permeability. In addition to the above-noted NO donors, complexes of NO with nucleophiles called NO/nucleophiles, or NONOates, spontaneously and nonenzymatically release NO when dissolved in aqueous solution at physiologic pH. In contrast, nitro vasodilators such as nitroglycerin require specific enzyme activity for NO release. NONOates release NO with a defined stoichiometry and at predictable rates ranging from <3 minutes for diethylamine/NO to approximately 20 hours for diethylenetriamine/NO (DETANO).

Within certain methods and compositions of the invention, a selected vasodilator agent is coordinately administered (e.g., systemically or intranasally, simultaneously or in combinatorially effective temporal association) or combinatorially formulated with one or more Y2 receptor-binding peptide, analogs and mimetics, and other biologically active agent(s) in an amount effective to enhance the mucosal absorption of the active agent(s) to reach a target tissue or compartment in the subject (e.g., the liver, hepatic portal vein, CNS tissue or fluid, or blood plasma).

Selective Transport-Enhancing Agents and Methods

The compositions and delivery methods of the invention optionally incorporate a selective transport-enhancing agent that facilitates transport of one or more biologically active agents. These transport-enhancing agents may be employed in a combinatorial formulation or coordinate administration protocol with one or more of the Y2 receptor-binding peptide proteins, analogs and mimetics disclosed herein, to coordinately enhance delivery of one or more additional biologically active agent(s) across mucosal transport barriers, to enhance mucosal delivery of the active agent(s) to reach a target tissue or compartment in the subject (e.g., the mucosal epithelium, liver, CNS tissue or fluid, or blood plasma). Alternatively, the transport-enhancing agents may be employed in a combinatorial formulation or coordinate administration protocol to directly enhance mucosal delivery of one or more of the Y2 receptor-binding peptide proteins, analogs and mimetics, with or without enhanced delivery of an additional biologically active agent.

Exemplary selective transport-enhancing agents for use within this aspect of the invention include, but are not limited to, glycosides, sugar-containing molecules, and binding agents such as lectin binding agents, which are known to interact specifically with epithelial transport barrier components. For example, specific "bioadhesive" ligands, including various plant and bacterial lectins, which bind to cell surface sugar moieties by receptor-mediated interactions can be employed as carriers or conjugated transport mediators for enhancing mucosal, e.g., nasal delivery of biologically active agents within the invention. Certain bioadhesive ligands for use within the invention will mediate transmission of biological signals to epithelial target cells that trigger selective uptake of the adhesive ligand by specialized cellular transport processes (endocytosis or transcytosis). These transport mediators can therefore be employed as a "carrier system" to stimulate or direct selective uptake of one or more Y2 receptor-binding peptide proteins, analogs and mimetics, and other biologically active agent(s) into and/or through mucosal epithelia. These and other selective transport-enhancing agents significantly enhance mucosal delivery of macromolecular biopharmaceuticals (particularly peptides, proteins, oligonucleotides and polynucleotide vectors) within the invention. Lectins are plant proteins that bind to specific sugars found on the surface of glycoproteins and glycolipids of eukaryotic cells. Concentrated solutions of lectins have a 'mucotractive' effect, and various studies have demonstrated rapid receptor mediated endocytocis (RME) of lectins and lectin conjugates (e.g., concanavalin A conjugated with colloidal gold particles) across mucosal surfaces. Additional studies have reported that the uptake mechanisms for lectins can be utilized for intestinal drug targeting in vivo. In certain of these studies, polystyrene nanoparticles (500 nm) were covalently coupled to tomato lectin and reported yielded improved systemic uptake after oral administration to rats.

In addition to plant lectins, microbial adhesion and invasion factors provide a rich source of candidates for use as adhesive/selective transport carriers within the mucosal delivery methods and compositions of the invention. Two components are necessary for bacterial adherence processes, a bacterial 'adhesin' (adherence or colonization factor) and a receptor on the host cell surface. Bacteria causing mucosal infections need to penetrate the mucus layer before attaching themselves to the epithelial surface. This attachment is usually mediated by bacterial fimbriae or pilus structures, although other cell surface components may also take part in the process. Adherent bacteria colonize mucosal epithelia by multiplication and initiation of a series of biochemical reactions inside the target cell through signal transduction mechanisms (with or without the help of toxins). Associated with these invasive mechanisms, a wide diversity of bioadhesive proteins (e.g., invasin, internalin) originally produced by various bacteria and viruses are known. These allow for extracellular attachment of such microorganisms with an impressive selectivity for host species and even particular target tissues. Signals transmitted by such receptor-ligand interactions trigger the transport of intact, living microorganisms into, and eventually through, epithelial cells by endo- and transcytotic processes. Such naturally occurring phenomena may be harnessed (e.g., by complexing biologically active agents such as Y2 receptor-binding peptide with an adhesin) according to the teachings herein for enhanced delivery of biologically active compounds into or across mucosal epithelia and/or to other designated target sites of drug action.

Various bacterial and plant toxins that bind epithelial surfaces in a specific, lectin-like manner are also useful within the methods and compositions of the invention. For example, diphtheria toxin (DT) enters host cells rapidly by RME. Likewise, the B subunit of the *E. coli* heat labile toxin binds to the brush border of intestinal epithelial cells in a highly specific, lectin-like manner. Uptake of this toxin and transcytosis to the basolateral side of the enterocytes has been reported in vivo and in vitro. Other researches have expressed the transmembrane domain of diphtheria toxin in *E. coli* as a maltose-binding fusion protein and coupled it chemically to high-Mw poly-L-lysine. The resulting complex was successfully used to mediate internalization of a reporter gene in vitro. In addition to these examples, *Staphylococcus aureus* produces a set of proteins (e.g., staphylococcal enterotoxin A (SEA), SEB, toxic shock syndrome toxin 1 (TSST-1) which act both as superantigens and toxins.

Studies relating to these proteins have reported dose-dependent, facilitated transcytosis of SEB and TSST-I in Caco-2 cells.

Viral haemagglutinins comprise another type of transport agent to facilitate mucosal delivery of biologically active agents within the methods and compositions of the invention. The initial step in many viral infections is the binding of surface proteins (haemagglutinins) to mucosal cells. These binding proteins have been identified for most viruses, including rotaviruses, varicella zoster virus, semliki forest virus, adenoviruses, potato leafroll virus, and reovirus. These and other exemplary viral hemagglutinins can be employed in a combinatorial formulation (e.g., a mixture or conjugate formulation) or coordinate administration protocol with one or more of the Y2 receptor-binding peptide, analogs and mimetics disclosed herein, to coordinately enhance mucosal delivery of one or more additional biologically active agent(s). Alternatively, viral hemagglutinins can be employed in a combinatorial formulation or coordinate administration protocol to directly enhance mucosal delivery of one or more of the Y2 receptor-binding peptide proteins, analogs and mimetics, with or without enhanced delivery of an additional biologically active agent.

A variety of endogenous, selective transport-mediating factors are also available for use within the invention. Mammalian cells have developed an assortment of mechanisms to facilitate the internalization of specific substrates and target these to defined compartments. Collectively, these processes of membrane deformations are termed 'endocytosis' and comprise phagocytosis, pinocytosis, receptor-mediated endocytosis (clathrin-mediated RME), and potocytosis (non-clathrin-mediated RME). RME is a highly specific cellular biologic process by which, as its name implies, various ligands bind to cell surface receptors and are subsequently internalized and trafficked within the cell. In many cells the process of endocytosis is so active that the entire membrane surface is internalized and replaced in less than a half hour. Two classes of receptors are proposed based on their orientation in the cell membrane; the amino terminus of Type I receptors is located on the extracellular side of the membrane, whereas Type II receptors have this same protein tail in the intracellular milieu.

Still other embodiments of the invention utilize transferrin as a carrier or stimulant of RME of mucosally delivered biologically active agents. Transferrin, an 80 kDa iron-transporting glycoprotein, is efficiently taken up into cells by RME. Transferrin receptors are found on the surface of most proliferating cells, in elevated numbers on erythroblasts and on many kinds of tumors. The transcytosis of transferrin (Tf) and transferrin conjugates is reportedly enhanced in the presence of Brefeldin A (BFA), a fungal metabolite. In other studies, BFA treatment has been reported to rapidly increase apical endocytosis of both ricin and HRP in MDCK cells. Thus, BFA and other agents that stimulate receptor-mediated transport can be employed within the methods of the invention as combinatorially formulated (e.g., conjugated) and/or coordinately administered agents to enhance receptor-mediated transport of biologically active agents, including Y2 receptor-binding peptide proteins, analogs and mimetics.

Polymeric Delivery Vehicles and Methods

Within certain aspects of the invention, Y2 receptor-binding peptide proteins, analogs and mimetics, other biologically active agents disclosed herein, and delivery-enhancing agents as described above, are, individually or combinatorially, incorporated within a mucosally (e.g., nasally) administered formulation that includes a biocompatible polymer functioning as a carrier or base. Such polymer carriers include polymeric powders, matrices or microparticulate delivery vehicles, among other polymer forms. The polymer can be of plant, animal, or synthetic origin. Often the polymer is crosslinked. Additionally, in these delivery systems the Y2 receptor-binding peptide, analog or mimetic, can be functionalized in a manner where it can be covalently bound to the polymer and rendered inseparable from the polymer by simple washing. In other embodiments, the polymer is chemically modified with an inhibitor of enzymes or other agents which may degrade or inactivate the biologically active agent(s) and/or delivery enhancing agent(s). In certain formulations, the polymer is a partially or completely water insoluble but water swellable polymer, e.g., a hydrogel. Polymers useful in this aspect of the invention are desirably water interactive and/or hydrophilic in nature to absorb significant quantities of water, and they often form hydrogels when placed in contact with water or aqueous media for a period of time sufficient to reach equilibrium with water. In more detailed embodiments, the polymer is a hydrogel which, when placed in contact with excess water, absorbs at least two times its weight of water at equilibrium when exposed to water at room temperature, U.S. Pat. No. 6,004,583.

Drug delivery systems based on biodegradable polymers are preferred in many biomedical applications because such systems are broken down either by hydrolysis or by enzymatic reaction into non-toxic molecules. The rate of degradation is controlled by manipulating the composition of the biodegradable polymer matrix. These types of systems can therefore be employed in certain settings for long-term release of biologically active agents. Biodegradable polymers such as poly(glycolic acid) (PGA), poly-(lactic acid) (PLA), and poly(D,L-lactic-co-glycolic acid) (PLGA), have received considerable attention as possible drug delivery carriers, since the degradation products of these polymers have been found to have low toxicity. During the normal metabolic function of the body these polymers degrade into carbon dioxide and water. These polymers have also exhibited excellent biocompatibility.

For prolonging the biological activity of Y2 receptor-binding peptide, analogs and mimetics, and other biologically active agents disclosed herein, as well as optional delivery-enhancing agents, these agents may be incorporated into polymeric matrices, e.g., polyorthoesters, polyanhydrides, or polyesters. This yields sustained activity and release of the active agent(s), e.g., as determined by the degradation of the polymer matrix. Although the encapsulation of biotherapeutic molecules inside synthetic polymers may stabilize them during storage and delivery, the largest obstacle of polymer-based release technology is the activity loss of the therapeutic molecules during the formulation processes that often involve heat, sonication or organic solvents.

Absorption-promoting polymers contemplated for use within the invention may include derivatives and chemically or physically modified versions of the foregoing types of polymers, in addition to other naturally occurring or synthetic polymers, gums, resins, and other agents, as well as blends of these materials with each other or other polymers, so long as the alterations, modifications or blending do not adversely affect the desired properties, such as water absorption, hydrogel formation, and/or chemical stability for useful application. In more detailed aspects of the invention, polymers such as nylon, acrylan and other normally hydrophobic synthetic polymers may be sufficiently modified by reaction to become water swellable and/or form stable gels in aqueous media.

Absorption-promoting polymers of the invention may include polymers from the group of homo- and copolymers based on various combinations of the following vinyl monomers: acrylic and methacrylic acids, acrylamide, methacrylamide, hydroxyethylacrylate or methacrylate, vinylpyrrolidones, as well as polyvinylalcohol and its co- and terpolymers, polyvinylacetate, its co- and terpolymers with the above listed monomers and 2-acrylamido-2-methyl-propanesulfonic acid (AMPS®). Very useful are copolymers of the above listed monomers with copolymerizable functional monomers such as acryl or methacryl amide acrylate or methacrylate esters where the ester groups are derived from straight or branched chain alkyl, aryl having up to four aromatic rings which may contain alkyl substituents of 1 to 6 carbons; steroidal, sulfates, phosphates or cationic monomers such as N,N-dimethylaminoalkyl(meth)acrylamide, dimethylaminoalkyl(meth)acrylate, (meth)acryloxyalkyltrimethylammonium chloride, (meth)acryloxyalkyldimethylbenzyl ammonium chloride.

Additional absorption-promoting polymers for use within the invention are those classified as dextrans, dextrins, and from the class of materials classified as natural gums and resins, or from the class of natural polymers such as processed collagen, chitin, chitosan, pullalan, zooglan, alginates and modified alginates such as "Kelcoloid" (a polypropylene glycol modified alginate) gellan gums such as "Kelocogel", Xanathan gums such as "Keltrol", estastin, alpha hydroxy butyrate and its copolymers, hyaluronic acid and its derivatives, polylactic and glycolic acids.

A very useful class of polymers applicable within the instant invention are olefinically-unsaturated carboxylic acids containing at least one activated carbon-to-carbon olefinic double bond, and at least one carboxyl group; that is, an acid or functional group readily converted to an acid containing an olefinic double bond which readily functions in polymerization because of its presence in the monomer molecule, either in the alpha-beta position with respect to a carboxyl group, or as part of a terminal methylene grouping. Olefinically-unsaturated acids of this class include such materials as the acrylic acids typified by the acrylic acid itself, alpha-cyano acrylic acid, beta methylacrylic acid (crotonic acid), alpha-phenyl acrylic acid, beta-acryloxy propionic acid, cinnamic acid, p-chloro cinnamic acid, 1-carboxy-4-phenyl butadiene-1,3, itaconic acid, citraconic acid, mesaconic acid, glutaconic acid, aconitic acid, maleic acid, fumaric acid, and tricarboxy ethylene. As used herein, the term "carboxylic acid" includes the polycarboxylic acids and those acid anhydrides, such as maleic anhydride, wherein the anhydride group is formed by the elimination of one molecule of water from two carboxyl groups located on the same carboxylic acid molecule.

Representative acrylates useful as absorption-promoting agents within the invention include methyl acrylate, ethyl acrylate, propyl acrylate, isopropyl acrylate, butyl acrylate, isobutyl acrylate, methyl methacrylate, methyl ethacrylate, ethyl methacrylate, octyl acrylate, heptyl acrylate, octyl methacrylate, isopropyl methacrylate, 2-ethylhexyl methacrylate, nonyl acrylate, hexyl acrylate, n-hexyl methacrylate, and the like. Higher alkyl acrylic esters are decyl acrylate, isodecyl methacrylate, lauryl acrylate, stearyl acrylate, behenyl acrylate and melissyl acrylate and methacrylate versions thereof. Mixtures of two or three or more long chain acrylic esters may be successfully polymerized with one of the carboxylic monomers. Other comonomers include olefins, including alpha olefins, vinyl ethers, vinyl esters, and mixtures thereof.

Other vinylidene monomers, including the acrylic nitriles, may also be used as absorption-promoting agents within the methods and compositions of the invention to enhance delivery and absorption of one or more Y2 receptor-binding peptide proteins, analogs and mimetics, and other biologically active agent(s), including to enhance delivery of the active agent(s) to a target tissue or compartment in the subject (e.g., the liver, hepatic portal vein, CNS tissue or fluid, or blood plasma). Useful alpha, beta-olefinically unsaturated nitriles are preferably monoolefinically unsaturated nitriles having from 3 to 10 carbon atoms such as acrylonitrile, methacrylonitrile, and the like. Most preferred are acrylonitrile and methacrylonitrile. Acrylic amides containing from 3 to 35 carbon atoms including monoolefinically unsaturated amides also may be used. Representative amides include acrylamide, methacrylamide, N-t-butyl acrylamide, N-cyclohexyl acrylamide, higher alkyl amides, where the alkyl group on the nitrogen contains from 8 to 32 carbon atoms, acrylic amides including N-alkylol amides of alpha, beta-olefinically unsaturated carboxylic acids including those having from 4 to 10 carbon atoms such as N-methylol acrylamide, N-propanol acrylamide, N-methylol methacrylamide, N-methylol maleimide, N-methylol maleamic acid esters, N-methylol-p-vinyl benzamide, and the like.

Yet additional useful absorption promoting materials are alpha-olefins containing from 2 to 18 carbon atoms, more preferably from 2 to 8 carbon atoms; dienes containing from 4 to 10 carbon atoms; vinyl esters and allyl esters such as vinyl acetate; vinyl aromatics such as styrene, methyl styrene and chloro-styrene; vinyl and allyl ethers and ketones such as vinyl methyl ether and methyl vinyl ketone; chloroacrylates; cyanoalkyl acrylates such as alpha-cyanomethyl acrylate, and the alpha-, beta-, and gamma-cyanopropyl acrylates; alkoxyacrylates such as methoxy ethyl acrylate; haloacrylates as chloroethyl acrylate; vinyl halides and vinyl chloride, vinylidene chloride and the like; divinyls, diacrylates and other polyfunctional monomers such as divinyl ether, diethylene glycol diacrylate, ethylene glycol dimethacrylate, methylene-bis-acrylamide, allylpentaerythritol, and the like; and bis (beta-haloalkyl)alkenyl phosphonates such as bis(beta-chloroethyl)vinyl phosphonate and the like as are known to those skilled in the art. Copolymers wherein the carboxy containing monomer is a minor constituent, and the other vinylidene monomers present as major components are readily prepared in accordance with the methods disclosed herein.

When hydrogels are employed as absorption promoting agents within the invention, these may be composed of synthetic copolymers from the group of acrylic and methacrylic acids, acrylamide, methacrylamide, hydroxyethylacrylate (HEA) or methacrylate (HEMA), and vinylpyrrolidones which are water interactive and swellable. Specific illustrative examples of useful polymers, especially for the delivery of peptides or proteins, are the following types of polymers: (meth)acrylamide and 0.1 to 99 wt. % (meth)acrylic acid; (meth)acrylamides and 0.1–75 wt % (meth)acryloxyethyl trimethyammonium chloride; (meth)acrylamide and 0.1–75 wt % (meth)acrylamide; acrylic acid and 0.1–75 wt % alkyl(meth)acrylates; (meth)acrylamide and 0.1–75 wt % AMPS.RTM. (trademark of Lubrizol Corp.); (meth)acrylamide and 0 to 30 wt % alkyl(meth)acrylamides and 0.1–75 wt % AMPS.RTM.; (meth)acrylamide and 0.1–99 wt. % HEMA; (metb)acrylamide and 0.1 to 75 wt %

HEMA and 0.1 to 99%(meth)acrylic acid; (meth)acrylic acid and 0.1–99 wt % HEMA; 50 mole % vinyl ether and 50 mole % maleic anhydride; (meth)acrylamide and 0.1 to 75 wt % (meth)acryloxyalky dimethyl benzylammonium chloride; (meth)acrylamide and 0.1 to 99 wt % vinyl pyrrolidone; (meth)acrylamide and 50 wt % vinyl pyrrolidone and 0.1–99.9 wt % (meth)acrylic acid; (meth)acrylic acid and 0.1 to 75 wt % AMPS.RTM. and 0.1–75 wt % alkyl(meth)acrylamide. In the above examples, alkyl means $C_1$ to $C_{30}$, preferably $C_1$ to $C_{22}$, linear and branched and $C_4$ to $C_{16}$ cyclic; where (meth) is used, it means that the monomers with and without the methyl group are included. Other very useful hydrogel polymers are swellable, but insoluble versions of poly(vinyl pyrrolidone) starch, carboxymethyl cellulose and polyvinyl alcohol.

Additional polymeric hydrogel materials useful within the invention include (poly)hydroxyalkyl(meth)acrylate: anionic and cationic hydrogels: poly(electrolyte) complexes; poly(vinyl alcohols) having a low acetate residual: a swellable mixture of crosslinked agar and crosslinked carboxymethyl cellulose: a swellable composition comprising methyl cellulose mixed with a sparingly crosslinked agar; a water swellable copolymer produced by a dispersion of finely divided copolymer of maleic anhydride with styrene, ethylene, propylene, or isobutylene; a water swellable polymer of N-vinyl lactams; swellable sodium salts of carboxymethyl cellulose; and the like.

Other gelable, fluid imbibing and retaining polymers useful for forming the hydrophilic hydrogel for mucosal delivery of biologically active agents within the invention include pectin; polysaccharides such as agar, acacia, karaya, tragacenth, algins and guar and their crosslinked versions; acrylic acid polymers, copolymers and salt derivatives, polyacrylamides; water swellable indene maleic anhydride polymers; starch graft copolymers; acrylate type polymers and copolymers with water absorbability of about 2 to 400 times its original weight; diesters of polyglucan; a mixture of crosslinked poly(vinyl alcohol) and poly(N-vinyl-2-pyrrolidone); polyoxybutylene-polyethylene block copolymer gels; carob gum; polyester gels; poly urea gels; polyether gels; polyamide gels; polyimide gels; polypeptide gels; polyamino acid gels; poly cellulosic gels; crosslinked indene-maleic anhydride acrylate polymers; and polysaccharides.

Synthetic hydrogel polymers for use within the invention may be made by an infinite combination of several monomers in several ratios. The hydrogel can be crosslinked and generally possesses the ability to imbibe and absorb fluid and swell or expand to an enlarged equilibrium state. The hydrogel typically swells or expands upon delivery to the nasal mucosal surface, absorbing about 2–5, 5–10, 10–50, up to 50–100 or more times fold its weight of water. The optimum degree of swellability for a given hydrogel will be determined for different biologically active agents depending upon such factors as molecular weight, size, solubility and diffusion characteristics of the active agent carried by or entrapped or encapsulated within the polymer, and the specific spacing and cooperative chain motion associated with each individual polymer.

Hydrophilic polymers useful within the invention are water insoluble but water swellable. Such water-swollen polymers as typically referred to as hydrogels or gels. Such gels may be conveniently produced from water-soluble polymer by the process of crosslinking the polymers by a suitable crosslinking agent. However, stable hydrogels may also be formed from specific polymers under defined conditions of pH, temperature and/or ionic concentration, according to know methods in the art. Typically the polymers are cross-linked, that is, cross-linked to the extent that the polymers possess good hydrophilic properties, have improved physical integrity (as compared to non crosslinked polymers of the same or similar type) and exhibit improved ability to retain within the gel network both the biologically active agent of interest and additional compounds for coadministration therewith such as a cytokine or enzyme inhibitor, while retaining the ability to release the active agent(s) at the appropriate location and time.

Generally hydrogel polymers for use within the invention are crosslinked with a difunctional cross-linking in the amount of from 0.01 to 25 weight percent, based on the weight of the monomers forming the copolymer, and more preferably from 0.1 to 20 weight percent and more often from 0.1 to 15 weight percent of the crosslinking agent. Another useful amount of a crosslinking agent is 0.1 to 10 weight percent. Tri, tetra or higher multifunctional crosslinking agents may also be employed. When such reagents are utilized, lower amounts may be required to attain equivalent crosslinking density, i.e., the degree of crosslinking, or network properties that are sufficient to contain effectively the biologically active agent(s).

The crosslinks can be covalent, ionic or hydrogen bonds with the polymer possessing the ability to swell in the presence of water containing fluids. Such crosslinkers and crosslinking reactions are known to those skilled in the art and in many cases are dependent upon the polymer system. Thus a crosslinked network may be formed by free radical copolymerization of unsaturated monomers. Polymeric hydrogels may also be formed by crosslinking preformed polymers by reacting functional groups found on the polymers such as alcohols, acids, amines with such groups as glyoxal, formaldehyde or glutaraldehyde, bis anhydrides and the like.

The polymers also may be cross-linked with any polyene, e.g. decadiene or trivinyl cyclohexane; acrylamides, such as N,N-methylene-bis(acrylamide); polyfunctional acrylates, such as trimethylol propane triacrylate; or polyfunctional vinylidene monomer containing at least 2 terminal $CH_2$<groups, including, for example, divinyl benzene, divinyl naphthlene, allyl acrylates and the like. In certain embodiments, cross-linking monomers for use in preparing the copolymers are polyalkenyl polyethers having more than one alkenyl ether grouping per molecule, which may optionally possess alkenyl groups in which an olefinic double bond is present attached to a terminal methylene grouping (e.g., made by the etherification of a polyhydric alcohol containing at least 2 carbon atoms and at least 2 hydroxyl groups). Compounds of this class may be produced by reacting an alkenyl halide, such as allyl chloride or allyl bromide, with a strongly alkaline aqueous solution of one or more polyhydric alcohols. The product may be a complex mixture of polyethers with varying numbers of ether groups. Efficiency of the polyether cross-linking agent increases with the number of potentially polymerizable groups on the molecule. Typically, polyethers containing an average of two or more alkenyl ether groupings per molecule are used. Other cross-linking monomers include for example, diallyl esters, dimethallyl ethers, allyl or methallyl acrylates and acrylamides, tetravinyl silane, polyalkenyl methanes, diacrylates, and dimethacrylates, divinyl compounds such as divinyl benzene, polyallyl phosphate, diallyloxy compounds and phosphite esters and the like. Typical agents are allyl pentaerythritol, allyl sucrose, trimethylolpropane triacrylate, 1,6-hexanediol diacrylate, trimethylolpropane diallyl ether, pentaerythritol triacrylate, tetramethylene dimethacrylate, ethylene diacrylate, ethylene dimethacrylate, triethylene glycol dimethacrylate, and the like. Allyl pentaerythritol, trimethylolpropane diallylether and allyl sucrose provide suitable polymers. When the cross-linking agent is present, the polymeric mixtures usually contain between about 0.01 to 20 weight percent, e.g., 1%, 5%, or 10% or more by weight of cross-linking monomer based on the total of carboxylic acid monomer, plus other monomers.

In more detailed aspects of the invention, mucosal delivery of Y2 receptor-binding peptide, analogs and mimetics, and other biologically active agents disclosed herein, is enhanced by retaining the active agent(s) in a slow-release or enzymatically or physiologically protective carrier or vehicle, for example a hydrogel that shields the active agent from the action of the degradative enzymes. In certain embodiments, the active agent is bound by chemical means to the carrier or vehicle, to which may also be admixed or bound additional agents such as enzyme inhibitors, cytokines, etc. The active agent may alternately be immobilized through sufficient physical entrapment within the carrier or vehicle, e.g., a polymer matrix.

Polymers such as hydrogels useful within the invention may incorporate functional linked agents such as glycosides chemically incorporated into the polymer for enhancing intranasal bioavailability of active agents formulated therewith. Examples of such glycosides are glucosides, fructosides, galactosides, arabinosides, mannosides and their alkyl substituted derivatives and natural glycosides such as arbutin, phlorizin, amygdalin, digitonin, saponin, and indican. There are several ways in which a typical glycoside may be bound to a polymer. For example, the hydrogen of the hydroxyl groups of a glycoside or other similar carbohydrate may be replaced by the alkyl group from a hydrogel polymer to form an ether. Also, the hydroxyl groups of the glycosides may be reacted to esterify the carboxyl groups of a polymeric hydrogel to form polymeric esters in situ. Another approach is to employ condensation of acetobromoglucose with cholest-5-en-3beta-ol on a copolymer of maleic acid. N-substituted polyacrylamides can be synthesized by the reaction of activated polymers with omega-aminoalkylglycosides: (1) (carbohydrate-spacer)(n)-polyacrylamide, 'pseudopolysaccharides'; (2) (carbohydrate spacer)(n)-phosphatidylethanolamine(m)-polyacrylamide, neoglycolipids, derivatives of phosphatidylethanolamine; (3) (carbohydrate-spacer)(n)-biotin(m)-polyacrylamide. These biotinylated derivatives may attach to lectins on the mucosal surface to facilitate absorption of the biologically active agent(s), e.g., a polymer-encapsulated Y2 receptor-binding peptide.

Within more detailed aspects of the invention, one or more Y2 receptor-binding peptide, analogs and mimetics, and/or other biologically active agents, disclosed herein, optionally including secondary active agents such as protease inhibitor(s), cytokine(s), additional modulator(s) of intercellular junctional physiology, etc., are modified and bound to a polymeric carrier or matrix. For example, this may be accomplished by chemically binding a peptide or protein active agent and other optional agent(s) within a crosslinked polymer network. It is also possible to chemically modify the polymer separately with an interactive agent such as a glycosidal containing molecule. In certain aspects, the biologically active agent(s), and optional secondary active agent(s), may be functionalized, i.e., wherein an appropriate reactive group is identified or is chemically added to the active agent(s). Most often an ethylenic polymerizable group is added, and the functionalized active agent is then copolymerized with monomers and a crosslinking agent using a standard polymerization method such as solution polymerization (usually in water), emulsion, suspension or dispersion polymerization. Often, the functionalizing agent is provided with a high enough concentration of functional or polymerizable groups to insure that several sites on the active agent(s) are functionalized. For example, in a polypeptide comprising 16 amine sites, it is generally desired to functionalize at least 2, 4, 5, 7, and up to 8 or more of the sites.

After functionalization, the functionalized active agent(s) is/are mixed with monomers and a crosslinking agent that comprise the reagents from which the polymer of interest is formed. Polymerization is then induced in this medium to create a polymer containing the bound active agent(s). The polymer is then washed with water or other appropriate solvents and otherwise purified to remove trace unreacted impurities and, if necessary, ground or broken up by physical means such as by stirring, forcing it through a mesh, ultrasonication or other suitable means to a desired particle size. The solvent, usually water, is then removed in such a manner as to not denature or otherwise degrade the active agent(s). One desired method is lyophilization (freeze drying) but other methods are available and may be used (e.g., vacuum drying, air drying, spray drying, etc.).

To introduce polymerizable groups in peptides, proteins and other active agents within the invention, it is possible to react available amino, hydroxyl, thiol and other reactive groups with electrophiles containing unsaturated groups. For example, unsaturated monomers containing N-hydroxy succinimidyl groups, active carbonates such as p-nitrophenyl carbonate, trichlorophenyl carbonates, tresylate, oxycarbonylimidazoles, epoxide, isocyanates and aldehyde, and unsaturated carboxymethyl azides and unsaturated orthopyridyl-disulfide belong to this category of reagents. Illustrative examples of unsaturated reagents are allyl glycidyl ether, allyl chloride, allylbromide, allyl iodide, acryloyl chloride, allyl isocyanate, allylsulfonyl chloride, maleic anhydride, copolymers of maleic anhydride and allyl ether, and the like.

All of the lysine active derivatives, except aldehyde, can generally react with other amino acids such as imidazole groups of histidine and hydroxyl groups of tyrosine and the thiol groups of cystine if the local environment enhances nucleophilicity of these groups. Aldehyde containing functionalizing reagents are specific to lysine. These types of reactions with available groups from lysines, cysteines, tyrosine have been extensively documented in the literature and are known to those skilled in the art.

In the case of biologically active agents that contain amine groups, it is convenient to react such groups with an acyloyl chloride, such as acryloyl chloride, and introduce the polymerizable acrylic group onto the reacted agent. Then during preparation of the polymer, such as during the crosslinking of the copolymer of acrylamide and acrylic acid, the functionalized active agent, through the acrylic groups, is attached to the polymer and becomes bound thereto.

In additional aspects of the invention, biologically active agents, including peptides, proteins, nucleosides, and other molecules which are bioactive in vivo, are conjugation-stabilized by covalently bonding one or more active agent(s) to a polymer incorporating as an integral part thereof both a hydrophilic moiety, e.g., a linear polyalkylene glycol, a lipophilic moiety (see, e.g., U.S. Pat. No. 5,681,811). In one aspect, a biologically active agent is covalently coupled with a polymer comprising (i) a linear polyalkylene glycol moiety and (ii) a lipophilic moiety, wherein the active agent, linear polyalkylene glycol moiety, and the lipophilic moiety are conformationally arranged in relation to one another such that the active therapeutic agent has an enhanced in vivo resistance to enzymatic degradation (i.e., relative to its stability under similar conditions in an unconjugated form devoid of the polymer coupled thereto). In another aspect, the conjugation-stabilized formulation has a three-dimensional conformation comprising the biologically active agent covalently coupled with a polysorbate complex comprising (i) a linear polyalkylene glycol moiety and (ii) a lipophilic moiety, wherein the active agent, the linear polyalkylene glycol moiety and the lipophilic moiety are conformationally arranged in relation to one another such that (a) the lipophilic moiety is exteriorly available in the three-dimensional conformation, and (b) the active agent in the composition has an enhanced in vivo resistance to enzymatic degradation.

In a further related aspect, a multiligand conjugated complex is provided which comprises a biologically active agent covalently coupled with a triglyceride backbone moiety through a polyalkylene glycol spacer group bonded at a carbon atom of the triglyceride backbone moiety, and at least one fatty acid moiety covalently attached either directly to a carbon atom of the triglyceride backbone moiety or covalently joined through a polyalkylene glycol spacer moiety (see, e.g., U.S. Pat. No. 5,681,811). In such a multiligand conjugated therapeutic agent complex, the alpha' and beta carbon atoms of the triglyceride bioactive moiety may have fatty acid moieties attached by covalently bonding either directly thereto, or indirectly covalently bonded thereto through polyalkylene glycol spacer moieties. Alternatively, a fatty acid moiety may be covalently attached either directly or through a polyalkylene glycol spacer moiety to the alpha and alpha' carbons of the triglyceride backbone moiety, with the bioactive therapeutic agent being covalently coupled with the gamma-carbon of the triglyceride backbone moiety, either being directly covalently bonded thereto or indirectly bonded thereto through a polyalkylene spacer moiety. It will be recognized that a wide variety of structural, compositional, and conformational forms are possible for the multiligand conjugated therapeutic agent complex comprising the triglyceride backbone moiety, within the scope of the invention. It is further noted that in such a multiligand conjugated therapeutic agent complex, the biologically active agent(s) may advantageously be covalently coupled with the triglyceride modified backbone moiety through alkyl spacer groups, or alternatively other acceptable spacer groups, within the scope of the invention. As used in such context, acceptability of the spacer group refers to steric, compositional, and end use application specific acceptability characteristics.

In yet additional aspects of the invention, a conjugation-stabilized complex is provided which comprises a polysorbate complex comprising a polysorbate moiety including a triglyceride backbone having covalently coupled to alpha, alpha' and beta carbon atoms thereof functionalizing groups including (i) a fatty acid group; and (ii) a polyethylene glycol group having a biologically active agent or moiety covalently bonded thereto, e.g., bonded to an appropriate functionality of the polyethylene glycol group. Such covalent bonding may be either direct, e.g., to a hydroxy terminal functionality of the polyethylene glycol group, or alternatively, the covalent bonding may be indirect, e.g., by reactively capping the hydroxy terminus of the polyethylene glycol group with a terminal carboxy functionality spacer group, so that the resulting capped polyethylene glycol group has a terminal carboxy functionality to which the biologically active agent or moiety may be covalently bonded.

In yet additional aspects of the invention, a stable, aqueously soluble, conjugation-stabilized complex is provided which comprises one or more Y2 receptor-binding peptide proteins, analogs and mimetics, and/or other biologically active agent(s)+ disclosed herein covalently coupled to a physiologically compatible polyethylene glycol (PEG) modified glycolipid moiety. In such complex, the biologically active agent(s) may be covalently coupled to the physiologically compatible PEG modified glycolipid moiety by a labile covalent bond at a free amino acid group of the active agent, wherein the labile covalent bond is scissionable in vivo by biochemical hydrolysis and/or proteolysis. The physiologically compatible PEG modified glycolipid moiety may advantageously comprise a polysorbate polymer, e.g., a polysorbate polymer comprising fatty acid ester groups selected from the group consisting of monopalmitate, dipalmitate, monolaurate, dilaurate, trilaurate, monoleate, dioleate, trioleate, monostearate, distearate, and tristearate. In such complex, the physiologically compatible PEG modified glycolipid moiety may suitably comprise a polymer selected from the group consisting of polyethylene glycol ethers of fatty acids, and polyethylene glycol esters of fatty acids, wherein the fatty acids for example comprise a fatty acid selected from the group consisting of lauric, palmitic, oleic, and stearic acids.

Storage of Material

In certain aspects of the invention, the combinatorial formulations and/or coordinate administration methods herein incorporate an effective amount of peptides and proteins which may adhere to charged glass thereby reducing the effective concentration in the container. Silanized containers, for example, silanized glass containers, are used to store the finished product to reduce adsorption of the polypeptide or protein to a glass container.

In yet additional aspects of the invention, a kit for treatment of a mammalian subject comprises a stable pharmaceutical composition of one or more Y2 receptor-binding peptide compound(s) formulated for mucosal delivery to the mammalian subject wherein the composition is effective to alleviate one or more symptom(s) of obesity, cancer, or malnutrition or wasting related to cancer in said subject without unacceptable adverse side effects. The kit further comprises a pharmaceutical reagent vial to contain the one or more Y2 receptor-binding peptide compounds. The pharmaceutical reagent vial is composed of pharmaceutical grade polymer, glass or other suitable material. The pharmaceutical reagent vial is, for example, a silanized glass vial. The kit further comprises an aperture for delivery of the composition to a nasal mucosal surface of the subject. The delivery aperture is composed of a pharmaceutical grade polymer, glass or other suitable material. The delivery aperture is, for example, a silanized glass.

A silanization technique combines a special cleaning technique for the surfaces to be silanized with a silanization process at low pressure. The silane is in the gas phase and at an enhanced temperature of the surfaces to be silanized. The method provides reproducible surfaces with stable, homogeneous and functional silane layers having characteristics of a monolayer. The silanized surfaces prevent binding to the glass of polypeptides or mucosal delivery enhancing agents of the present invention.

The procedure is useful to prepare silanized pharmaceutical reagent vials to hold Y2 receptor-binding peptide compositions of the present invention. Glass trays are cleaned by rinsing with double distilled water (ddH$_2$O) before using. The silane tray is then be rinsed with 95% EtOH, and the acetone tray is rinsed with acetone. Pharmaceutical reagent vials are sonicated in acetone for 10 minutes. After the acetone sonication, reagent vials are washed in ddH$_2$O tray at least twice. Reagent vials are sonicated in 0.1M NaOH for 10 minutes. While the reagent vials are sonicating in NaOH, the silane solution is made under a hood. (Silane solution: 800 mL of 95% ethanol; 96 L of glacial acetic acid; 25 mL of glycidoxypropyltrimethoxy silane). After the NaOH sonication, reagent vials are washed in ddH$_2$O tray at least twice. The reagent vials are sonicated in silane solution for 3 to 5 minutes. The reagent vials are washed in 100% EtOH tray. The reagent vials are dried with prepurified N$_2$ gas and stored in a 100° C. oven for at least 2 hours before using.

Bioadhesive Delivery Vehicles and Methods

In certain aspects of the invention, the combinatorial formulations and/or coordinate administration methods herein incorporate an effective amount of a nontoxic bioadhesive as an adjunct compound or carrier to enhance mucosal delivery of one or more biologically active agent(s). Bioadhesive agents in this context exhibit general or specific adhesion to one or more components or surfaces of the targeted mucosa. The bioadhesive maintains a desired concentration gradient of the biologically active agent into or across the mucosa to ensure penetration of even large molecules (e.g., peptides and proteins) into or through the mucosal epithelium. Typically, employment of a bioadhesive within the methods and compositions of the invention yields a two- to five-fold, often a five- to ten-fold increase in permeability for peptides and proteins into or through the mucosal epithelium. This enhancement of epithelial permeation often permits effective transmucosal delivery of large macromolecules, for example to the basal portion of the nasal epithelium or into the adjacent extracellular compartments or into a blood plasma or CNS tissue or fluid.

This enhanced delivery provides for greatly improved effectiveness of delivery of bioactive peptides, proteins and other macromolecular therapeutic species. These results will depend in part on the hydrophilicity of the compound, whereby greater penetration will be achieved with hydrophilic species compared to water insoluble compounds. In addition to these effects, employment of bioadhesives to enhance drug persistence at the mucosal surface can elicit a reservoir mechanism for protracted drug delivery, whereby compounds not only penetrate across the mucosal tissue but also back-diffuse toward the mucosal surface once the material at the surface is depleted.

A variety of suitable bioadhesives are disclosed in the art for oral administration, U.S. Pat. Nos. 3,972,995; 4,259,314; 4,680,323; 4,740,365; 4,573,996; 4,292,299; 4,715,369; 4,876,092; 4,855,142; 4,250,163; 4,226,848; 4,948,580; U.S. Pat. No. Reissue 33,093, which find use within the novel methods and compositions of the invention. The potential of various bioadhesive polymers as a mucosal, e.g., nasal, delivery platform within the methods and compositions of the invention can be readily assessed by determining their ability to retain and release Y2 receptor-binding peptide, as well as by their capacity to interact with the mucosal surfaces following incorporation of the active agent therein. In addition, well known methods will be applied to determine the biocompatibility of selected polymers with the tissue at the site of mucosal administration. When the target mucosa is covered by mucus (i.e., in the absence of mucolytic or mucus-clearing treatment), it can serve as a connecting link to the underlying mucosal epithelium. Therefore, the term "bioadhesive" as used herein also covers mucoadhesive compounds useful for enhancing mucosal delivery of biologically active agents within the invention. However, adhesive contact to mucosal tissue mediated through adhesion to a mucus gel layer may be limited by incomplete or transient attachment between the mucus layer and the underlying tissue, particularly at nasal surfaces where rapid mucus clearance occurs. In this regard, mucin glycoproteins are continuously secreted and, immediately after their release from cells or glands, form a viscoelastic gel. The luminal surface of the adherent gel layer, however, is continuously eroded by mechanical, enzymatic and/or ciliary action. Where such activities are more prominent or where longer adhesion times are desired, the coordinate administration methods and combinatorial formulation methods of the invention may further incorporate mucolytic and/or ciliostatic methods or agents as disclosed herein above.

Typically, mucoadhesive polymers for use within the invention are natural or synthetic macromolecules which adhere to wet mucosal tissue surfaces by complex, but non-specific, mechanisms. In addition to these mucoadhesive polymers, the invention also provides methods and compositions incorporating bioadhesives that adhere directly to a cell surface, rather than to mucus, by means of specific, including receptor-mediated, interactions. One example of bioadhesives that function in this specific manner is the group of compounds known as lectins. These are glycoproteins with an ability to specifically recognize and bind to sugar molecules, e.g. glycoproteins or glycolipids, which form part of intranasal epithelial cell membranes and can be considered as "lectin receptors".

In certain aspects of the invention, bioadhesive materials for enhancing intranasal delivery of biologically active agents comprise a matrix of a hydrophilic, e.g., water soluble or swellable, polymer or a mixture of polymers that can adhere to a wet mucous surface. These adhesives may be formulated as ointments, hydrogels (see above) thin films, and other application forms. Often, these adhesives have the biologically active agent mixed therewith to effectuate slow release or local delivery of the active agent. Some are formulated with additional ingredients to facilitate penetration of the active agent through the nasal mucosa, e.g., into the circulatory system of the individual.

Various polymers, both natural and synthetic ones, show significant binding to mucus and/or mucosal epithelial surfaces under physiological conditions. The strength of this interaction can readily be measured by mechanical peel or shear tests. When applied to a humid mucosal surface, many dry materials will spontaneously adhere, at least slightly. After such an initial contact, some hydrophilic materials start to attract water by adsorption, swelling or capillary forces, and if this water is absorbed from the underlying substrate or from the polymer-tissue interface, the adhesion may be sufficient to achieve the goal of enhancing mucosal absorption of biologically active agents. Such 'adhesion by hydration' can be quite strong, but formulations adapted to employ this mechanism must account for swelling which continues as the dosage transforms into a hydrated mucilage. This is projected for many hydrocolloids useful within the invention, especially some cellulose-derivatives, which are generally non-adhesive when applied in pre-hydrated state. Nevertheless, bioadhesive drug delivery systems for mucosal administration are effective within the invention when such materials are applied in the form of a dry polymeric powder, microsphere, or film-type delivery form.

Other polymers adhere to mucosal surfaces not only when applied in dry, but also in fully hydrated state, and in the presence of excess amounts of water. The selection of a mucoadhesive thus requires due consideration of the conditions, physiological as well as physico-chemical, under which the contact to the tissue will be formed and maintained. In particular, the amount of water or humidity usually present at the intended site of adhesion, and the prevailing pH, are known to largely affect the mucoadhesive binding strength of different polymers.

Several polymeric bioadhesive drug delivery systems have been fabricated and studied in the past 20 years, not always with success. A variety of such carriers are, however, currently used in clinical applications involving dental, orthopedic, ophthalmologic, and surgical uses. For example, acrylic-based hydrogels have been used extensively for bioadhesive devices. Acrylic-based hydrogels are well suited for bioadhesion due to their flexibility and nonabrasive characteristics in the partially swollen state, which reduce damage-causing attrition to the tissues in contact. Furthermore, their high permeability in the swollen state allows unreacted monomer, un-crosslinked polymer chains, and the initiator to be washed out of the matrix after polymerization, which is an important feature for selection of bioadhesive materials for use within the invention. Acrylic-based polymer devices exhibit very high adhesive bond strength. For controlled mucosal delivery of peptide and protein drugs, the methods and compositions of the invention optionally include the use of carriers, e.g., polymeric delivery vehicles, that function in part to shield the biologically active agent from proteolytic breakdown, while at the same time providing for enhanced penetration of the peptide or protein into or through the nasal mucosa. In this context, bioadhesive polymers have demonstrated considerable potential for enhancing oral drug delivery. As an example, the bioavailability of 9-desglycinamide, 8-arginine vasopressin (DGAVP) intraduodenally administered to rats together with a 1% (w/v) saline dispersion of the mucoadhesive poly(acrylic acid) derivative polycarbophil, was 3–5-fold increased compared to an aqueous solution of the peptide drug without this polymer.

Mucoadhesive polymers of the poly(acrylic acid)-type are potent inhibitors of some intestinal proteases. The mechanism of enzyme inhibition is explained by the strong affinity of this class of polymers for divalent cations, such as calcium or zinc, which are essential cofactors of metalloproteinases, such as trypsin and chymotrypsin. Depriving the proteases of their cofactors by poly(acrylic acid) was reported to induce irreversible structural changes of the enzyme proteins which were accompanied by a loss of enzyme activity. At the same time, other mucoadhesive polymers (e.g., some cellulose derivatives and chitosan) may not inhibit proteolytic enzymes under certain conditions. In contrast to other enzyme inhibitors contemplated for use within the invention (e.g. aprotinin, bestatin), which are relatively small molecules, the trans-nasal absorption of inhibitory polymers is likely to be minimal in light of the size of these molecules, and thereby eliminate possible adverse side effects. Thus, mucoadhesive polymers, particularly of the poly(acrylic acid)-type, may serve both as an absorption-promoting adhesive and enzyme-protective agent to enhance controlled delivery of peptide and protein drugs, especially when safety concerns are considered.

In addition to protecting against enzymatic degradation, bioadhesives and other polymeric or non-polymeric absorption-promoting agents for use within the invention may directly increase mucosal permeability to biologically active agents. To facilitate the transport of large and hydrophilic molecules, such as peptides and proteins, across the nasal epithelial barrier, mucoadhesive polymers and other agents have been postulated to yield enhanced permeation effects beyond what is accounted for by prolonged premucosal residence time of the delivery system. The time course of drug plasma concentrations reportedly suggested that the bioadhesive microspheres caused an acute, but transient increase of insulin permeability across the nasal mucosa. Other mucoadhesive polymers for use within the invention, for example chitosan, reportedly enhance the permeability of certain mucosal epithelia even when they are applied as an aqueous solution or gel. Another mucoadhesive polymer reported to directly affect epithelial permeability is hyaluronic acid and ester derivatives thereof. A particularly useful bioadhesive agent within the coordinate administration, and/or combinatorial formulation methods and compositions of the invention is chitosan, as well as its analogs and derivatives. Chitosan is a non-toxic, biocompatible and biodegradable polymer that is widely used for pharmaceutical and medical applications because of its favorable properties of low toxicity and good biocompatibility. It is a natural polyaminosaccharide prepared from chitin by N-deacetylation with alkali. As used within the methods and compositions of the invention, chitosan increases the retention of Y2 receptor-binding peptide proteins, analogs and mimetics, and other biologically active agents disclosed herein at a mucosal site of application. This mode of administration can also improve patient compliance and acceptance. As further provided herein, the methods and compositions of the invention will optionally include a novel chitosan derivative or chemically modified form of chitosan. One such novel derivative for use within the invention is denoted as a β-[1→4]-2-guanidino-2-deoxy-D-glucose polymer (poly-GuD). Chitosan is the N-deacetylated product of chitin, a naturally occurring polymer that has been used extensively to prepare microspheres for oral and intra-nasal formulations. The chitosan polymer has also been proposed as a soluble carrier for parenteral drug delivery. Within one aspect of the invention, o-methylisourea is used to convert a chitosan amine to its guanidinium moiety. The guanidinium compound is prepared, for example, by the reaction between equi-normal solutions of chitosan and o-methylisourea at pH above 8.0.

The guanidinium product is -[14]-guanidino-2-deoxy-D-glucose polymer. It is abbreviated as Poly-GuD in this context (Monomer F. W. of Amine in Chitosan=161; Monomer F. W. of Guanidinium in Poly-GuD=203).

One exemplary Poly-GuD preparation method for use within the invention involves the following protocol.

Solutions:

Preparation of 0.5% Acetic Acid Solution (0.088N):

Pipette 2.5 mL glacial acetic acid into a 500 mL volumetric flask, dilute to volume with purified water.

Preparation of 2N NaOH Solution:

Transfer about 20 g NaOH pellets into a beaker with about 150 mL of purified water. Dissolve and cool to room temperature. Transfer the solution into a 250-mL volumetric flask, dilute to volume with purified water.

Preparation of O-methylisourea Sulfate (0.4N urea group equivalent):

Transfer about 493 mg of O-methylisourea sulfate into a 10-mL volumetric flask, dissolve and dilute to volume with purified water.

The pH of the solution is 4.2

Preparation of Barium Chloride Solution (0.2M):

Transfer about 2.086 g of Barium chloride into a 50-mL volumetric flask, dissolve and dilute to volume with purified water.

Preparation of Chitosan Solution (0.06N amine equivalent):

Transfer about 100 mg Chitosan into a 50 mL beaker, add 10 mL 0.5% Acetic Acid (0.088 N). Stir to dissolve completely.

The pH of the solution is about 4.5

Preparation of O-methylisourea Chloride Solution (0.2N urea group equivalent):

Pipette 5.0 mL of O-methylisourea sulfate solution (0.4 N urea group equivalent) and 5 mL of 0.2M Barium chloride solution into a beaker. A precipitate is formed. Continue to mix the solution for additional 5 minutes. Filter the solution through 0.45 m filter and discard the precipitate. The concentration of O-methylisourea chloride in the supernatant solution is 0.2 N urea group equivalents.

The pH of the solution is 4.2.

Procedure:

Add 1.5 mL of 2 N NaOH to 10 mL of the chitosan solution (0.06N amine equivalent) prepared as described in Section 2.5. Adjust the pH of the solution with 2N NaOH to about 8.2 to 8.4. Stir the solution for additional 10 minutes. Add 3.0 mL O-methylisourea chloride solution (0.2N urea group equivalent) prepared as described above. Stir the solution overnight.

Adjust the pH of solution to 5.5 with 0.5% Acetic Acid (0.088N).

Dilute the solution to a final volume of 25 mL using purified water.

The Poly-GuD concentration in the solution is 5 mg/mL, equivalent to 0.025 N (guanidium group).

Additional compounds classified as bioadhesive agents for use within the present invention act by mediating specific interactions, typically classified as "receptor-ligand interactions" between complementary structures of the bioadhesive compound and a component of the mucosal epithelial surface. Many natural examples illustrate this form of specific binding bioadhesion, as exemplified by lectin-sugar interactions. Lectins are (glyco) proteins of non-immune origin which bind to polysaccharides or glycoconjugates.

Several plant lectins have been investigated as possible pharmaceutical absorption-promoting agents. One plant lectin, Phaseolus vulgaris hemagglutinin (PHA), exhibits high oral bioavailability of more than 10% after feeding to rats. Tomato (Lycopersicon esculeutum) lectin (TL) appears safe for various modes of administration.

In summary, the foregoing bioadhesive agents are useful in the combinatorial formulations and coordinate administration methods of the instant invention, which optionally incorporate an effective amount and form of a bioadhesive agent to prolong persistence or otherwise increase mucosal absorption of one or more Y2 receptor-binding peptide proteins, analogs and mimetics, and other biologically active agents. The bioadhesive agents may be coordinately administered as adjunct compounds or as additives within the combinatorial formulations of the invention. In certain embodiments, the bioadhesive agent acts as a 'pharmaceutical glue', whereas in other embodiments adjunct delivery or combinatorial formulation of the bioadhesive agent serves to intensify contact of the biologically active agent with the nasal mucosa, in some cases by promoting specific receptor-ligand interactions with epithelial cell "receptors", and in others by increasing epithelial permeability to significantly increase the drug concentration gradient measured at a target site of delivery (e.g., liver, blood plasma, or CNS tissue or fluid). Yet additional bioadhesive agents for use within the invention act as enzyme (e.g., protease) inhibitors to enhance the stability of mucosally administered biotherapeutic agents delivered coordinately or in a combinatorial formulation with the bioadhesive agent.

Liposomes and Micellar Delivery Vehicles

The coordinate administration methods and combinatorial formulations of the instant invention optionally incorporate effective lipid or fatty acid based carriers, processing agents, or delivery vehicles, to provide improved formulations for mucosal delivery of Y2 receptor-binding peptide proteins, analogs and mimetics, and other biologically active agents. For example, a variety of formulations and methods are provided for mucosal delivery which comprise one or more of these active agents, such as a peptide or protein, admixed or encapsulated by, or coordinately administered with, a liposome, mixed micellar carrier, or emulsion, to enhance chemical and physical stability and increase the half life of the biologically active agents (e.g., by reducing susceptibility to proteolysis, chemical modification and/or denaturation) upon mucosal delivery.

Within certain aspects of the invention, specialized delivery systems for biologically active agents comprise small lipid vesicles known as liposomes. These are typically made from natural, biodegradable, non-toxic, and non-immunogenic lipid molecules, and can efficiently entrap or bind drug molecules, including peptides and proteins, into, or onto, their membranes. The attractiveness of liposomes as a peptide and protein delivery system within the invention is increased by the fact that the encapsulated proteins can remain in their preferred aqueous environment within the vesicles, while the liposomal membrane protects them against proteolysis and other destabilizing factors. Even though not all liposome preparation methods known are feasible in the encapsulation of peptides and proteins due to their unique physical and chemical properties, several methods allow the encapsulation of these macromolecules without substantial deactivation.

A variety of methods are available for preparing liposomes for use within the invention, U.S. Pat. Nos. 4,235,871, 4,501,728, and 4,837,028. For use with liposome delivery, the biologically active agent is typically entrapped within the liposome, or lipid vesicle, or is bound to the outside of the vesicle.

Like liposomes, unsaturated long chain fatty acids, which also have enhancing activity for mucosal absorption, can form closed vesicles with bilayer-like structures (so called "ufasomes"). These can be formed, for example, using oleic acid to entrap biologically active peptides and proteins for mucosal, e.g., intranasal, delivery within the invention.

Other delivery systems for use within the invention combine the use of polymers and liposomes to ally the advantageous properties of both vehicles such as encapsulation inside the natural polymer fibrin. In addition, release of biotherapeutic compounds from this delivery system is controllable through the use of covalent crosslinking and the addition of antifibrinolytic agents to the fibrin polymer.

More simplified delivery systems for use within the invention include the use of cationic lipids as delivery vehicles or carriers, which can be effectively employed to provide an electrostatic interaction between the lipid carrier and such charged biologically active agents as proteins and polyanionic nucleic acids. This allows efficient packaging of the drugs into a form suitable for mucosal administration and/or subsequent delivery to systemic compartments.

Additional delivery vehicles for use within the invention include long and medium chain fatty acids, as well as surfactant mixed micelles with fatty acids. Most naturally occurring lipids in the form of esters have important implications with regard to their own transport across mucosal surfaces. Free fatty acids and their monoglycerides which have polar groups attached have been demonstrated in the form of mixed micelles to act on the intestinal barrier as penetration enhancers. This discovery of barrier modifying function of free fatty acids (carboxylic acids with a chain length varying from 12 to 20 carbon atoms) and their polar derivatives has stimulated extensive research on the application of these agents as mucosal absorption enhancers.

For use within the methods of the invention, long chain fatty acids, especially fusogenic lipids (unsaturated fatty acids and monoglycerides such as oleic acid, linoleic acid, linoleic acid, monoolein, etc.) provide useful carriers to enhance mucosal delivery of Y2 receptor-binding peptide, analogs and mimetics, and other biologically active agents disclosed herein. Medium chain fatty acids (C6 to C12) and monoglycerides have also been shown to have enhancing activity in intestinal drug absorption and can be adapted for use within the mucosal delivery formulations and methods of the invention. In addition, sodium salts of medium and long chain fatty acids are effective delivery vehicles and absorption-enhancing agents for mucosal delivery of biologically active agents within the invention. Thus, fatty acids can be employed in soluble forms of sodium salts or by the addition of non-toxic surfactants, e.g., polyoxyethylated hydrogenated castor oil, sodium taurocholate, etc. Other fatty acid and mixed micellar preparations that are useful within the invention include, but are not limited to, Na caprylate (C8), Na caprate (C10), Na laurate (C12) or Na oleate (C18), optionally combined with bile salts, such as glycocholate and taurocholate.

Pegylation

Additional methods and compositions provided within the invention involve chemical modification of biologically active peptides and proteins by covalent attachment of polymeric materials, for example dextrans, polyvinyl pyrrolidones, glycopeptides, polyethylene glycol and polyamino acids. The resulting conjugated peptides and proteins retain their biological activities and solubility for mucosal administration. In alternate embodiments, Y2 receptor-binding peptide proteins, analogs and mimetics, and other biologically active peptides and proteins, are conjugated to polyalkylene oxide polymers, particularly polyethylene glycols (PEG). U.S. Pat. No. 4,179,337.

Amine-reactive PEG polymers for use within the invention include SC-PEG with molecular masses of 2000, 5000, 10000, 12000, and 20 000; U-PEG-10000; NHS-PEG-3400-biotin; T-PEG-5000; T-PEG-12000; and TPC-PEG-5000. PEGylation of biologically active peptides and proteins may be achieved by modification of carboxyl sites (e.g., aspartic acid or glutamic acid groups in addition to the carboxyl terminus). The utility of PEG-hydrazide in selective modification of carbodiimide-activated protein carboxyl groups under acidic conditions has been described. Alternatively, bifunctional PEG modification of biologically active peptides and proteins can be employed. In some procedures, charged amino acid residues, including lysine, aspartic acid, and glutamic acid, have a marked tendency to be solvent accessible on protein surfaces.

Other Stabilizing Modifications of Active Agents

In addition to PEGylation, biologically active agents such as peptides and proteins for use within the invention can be modified to enhance circulating half-life by shielding the active agent via conjugation to other known protecting or stabilizing compounds, for example by the creation of fusion proteins with an active peptide, protein, analog or mimetic linked to one or more carrier proteins, such as one or more immunoglobulin chains.

Formulation and Administration

Mucosal delivery formulations of the present invention comprise Y2 receptor-binding peptide, analogs and mimetics, typically combined together with one or more pharmaceutically acceptable carriers and, optionally, other therapeutic ingredients. The carrier(s) must be "pharmaceutically acceptable" in the sense of being compatible with the other ingredients of the formulation and not eliciting an unacceptable deleterious effect in the subject. Such carriers are described herein above or are otherwise well known to those skilled in the art of pharmacology. Desirably, the formulation should not include substances such as enzymes or oxidizing agents with which the biologically active agent to be administered is known to be incompatible. The formulations may be prepared by any of the methods well known in the art of pharmacy.

Within the compositions and methods of the invention, the Y2 receptor-binding peptide proteins, analogs and mimetics, and other biologically active agents disclosed herein may be administered to subjects by a variety of mucosal administration modes, including by oral, rectal, vaginal, intranasal, intrapulmonary, or transdermal delivery, or by topical delivery to the eyes, ears, skin or other mucosal surfaces. Optionally, Y2 receptor-binding peptide proteins, analogs and mimetics, and other biologically active agents disclosed herein can be coordinately or adjunctively administered by non-mucosal routes, including by intramuscular, subcutaneous, intravenous, intra-atrial, intra-articular, intraperitoneal, or parenteral routes. In other alternative embodiments, the biologically active agent(s) can be administered ex vivo by direct exposure to cells, tissues or organs originating from a mammalian subject, for example as a component of an ex vivo tissue or organ treatment formulation that contains the biologically active agent in a suitable, liquid or solid carrier.

Compositions according to the present invention are often administered in an aqueous solution as a nasal or pulmonary spray and may be dispensed in spray form by a variety of methods known to those skilled in the art. Preferred systems for dispensing liquids as a nasal spray are disclosed in U.S. Pat. No. 4,511,069. The formulations may be presented in multi-dose containers, for example in the sealed dispensing system disclosed in U.S. Pat. No. 4,511,069. Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or a mixture thereof.

Nasal and pulmonary spray solutions of the present invention typically comprise the drug or drug to be delivered, optionally formulated with a surface-active agent, such as a nonionic surfactant (e.g., polysorbate-80), and one or more buffers. In some embodiments of the present invention, the nasal spray solution further comprises a propellant. The pH of the nasal spray solution is optionally between about pH 3.0 and 6.0, preferably 4.5±0.5. Suitable buffers for use within these compositions are as described above or as otherwise known in the art. Other components may be added to enhance or maintain chemical stability, including preservatives, surfactants, dispersants, or gases. Suitable preservatives include, but are not limited to, phenol, methyl paraben, paraben, m-cresol, thiomersal, chlorobutanol, benzylalkonimum chloride, and the like. Suitable surfactants include, but are not limited to, oleic acid, sorbitan trioleate, polysorbates, lecithin, phosphatidyl cholines, and various long chain diglycerides and phospholipids. Suitable dispersants include, but are not limited to, ethylenediaminetetraacetic acid, and the like. Suitable gases include, but are not limited to, nitrogen, helium, chlorofluorocarbons (CFCs), hydrofluorocarbons (HFCs), carbon dioxide, air, and the like.

Within alternate embodiments, mucosal formulations are administered as dry powder formulations comprising the biologically active agent in a dry, usually lyophilized, form of an appropriate particle size, or within an appropriate particle size range, for intranasal delivery. Minimum particle size appropriate for deposition within the nasal or pulmonary passages is often about 0.5μ mass median equivalent aerodynamic diameter (MMEAD), commonly about 1μ MMEAD, and more typically about 2μ MMEAD. Maximum particle size appropriate for deposition within the nasal passages is often about 10μ MMEAD, commonly about 8μ MMEAD, and more typically about 4μ MMEAD. Intranasally respirable powders within these size ranges can be produced by a variety of conventional techniques, such as jet milling, spray drying, solvent precipitation, supercritical fluid condensation, and the like. These dry powders of appropriate MMEAD can be administered to a patient via a conventional dry powder inhaler (DPI), which rely on the patient's breath, upon pulmonary or nasal inhalation, to disperse the power into an aerosolized amount. Alternatively, the dry powder may be administered via air-assisted devices that use an external power source to disperse the powder into an aerosolized amount, e.g., a piston pump.

Dry powder devices typically require a powder mass in the range from about 1 mg to 20 mg to produce a single aerosolized dose ("puff"). If the required or desired dose of the biologically active agent is lower than this amount, the powdered active agent will typically be combined with a pharmaceutical dry bulking powder to provide the required total powder mass. Preferred dry bulking powders include sucrose, lactose, dextrose, mannitol, glycine, trehalose, human serum albumin (HSA), and starch. Other suitable dry bulking powders include cellobiose, dextrans, maltotriose, pectin, sodium citrate, sodium ascorbate, and the like.

To formulate compositions for mucosal delivery within the present invention, the biologically active agent can be combined with various pharmaceutically acceptable additives, as well as a base or carrier for dispersion of the active agent(s). Desired additives include, but are not limited to, pH control agents, such as arginine, sodium hydroxide, glycine, hydrochloric acid, citric acid, etc. In addition, local anesthetics (e.g., benzyl alcohol), isotonizing agents (e.g., sodium chloride, mannitol, sorbitol), adsorption inhibitors (e.g., Tween 80), solubility enhancing agents (e.g., cyclodextrins and derivatives thereof), stabilizers (e.g., serum albumin), and reducing agents (e.g., glutathione) can be included. When the composition for mucosal delivery is a liquid, the tonicity of the formulation, as measured with reference to the tonicity of 0.9% (w/v) physiological saline solution taken as unity, is typically adjusted to a value at which no substantial, irreversible tissue damage will be induced in the nasal mucosa at the site of administration. Generally, the tonicity of the solution is adjusted to a value of about ⅓ to 3, more typically ½ to 2, and most often ¾ to 1.7.

The biologically active agent may be dispersed in a base or vehicle, which may comprise a hydrophilic compound having a capacity to disperse the active agent and any desired additives. The base may be selected from a wide range of suitable carriers, including but not limited to, copolymers of polycarboxylic acids or salts thereof, carboxylic anhydrides (e.g. maleic anhydride) with other monomers (e.g. methyl(meth)acrylate, acrylic acid, etc.), hydrophilic vinyl polymers such as polyvinyl acetate, polyvinyl alcohol, polyvinylpyrrolidone, cellulose derivatives such as hydroxymethylcellulose, hydroxypropylcellulose, etc., and natural polymers such as chitosan, collagen, sodium alginate, gelatin, hyaluronic acid, and nontoxic metal salts thereof. Often, a biodegradable polymer is selected as a base or carrier, for example, polylactic acid, poly(lactic acid-glycolic acid) copolymer, polyhydroxybutyric acid, poly (hydroxybutyric acid-glycolic acid) copolymer and mixtures thereof. Alternatively or additionally, synthetic fatty acid esters such as polyglycerin fatty acid esters, sucrose fatty acid esters, etc. can be employed as carriers. Hydrophilic polymers and other carriers can be used alone or in combination, and enhanced structural integrity can be imparted to the carrier by partial crystallization, ionic bonding, crosslinking and the like. The carrier can be provided in a variety of forms, including fluid or viscous solutions, gels, pastes, powders, microspheres and films for direct application to the nasal mucosa. The use of a selected carrier in this context may result in promotion of absorption of the biologically active agent.

The biologically active agent can be combined with the base or carrier according to a variety of methods, and release of the active agent may be by diffusion, disintegration of the carrier, or associated formulation of water channels. In some circumstances, the active agent is dispersed in microcapsules (microspheres) or nanocapsules (nanospheres) prepared from a suitable polymer, e.g., isobutyl 2-cyanoacrylate and dispersed in a biocompatible dispersing medium applied to the nasal mucosa, which yields sustained delivery and biological activity over a protracted time.

To further enhance mucosal delivery of pharmaceutical agents within the invention, formulations comprising the active agent may also contain a hydrophilic low molecular weight compound as a base or excipient. Such hydrophilic low molecular weight compounds provide a passage medium through which a water-soluble active agent, such as a physiologically active peptide or protein, may diffuse through the base to the body surface where the active agent is absorbed. The hydrophilic low molecular weight compound optionally absorbs moisture from the mucosa or the administration atmosphere and dissolves the water-soluble active peptide. The molecular weight of the hydrophilic low molecular weight compound is generally not more than 10000 and preferably not more than 3000. Exemplary hydrophilic low molecular weight compound include polyol compounds, such as oligo-, di- and monosaccharides such as sucrose, mannitol, sorbitol, lactose, L-arabinose, D-erythrose, D-ribose, D-xylose, D-mannose, trehalose, D-galactose, lactulose, cellobiose, gentibiose, glycerin and polyethylene glycol. Other examples of hydrophilic low molecular weight compounds useful as carriers within the invention include N-methylpyrrolidone, and alcohols (e.g. oligovinyl alcohol, ethanol, ethylene glycol, propylene glycol, etc.) These hydrophilic low molecular weight compounds can be used alone or in combination with one another or with other active or inactive components of the intranasal formulation.

The compositions of the invention may alternatively contain as pharmaceutically acceptable carriers substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

Therapeutic compositions for administering the biologically active agent can also be formulated as a solution, microemulsion, or other ordered structure suitable for high concentration of active ingredients. The carrier can be a solvent or dispersion medium containing, for example, water, ethanol, polyol (for example, glycerol, propylene glycol, and liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols such as mannitol, sorbitol, or sodium chloride in the composition. Prolonged absorption of the biologically active agent can be brought about by including in the composition an agent which delays absorption, for example, monostearate salts and gelatin.

In certain embodiments of the invention, the biologically active agent is administered in a time-release formulation, for example in a composition which includes a slow release polymer. The active agent can be prepared with carriers that will protect against rapid release, for example a controlled release vehicle such as a polymer, microencapsulated delivery system or bioadhesive gel. Prolonged delivery of the active agent, in various compositions of the invention can be brought about by including in the composition agents that delay absorption, for example, aluminum monosterate hydrogels and gelatin. When controlled release formulations of the biologically active agent is desired, controlled release binders suitable for use in accordance with the invention include any biocompatible controlled-release material which is inert to the active agent and which is capable of incorporating the biologically active agent. Numerous such materials are known in the art. Useful controlled-release binders are materials that are metabolized slowly under physiological conditions following their intranasal delivery (e.g., at the nasal mucosal surface, or in the presence of bodily fluids following transmucosal delivery). Appropriate binders include but are not limited to biocompatible polymers and copolymers previously used in the art in sustained release formulations. Such biocompatible compounds are non-toxic and inert to surrounding tissues, and do not trigger significant adverse side effects such as nasal irritation, immune response, inflammation, or the like. They are metabolized into metabolic products that are also biocompatible and easily eliminated from the body.

Exemplary polymeric materials for use in this context include, but are not limited to, polymeric matrices derived from copolymeric and homopolymeric polyesters having hydrolysable ester linkages. A number of these are known in the art to be biodegradable and to lead to degradation products having no or low toxicity. Exemplary polymers include polyglycolic acids (PGA) and polylactic acids (PLA), poly(DL-lactic acid-co-glycolic acid)(DL PLGA), poly(D-lactic acid-coglycolic acid)(D PLGA) and poly(L-lactic acid-co-glycolic acid)(L PLGA). Other useful biodegradable or bioerodable polymers include but are not limited to such polymers as poly(epsilon-caprolactone), poly(epsilon-aprolactone-CO-lactic acid), poly(ϵ-aprolactone-CO-glycolic acid), poly(beta-hydroxy butyric acid), poly(alkyl-2-cyanoacrilate), hydrogels such as poly(hydroxyethyl methacrylate), polyamides, poly(amino acids) (i.e., L-leucine, glutamic acid, L-aspartic acid and the like), poly (ester urea), poly (2-hydroxyethyl DL-aspartamide), polyacetal polymers, polyorthoesters, polycarbonate, polymaleamides, polysaccharides and copolymers thereof. Many methods for preparing such formulations are generally known to those skilled in the art. Other useful formulations include controlled-release compositions e.g., microcapsules, U.S. Pat. Nos. 4,652,441 and 4,917,893, lactic acid-glycolic acid copolymers useful in making microcapsules and other formulations, U.S. Pat. Nos. 4,677,191 and 4,728,721, and sustained-release compositions for water-soluble peptides, U.S. Pat. No. 4,675,189.

Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders, methods of preparation include vacuum drying and freeze-drying which yields a powder of the active ingredient plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

Mucosal administration according to the invention allows effective self-administration of treatment by patients, provided that sufficient safeguards are in place to control and monitor dosing and side effects. Mucosal administration also overcomes certain drawbacks of other administration forms, such as injections, that are painful and expose the patient to possible infections and may present drug bioavailability problems. For nasal and pulmonary delivery, systems for controlled aerosol dispensing of therapeutic liquids as a spray are well known. In one embodiment, metered doses of active agent are delivered by means of a specially constructed mechanical pump valve, U.S. Pat. No. 4,511,069.

Dosage

For prophylactic and treatment purposes, the biologically active agent(s) disclosed herein may be administered to the subject in a single bolus delivery, via continuous delivery (e.g., continuous transdermal, mucosal, or intravenous delivery) over an extended time period, or in a repeated administration protocol (e.g., by an hourly, daily or weekly, repeated administration protocol). In this context, a therapeutically effective dosage of the Y2 receptor-binding peptide may include repeated doses within a prolonged prophylaxis or treatment regimen that will yield clinically significant results to alleviate one or more symptoms or detectable conditions associated with a targeted disease or condition as set forth above. Determination of effective dosages in this context is typically based on animal model studies followed up by human clinical trials and is guided by determining effective dosages and administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

The actual dosage of biologically active agents will of course vary according to factors such as the disease indication and particular status of the subject (e.g., the subject's age, size, fitness, extent of symptoms, susceptibility factors, etc), time and route of administration, other drugs or treatments being administered concurrently, as well as the specific pharmacology of the biologically active agent(s) for eliciting the desired activity or biological response in the subject. Dosage regimens may be adjusted to provide an optimum prophylactic or therapeutic response. A therapeutically effective amount is also one in which any toxic or detrimental side effects of the biologically active agent are outweighed in clinical terms by therapeutically beneficial effects. A non-limiting range for a therapeutically effective amount of an Y2 agonist within the methods and formulations of the invention is 0.7 μg/kg to about 25 μg/kg. To promote weight loss, an intranasal dose of Y2 receptor-binding peptide is administered at dose high enough to promote satiety but low enough so as not to induce any unwanted side-effects such as nausea. A preferred intranasal dose of $PYY_{3-36}$ is about 1 μg–10 μg/kg weight of the patient, most preferably from about 1.5 μg/kg to about 3 μg/kg weight of the patient. In a standard dose a patient will receive 50 μg to 1600 μg, more preferably about between 75 μg to 800 μg, most preferably 100 μg, 150 μg, 200 μg to about 400 μg. Alternatively, a non-limiting range for a therapeutically effective amount of a biologically active agent within the methods and formulations of the invention is between about 0.001 pmol to about 100 pmol per kg body weight, between about 0.01 pmol to about 10 pmol per kg body weight, between about 0.1 pmol to about 5 pmol per kg body weight, or between about 0.5 pmol to about 1.0 pmol per kg body weight. Dosages within this range can be achieved by single or multiple administrations, including, e.g., multiple administrations per day, daily or weekly administrations. Per administration, it is desirable to administer at least one microgram of the biologically active agent (e.g., one or more Y2 receptor-binding peptide proteins, analogs and mimetics, and other biologically active agents), more typically between about 10 μg and 5.0 mg, and in certain embodiments between about 100 μg and 1.0 or 2.0 mg to an average human subject. For certain oral applications, doses as high as 0.5 mg per kg body weight may be necessary to achieve adequate plasma levels. It is to be further noted that for each particular subject, specific dosage regimens should be evaluated and adjusted over time according to the individual need and professional judgment of the person administering or supervising the administration of the permeabilizing peptide(s) and other biologically active agent(s). In a standard dose a patient will receive 40 μg to 200 μg, more preferably about between 45 μg to 150 μg, 50 μg to about 100 μg or perhaps a dose ranging from 65 to about 75 μg of PYY3–36 depending on the individual. Repeated intranasal dosing with the formulations of the invention, on a schedule ranging from about 0.1 to 24 hours between doses, preferably between 0.5 and 24.0 hours between doses, will maintain normalized, sustained therapeutic levels of Y2 receptor-binding peptide to maximize clinical benefits while minimizing the risks of excessive exposure and side effects. This dose can be administered several times a day to promote satiety, preferably one half hour before a meal or when hunger occurs. The goal is to mucosally deliver an amount of the Y2 receptor-binding peptide sufficient to raise the concentration of the Y2 receptor-binding peptide in the plasma of an individual to mimic the concentration that would normally occur postprandially, i.e., after the individual has finished eating.

Dosage of Y2 agonists such as PYY may be varied by the attending clinician or patient, if self administering an over the counter dosage form, to maintain a desired concentration at the target site.

In an alternative embodiment, the invention provides compositions and methods for intranasal delivery of Y2 receptor-binding peptide, wherein the Y2 receptor-binding peptide compound(s) is/are repeatedly administered through an intranasal effective dosage regimen that involves multiple administrations of the Y2 receptor-binding peptide to the subject during a daily or weekly schedule to maintain a therapeutically effective elevated and lowered pulsatile level of Y2 receptor-binding peptide during an extended dosing period. The compositions and method provide Y2 receptor-binding peptide compound(s) that are self-administered by the subject in a nasal formulation between one and six times daily to maintain a therapeutically effective elevated and lowered pulsatile level of Y2 receptor-binding peptide during an 8 hour to 24 hour extended dosing period.

Kits

The instant invention also includes kits, packages and multicontainer units containing the above described pharmaceutical compositions, active ingredients, and/or means for administering the same for use in the prevention and treatment of diseases and other conditions in mammalian subjects. Briefly, these kits include a container or formulation that contains one or more Y2 receptor-binding peptide proteins, analogs or mimetics, and/or other biologically active agents in combination with mucosal delivery enhancing agents disclosed herein formulated in a pharmaceutical preparation for mucosal delivery.

The intranasal formulations of the present invention can be administered using any spray bottle or syringe. An example of a nasal spray bottle is the, "Nasal Spray Pump w/Safety Clip, Pfeiffer SAP #60548, which delivers a dose of 0.1 mL per squirt and has a diptube length of 36.05 mm. It can be purchased from Pfeiffer of America of Princeton, N.J. Intranasal doses of a Y2 receptor-binding peptide such as PYY can range from 0.1 μg/kg to about 1500 μg/kg. When administered in as an intranasal spray, it is preferable that the particle size of the spray are between 10–100 μm (microns) in size, preferably 20–100 μm in size.

To promote weight loss, an intranasal dose of a Y2 receptor-binding peptide PYY is administered at dose high enough to promote satiety but low enough so as not to induce any unwanted side-effects such as nausea. A preferred intranasal dose of a Y2 receptor-binding peptide such as PYY(3–36) is about 3 μg–10 μg/kg weight of the patient, most preferably about 6 μg/kg weight of the patient. In a standard dose a patient will receive 40 μg to 200 μg, more preferably about between 45 μg to 150 μg, 50 μg to about 100 μg. The a Y2 receptor-binding peptide such as PYY (3–36) is preferably administered at least ten minutes to one hour prior to eating to prevent nausea but no more than about twelve to twenty-four hours prior to eating. The patient is dosed at least once a day preferably before every meal until the patient has lost a desired amount of weight. The patient then receives maintenance doses at least once a week preferably daily to maintain the weight loss."

As is shown by the data from the following examples, when administered intranasally to humans using the Y2 receptor-binding peptide formulation of the present invention, PYY(3–36) was found to reduce appetite. The examples also show that for the first time post-prandial physiological levels of a PYY peptide could be reached through an intranasal route of administration using the Y2 receptor-binding peptide formulations of the present invention in which PYY(3–36) was the Y2 receptor-binding peptide.

Aerosol Nasal Administration of PYY

We have discovered that the Y2 receptor-binding peptides can be administered intranasally using a nasal spray or aerosol. This is surprising because many proteins and peptides have been shown to be sheared or denatured due to the mechanical forces generated by the actuator in producing the spray or aerosol. In this area the following definitions are useful.

1. Aerosol—A product that is packaged under pressure and contains therapeutically active ingredients that are released upon activation of an appropriate valve system.
2. Metered aerosol—A pressurized dosage form comprised of metered dose valves, which allow for the delivery of a uniform quantity of spray upon each activation.
3. Powder aerosol—A product that is packaged under pressure and contains therapeutically active ingredients in the form of a powder, which are released upon activation of an appropriate valve system.
4. Spray aerosol—An aerosol product that utilizes a compressed gas as the propellant to provide the force necessary to expel the product as a wet spray; it generally applicable to solutions of medicinal agents in aqueous solvents.
5. Spray—A liquid minutely divided as by a jet of air or steam. Nasal spray drug products contain therapeutically active ingredients dissolved or suspended in solutions or mixtures of excipients in nonpressurized dispensers.
6. Metered spray—A non-pressurized dosage form consisting of valves that allow the dispensing of a specified quantity of spray upon each activation.
7. Suspension spray—A liquid preparation containing solid particles dispersed in a liquid vehicle and in the form of course droplets or as finely divided solids.

The fluid dynamic characterization of the aerosol spray emitted by metered nasal spray pumps as a drug delivery device ("DDD"). Spray characterization is an integral part of the regulatory submissions necessary for Food and Drug Administration ("FDA") approval of research and development, quality assurance and stability testing procedures for new and existing nasal spray pumps.

Thorough characterization of the spray's geometry has been found to be the best indicator of the overall performance of nasal spray pumps. In particular, measurements of the spray's divergence angle (plume geometry) as it exits the device; the spray's cross-sectional ellipticity, uniformity and particle/droplet distribution (spray pattern); and the time evolution of the developing spray have been found to be the most representative performance quantities in the characterization of a nasal spray pump. During quality assurance and stability testing, plume geometry and spray pattern measurements are key identifiers for verifying consistency and conformity with the approved data criteria for the nasal spray pumps.

Definitions

Plume Height—the measurement from the actuator tip to the point at which the plume angle becomes non-linear because of the breakdown of linear flow. Based on a visual examination of digital images, and to establish a measurement point for width that is consistent with the farthest measurement point of spray pattern, a height of 30 mm is defined for this study Major Axis—the largest chord that can be drawn within the fitted spray pattern that crosses the COMw in base units (mm)

Minor Axis—the smallest chord that can be drawn within the fitted spray pattern that crosses the COMw in base units (mm)

Ellipticity Ratio—the ratio of the major axis to the minor axis, preferably between 1.0 and 1.5, and most preferably between 1.0 and 1.3.

$D_{10}$—the diameter of droplet for which 10% of the total liquid volume of sample consists of droplets of a smaller diameter (μm)

$D_{50}$—the diameter of droplet for which 50% of the total liquid volume of sample consists of droplets of a smaller diameter (μm), also known as the mass median diameter $D_{90}$—the diameter of droplet for which 90% of the total liquid volume of sample consists of droplets of a smaller diameter (μm)

Span—measurement of the width of the distribution, The smaller the value, the narrower the distribution. Span is calculated as $$\frac{(D_{90} - D_{10})}{D_{50}}.$$

% RSD—percent relative standard deviation, the standard deviation divided by the mean of the series and multiplied by 100, also known as % CV.

Volume—the volume of liquid or powder discharged from the delivery device with each actuation, preferably between 0.01 mL and about 2.5 mL and most preferably between 0.02 mL and 0.25 mL.

FIGS. 21A and 21B show a nasal spray device 10 before engagement (FIG. 21A) and after engagement (FIG. 21B). The nasal spray bottle 10 is comprised of a bottle 12 into which is the nasal Y2 receptor-binding peptide formulation is placed, and an actuator 14, which when actuated or engage forces a spray plume, 16, of the Y2 receptor-binding peptide out of the spray bottle, 12, through the actuator, 14. A spray pattern is determined by taking a photograph of a cross-section of the spray plume 16 above a predetermined height, 18, of the plume. The spray plume also has angle of ejection, 20, as it leaves actuator, 14. A spray pattern of spray plume 16 is shown on FIG. 22. Spray pattern 22, is elliptical and has a major axis, 24, and a minor axis 26.

The following examples are provided by way of illustration, not limitation.

EXAMPLE 1

An exemplary formulation for enhanced nasal mucosal delivery of peptide YY following the teachings of the instant specification was prepared and evaluated as follows:

TABLE 1

Peptide YY formulation composition

| Formulations | Peptide YY$_{3-36}$ Per 100 ml Sample | Mucosal Delivery Enhancing Agent |
|---|---|---|
| A | 60 μg | Phosphate-buffered saline (0.8%) pH 7.4 (Control 1) |
| B | 60 μg | Phosphate-buffered saline (0.8%) pH 5.0 (Control 2) |
| C | 60 μg | L-Arginine (10% w/v) |
| D | 60 μg | Poly-L-Arginine (0.5% w/v) |
| E | 60 μg | Gamma-Cyclodextrin (1% w/v) |
| F | 60 μg | α-Cyclodextrin (5% w/v) |
| G | 60 μg | Methyl-β-Cyclodextrin (3% w/v) |
| H | 60 μg | n-Capric Acid Sodium (0.075% w/v) |
| I | 60 μg | Chitosan (0.5% w/v) |
| J | 60 μg | L-α-phosphatidylcholine didecanoyl (3.5% w/v) |
| K | 60 μg | S-Nitroso-N-Acetyl-Penicillamine (0.5% w/v) |
| L | 60 μg | Palmotoyl-DL-Carnitine (0.02% w/v) |
| M | 60 μg | Pluronic-127 (0.3% w/v) |
| N | 60 μg | Sodium Nitroprusside (0.3% w/v) |
| O | 60 μg | Sodium Glycocholate (1% w/v) |
| P | 60 μg | F1: Gelatin, DDPC, MBCD, EDTA |
| F1 | | L-α-phosphatidylcholine didecanoyl (0.5% w/v) Methyl β Cyclodextrin (3% w/v) EDTA (0.1% w/v, Inf. Conc. 0.5 M) Gelatin (0.5% w/v) |

EXAMPLE 2

Nasal Mucosal Delivery—Permeation Kinetics and Cytotoxicity

1. Organotypic Model

The following methods are generally useful for evaluating nasal mucosal delivery parameters, kinetics and side effects for peptide YY within the formulations and method of the invention, as well as for determining the efficacy and characteristics of the various intranasal delivery-enhancing agents disclosed herein for combinatorial formulation or coordinate administration with peptide YY.

Permeation kinetics and cytotoxicity are also useful for determining the efficacy and characteristics of the various mucosal delivery-enhancing agents disclosed herein for combinatorial formulation or coordinate administration with mucosal delivery-enhancing agents. In one exemplary protocol, permeation kinetics and lack of unacceptable cytotoxicity are demonstrated for an intranasal delivery-enhancing agent as disclosed above in combination with a biologically active therapeutic agent, exemplified by peptide YY.

The EpiAirway system was developed by MatTek Corp (Ashland, Mass.) as a model of the pseudostratified epithelium lining the respiratory tract. The epithelial cells are grown on porous membrane-bottomed cell culture inserts at an air-liquid interface, which results in differentiation of the cells to a highly polarized morphology. The apical surface is ciliated with a microvillous ultrastructure and the epithelium produces mucus (the presence of mucin has been confirmed by immunoblotting). The inserts have a diameter of 0.875 cm, providing a surface area of 0.6 cm². The cells are plated onto the inserts at the factory approximately three weeks before shipping. One "kit" consists of 24 units.

A. On arrival, the units are placed onto sterile supports in 6-well microplates. Each well receives 5 mL of proprietary culture medium. This DMEM-based medium is serum free but is supplemented with epidermal growth factor and other factors. The medium is always tested for endogenous levels of any cytokine or growth factor, which is being considered for intranasal delivery, but has been free of all cytokines and factors studied to date except insulin. The 5 mL volume is just sufficient to provide contact to the bottoms of the units on their stands, but the apical surface of the epithelium is allowed to remain in direct contact with air. Sterile tweezers are used in this step and in all subsequent steps involving transfer of units to liquid-containing wells to ensure that no air is trapped between the bottoms of the units and the medium.

B. The units in their plates are maintained at 37° C. in an incubator in an atmosphere of 5% $CO_2$ in air for 24 hours. At the end of this time the medium is replaced with fresh medium and the units are returned to the incubator for another 24 hours.

2. Experimental Protocol—Permeation Kinetics

A. A "kit" of 24 EpiAirway units can routinely be employed for evaluating five different formulations, each of which is applied to quadruplicate wells. Each well is employed for determination of permeation kinetics (4 time points), transepithelial resistance, mitochondrial reductase activity as measured by MTT reduction, and cytolysis as measured by release of LDH. An additional set of wells is employed as controls, which are sham treated during determination of permeation kinetics, but are otherwise handled identically to the test sample-containing units for determinations of transepithelial resistance and viability. The determinations on the controls are routinely also made on quadruplicate units, but occasionally we have employed triplicate units for the controls and have dedicated the remaining four units in the kit to measurements of transepithelial resistance and viability on untreated units or we have frozen and thawed the units for determinations of total LDH levels to serve as a reference for 100% cytolysis.

B. In all experiments, the nasal mucosal delivery formulation to be studied is applied to the apical surface of each unit in a volume of 100 μL, which is sufficient to cover the entire apical surface. An appropriate volume of the test formulation at the concentration applied to the apical surface (no more than 100 μL is generally needed) is set aside for subsequent determination of concentration of the active material by ELISA or other designated assay.

C. The units are placed in 6 well plates without stands for the experiment: each well contains 0.9 mL of medium which is sufficient to contact the porous membrane bottom of the unit but does not generate any significant upward hydrostatic pressure on the unit.

D. To minimize potential sources of error and avoid any formation of concentration gradients, the units are transferred from one 0.9 mL-containing well to another at each time point in the study. These transfers are made at the following time points, based on a zero time at which the 100 μL volume of test material was applied to the apical surface: 15 minutes, 30 minutes, 60 minutes, and 120 minutes.

E. In between time points the units in their plates are kept in the 37° C. incubator. Plates containing 0.9 mL medium per well are also maintained in the incubator so that minimal change in temperature occurs during the brief periods when the plates are removed and the units are transferred from one well to another using sterile forceps.

F. At the completion of each time point, the medium is removed from the well from which each unit was transferred, and aliquotted into two tubes (one tube receives 700 µL and the other 200 µL) for determination of the concentration of permeated test material and, in the event that the test material is cytotoxic, for release of the cytosolic enzyme, lactic dehydrogenase, from the epithelium. These samples are kept in the refrigerator if the assays are to be conducted within 24 hours, or the samples are subaliquotted and kept frozen at $-80°$ C. until thawed once for assays. Repeated freeze-thaw cycles are to be avoided.

G. In order to minimize errors, all tubes, plates, and wells are prelabeled before initiating an experiment.

H. At the end of the 120 minute time point, the units are transferred from the last of the 0.9 mL containing wells to 24-well microplates, containing 0.3 mL medium per well. This volume is again sufficient to contact the bottoms of the units, but not to exert upward hydrostatic pressure on the units. The units are returned to the incubator prior to measurement of transepithelial resistance.

3. Experimental Protocol—Transepithelial Resistance

A. Respiratory airway epithelial cells form tight junctions in vivo as well as in vitro, restricting the flow of solutes across the tissue. These junctions confer a transepithelial resistance of several hundred $ohms \times cm^2$ in excised airway tissues; in the MatTek EpiAirway units, the transepithelial resistance (TER) is claimed by the manufacturer to be routinely around 1000 $ohms \times cm^2$. We have found that the TER of control EpiAirway units which have been sham-exposed during the sequence of steps in the permeation study is somewhat lower (700–800 $ohms \times cm^2$), but, since permeation of small molecules is proportional to the inverse of the TER, this value is still sufficiently high to provide a major barrier to permeation. The porous membrane-bottomed units without cells, conversely, provide only minimal transmembrane resistance (5–20 $ohms \times cm^2$).

B. Accurate determinations of TER require that the electrodes of the ohmmeter be positioned over a significant surface area above and below the membrane, and that the distance of the electrodes from the membrane be reproducibly controlled. The method for TER determination recommended by MatTek and employed for all experiments here employs an "EVOM"™ epithelial voltohmmeter and an "ENDOHM"™ tissue resistance measurement chamber from World Precision Instruments, Inc., Sarasota, Fla.

C. The chamber is initially filled with Dulbecco's phosphate buffered saline (PBS) for at least 20 minutes prior to TER determinations in order to equilibrate the electrodes.

D. Determinations of TER are made with 1.5 mL of PBS in the chamber and 350 µL of PBS in the membrane-bottomed unit being measured. The top electrode is adjusted to a position just above the membrane of a unit containing no cells (but containing 350 µL of PBS) and then fixed to ensure reproducible positioning. The resistance of a cell-free unit is typically 5–20 $ohms \times cm^2$ ("background resistance").

E. Once the chamber is prepared and the background resistance is recorded, units in a 24-well plate which had just been employed in permeation determinations are removed from the incubator and individually placed in the chamber for TER determinations.

F. Each unit is first transferred to a petri dish containing PBS to ensure that the membrane bottom is moistened. An aliquot of 350 µL PBS is added to the unit and then carefully aspirated into a labeled tube to rinse the apical surface. A second wash of 350 µL PBS is then applied to the unit and aspirated into the same collection tube.

G. The unit is gently blotted free of excess PBS on its exterior surface only before being placed into the chamber (containing a fresh 1.5 mL aliquot of PBS). An aliquot of 350 µL PBS is added to the unit before the top electrode is placed on the chamber and the TER is read on the EVOM meter.

H. After the TER of the unit is read in the ENDOHM chamber, the unit is removed, the PBS is aspirated and saved, and the unit is returned with an air interface on the apical surface to a 24-well plate containing 0.3 mL medium per well.

I. The units are read in the following sequence: all sham-treated controls, followed by all formulation-treated samples, followed by a second TER reading of each of the sham-treated controls. After all the TER determinations are complete, the units in the 24-well microplate are returned to the incubator for determination of viability by MTT reduction.

4. Experimental Protocol—Viability by MTT Reduction

MTT is a cell-permeable tetrazolium salt which is reduced by mitochondrial dehydrogenase activity to an insoluble colored formazan by viable cells with intact mitochondrial function or by nonmitochondrial NAD(P)H dehydrogenase activity from cells capable of generating a respiratory burst. Formation of formazan is a good indicator of viability of epithelial cells since these cells do not generate a significant respiratory burst. We have employed a MTT reagent kit prepared by MatTek Corp for their units in order to assess viability.

A. The MTT reagent is supplied as a concentrate and is diluted into a proprietary DMEM-based diluent on the day viability is to be assayed (typically the afternoon of the day in which permeation kinetics and TER were determined in the morning). Insoluble reagent is removed by a brief centrifugation before use. The final MTT concentration is 1 mg/mL B. The final MTT solution is added to wells of a 24-well microplate at a volume of 300 µL per well. As has been noted above, this volume is sufficient to contact the membranes of the EpiAirway units but imposes no significant positive hydrostatic pressure on the cells.

C. The units are removed from the 24-well plate in which they were placed after TER measurements, and after removing any excess liquid from the exterior surface of the units, they are transferred to the plate containing MTT reagent. The units in the plate are then placed in an incubator at 37° C. in an atmosphere of 5% $CO_2$ in air for 3 hours.

D. At the end of the 3-hour incubation, the units containing viable cells will have turned visibly purple. The insoluble formazan must be extracted from the cells in their units to quantitate the extent of MTT reduction. Extraction of the formazan is accomplished by transferring the units to a 24-well microplate containing 2 mL extractant solution per well, after removing excess liquid from the exterior surface of the units as before. This volume is sufficient to completely cover both the membrane and the apical surface of the units. Extraction is allowed to proceed overnight at room temperature in a light-tight chamber. MTT extractants traditionally contain high concentrations of detergent, and destroy the cells.

E. At the end of the extraction, the fluid from within each unit and the fluid in its surrounding well are combined and transferred to a tube for subsequent aliquotting into a 96-well microplate (200 µL aliquots are optimal) and determination of absorbance at 570 nm on a VMax multiwell microplate spectrophotometer. To ensure that turbidity from debris coming from the extracted units does not contribute to the absorbance, the absorbance at 650 nm is also determined for each well in the VMax and is automatically subtracted from the absorbance at 570 nm. The "blank" for the determination of formazan absorbance is a 200 µL aliquot of extractant to which no unit had been exposed. This absorbance value is assumed to constitute zero viability.

F. Two units from each kit of 24 EpiAirway units are left untreated during determination of permeation kinetics and TER. These units are employed as the positive control for 100% cell viability. In all the studies we have conducted, there has been no statistically significant difference in the viability of the cells in these untreated units vs. cells in control units which had been sham treated for permeation kinetics and on which TER determinations had been performed. The absorbance of all units treated with test formulations is assumed to be linearly proportional to the percent viability of the cells in the units at the time of the incubation with MTT. It should be noted that this assay is carried out typically no sooner than four hours after introduction of the test material to the apical surface, and subsequent to rinsing of the apical surface of the units during TER determination.

5. Determination of Viability by LDH Release

While measurement of mitochondrial reductase activity by MTT reduction is a sensitive probe of cell viability, the assay necessarily destroys the cells and therefore can be carried out only at the end of each study. When cells undergo necrotic lyses, their cytotosolic contents are spilled into the surrounding medium, and cytosolic enzymes such as lactic dehydrogenase (LDH) can be detected in this medium. An assay for LDH in the medium can be performed on samples of medium removed at each time point of the two-hour determination of permeation kinetics. Thus, cytotoxic effects of formulations which do not develop until significant time has passed can be detected as well as effects of formulations which induce cytolysis with the first few minutes of exposure to airway epithelium.

A. The recommended LDH assay for evaluating cytolysis of the EpiAirway units is based on conversion of lactate to pyruvate with generation of NADH from NAD. The NADH is then reoxidized along with simultaneous reduction of the tetrazolium salt INT, catalyzed by a crude "diaphorase" preparation. The formazan formed from reduction of INT is soluble, so that the entire assay for LDH activity can be carried out in a homogenous aqueous medium containing lactate, NAD, diaphorase, and INT.

B. The assay for LDH activity is carried out on 50 µL aliquots from samples of "supernatant" medium surrounding an EpiAirway unit and collected at each time point. These samples were either stored for no longer than 24 h in the refrigerator or were thawed after being frozen within a few hours after collection. Each EpiAirway unit generates samples of supernatant medium collected at 15 min, 30 min, 1 h, and 2 h after application of the test material. The aliquots are all transferred to a 96 well microplate.

C. A 50 µL aliquot of medium which had not been exposed to a unit serves as a "blank" or negative control of 0% cytotoxicity. We have found that the apparent level of "endogenous" LDH present after reaction of the assay reagent mixture with the unexposed medium is the same within experimental error as the apparent level of LDH released by all the sham-treated control units over the entire time course of 2 hours required to conduct a permeation kinetics study. Thus, within experimental error, these sham-treated units show no cytolysis of the epithelial cells over the time course of the permeation kinetics measurements.

D. To prepare a sample of supernatant medium reflecting the level of LDH released after 100% of the cells in a unit have lysed, a unit which had not been subjected to any prior manipulations is added to a well of a 6-well microplate containing 0.9 mL of medium as in the protocol for determination of permeation kinetics, the plate containing the unit is frozen at −80° C., and the contents of the well are then allowed to thaw. This freeze-thaw cycle effectively lyses the cells and releases their cytosolic contents, including LDH, into the supernatant medium. A 50 µL aliquot of the medium from the frozen and thawed cells is added to the 96-well plate as a positive control reflecting 100% cytotoxicity.

E. To each well containing an aliquot of supernatant medium, a 50 µL aliquot of the LDH assay reagent is added. The plate is then incubated for 30 minutes in the dark.

F. The reactions are terminated by addition of a "stop" solution of 1 M acetic acid, and within one hour of addition of the stop solution, the absorbance of the plate is determined at 490 nm.

G. Computation of percent cytolysis is based on the assumption of a linear relationship between absorbance and cytolysis, with the absorbance obtained from the medium alone serving as a reference for 0% cytolysis and the absorbance obtained from the medium surrounding a frozen and thawed unit serving as a reference for 100% cytolysis.

6. ELISA Determinations

The procedures for determining the concentrations of biologically active agents as test materials for evaluating enhanced permeation of active agents in conjunction with coordinate administration of mucosal delivery-enhancing agents or combinatorial formulation of the invention are generally as described above and in accordance with known methods and specific manufacturer instructions of ELISA kits employed for each particular assay. Permeation kinetics of the biologically active agent is generally determined by taking measurements at multiple time points (for example 15 min., 30 min., 60 min. and 120 min) after the biologically active agent is contacted with the apical epithelial cell surface (which may be simultaneous with, or subsequent to, exposure of the apical cell surface to the mucosal delivery-enhancing agent(s)).

The procedures for determining the concentrations of peptide YY neuropeptide Y, and pancreatic peptide in blood serum, central nervous system (CNS) tissues or fluids, cerebral spinal fluid (CSF), or other tissues or fluids of a mammalian subject may be determined by immunologic assay for peptide YY neuropeptide Y, and pancreatic peptide. The procedures for determining the concentrations of peptide YY neuropeptide Y, and pancreatic peptide as test materials for evaluating enhanced permeation of active agents in conjunction with coordinate administration of mucosal delivery-enhancing agents or combinatorial formulation of the invention are generally as described above and in accordance with known methods and specific manufacturer instructions for radioimmunoassay (RIA), enzyme immunoassay (EIA), and antibody reagents for immunohistochemistry or immunofluorescence for peptide YY neuropeptide Y, and pancreatic peptide. Bachem A G (King of Prussia, Pa.).

EpiAirway™ tissue membranes are cultured in phenol red and hydrocortisone free medium (MatTek Corp., Ashland, Mass.). The tissue membranes are cultured at 37° C. for 48 hours to allow the tissues to equilibrate. Each tissue membrane is placed in an individual well of a 6-well plate containing 0.9 mL of serum free medium. 100 µL of the formulation (test sample or control) is applied to the apical surface of the membrane. Triplicate or quadruplicate samples of each test sample (mucosal delivery-enhancing agent in combination with a biologically active agent, peptide YY) and control (biologically active agent, peptide YY, alone) are evaluated in each assay. At each time point (15, 30, 60 and 120 minutes) the tissue membranes are moved to new wells containing fresh medium. The underlying 0.9 mL medium samples is harvested at each time point and stored at 4° C. for use in ELISA and lactate dehydrogenase (LDH) assays.

The ELISA kits are typically two-step sandwich ELISAs: the immunoreactive form of the agent being studied is first "captured" by an antibody immobilized on a 96-well microplate and after washing unbound material out of the wells, a "detection" antibody is allowed to react with the bound immunoreactive agent. This detection antibody is typically conjugated to an enzyme (most often horseradish peroxidase) and the amount of enzyme bound to the plate in immune complexes is then measured by assaying its activity with a chromogenic reagent. In addition to samples of supernatant medium collected at each of the time points in the permeation kinetics studies, appropriately diluted samples of the formulation (i.e., containing the subject biologically active test agent) that was applied to the apical surface of the units at the start of the kinetics study are also assayed in the ELISA plate, along with a set of manufacturer-provided standards. Each supernatant medium sample is generally assayed in duplicate wells by ELISA (it will be recalled that quadruplicate units are employed for each formulation in a permeation kinetics determination, generating a total of sixteen samples of supernatant medium collected over all four time points).

A. It is not uncommon for the apparent concentrations of active test agent in samples of supernatant medium or in diluted samples of material applied to the apical surface of the units to lie outside the range of concentrations of the standards after completion of an ELISA. No concentrations of material present in experimental samples are determined by extrapolation beyond the concentrations of the standards; rather, samples are rediluted appropriately to generate concentrations of the test material which can be more accurately determined by interpolation between the standards in a repeat ELISA.

B. The ELISA for a biologically active test agent, for example, peptide YY, is unique in its design and recommended protocol. Unlike most kits, the ELISA employs two monoclonal antibodies, one for capture and another, directed towards a nonoverlapping determinant for the biologically active test agent, e.g., peptide YY, as the detection antibody (this antibody is conjugated to horseradish peroxidase). As long as concentrations of peptide YY that lie below the upper limit of the assay are present in experimental samples, the assay protocol can be employed as per the manufacturer's instructions, which allow for incubation of the samples on the ELISA plate with both antibodies present simultaneously. When the peptide YY levels in a sample are significantly higher than this upper limit, the levels of immunoreactive peptide YY may exceed the amounts of the antibodies in the incubation mixture, and some peptide YY which has no detection antibody bound will be captured on the plate, while some peptide YY which has detection antibody bound may not be captured. This leads to serious underestimation of the peptide YY levels in the sample (it will appear that the peptide YY levels in such a sample lie significantly below the upper limit of the assay). To eliminate this possibility, the assay protocol has been modified:

B.1. The diluted samples are first incubated on the ELISA plate containing the immobilized capture antibody for one hour in the absence of any detection antibody. After the one hour incubation, the wells are washed free of unbound material.

B.2. The detection antibody is incubated with the plate for one hour to permit formation of immune complexes with all captured antigen. The concentration of detection antibody is sufficient to react with the maximum level of peptide YY which has been bound by the capture antibody. The plate is then washed again to remove any unbound detection antibody.

B.3. The peroxidase substrate is added to the plate and incubated for fifteen minutes to allow color development to take place.

B.4. The "stop" solution is added to the plate, and the absorbance is read at 450 nm as well as 490 nm in the VMax microplate spectrophotometer. The absorbance of the colored product at 490 nm is much lower than that at 450 nm, but the absorbance at each wavelength is still proportional to concentration of product. The two readings ensure that the absorbance is linearly related to the amount of bound peptide YY over the working range of the VMax instrument (we routinely restrict the range from 0 to 2.5 OD, although the instrument is reported to be accurate over a range from 0 to 3.0 OD). The amount of peptide YY in the samples is determined by interpolation between the OD values obtained for the different standards included in the ELISA. Samples with OD readings outside the range obtained for the standards are rediluted and run in a repeat ELISA.

Results

Measurement of transepithelial resistance by TER Assay: After the final assay time points, membranes were placed in individual wells of a 24 well culture plate in 0.3 mL of clean medium and the trans epithelial electrical resistance (TER) was measured using the EVOM Epithelial Voltohmmeter and an Endohm chamber (World Precision Instruments, Sarasota, Fla.). The top electrode was adjusted to be close to, but not in contact with, the top surface of the membrane. Tissues were removed, one at a time, from their respective wells and basal surfaces were rinsed by dipping in clean PBS. Apical surfaces were gently rinsed twice with PBS. The tissue unit was placed in the Endohm chamber, 250 μL of PBS added to the insert, the top electrode replaced and the resistance measured and recorded. Following measurement, the PBS was decanted and the tissue insert was returned to the culture plate. All TER values are reported as a function of the surface area of the tissue.

The final numbers were calculated as:

TER of cell membrane=(Resistance ($R$) of Insert with membrane–$R$ of blank Insert)×Area of membrane (0.6 cm$^2$).

Exemplary peptide YY formulation, Formulation P, showed the greatest decrease in cell membrane resistance. (Table 2). The results indicate that the exemplary formulation (e.g., Formulation P) reduces the resistance of the membrane to less than 1% of the control at the concentrations tested. The values shown are the average of three replicates of each formulation. Formulations A and B are controls prepared by reconstituting peptide YY (Bachem A G, King of Prussia, Pa.) containing 60 μg peptide $Y_{3-36}$ in 100 ml of phosphate buffered saline (PBS) at pH 7.4 or 5.0. Peptide YY without mucosal delivery enhancers did not decrease the resistance.

The results indicate that an exemplary formulation for enhanced intranasal delivery of peptide YY (e.g., Formulation P) decreases cell membrane resistance and significantly increases mucosal epithelial cells permeability. The exemplary formulations will enhance intranasal delivery of peptide YY to the blood serum or to the central nervous system tissue or fluid. The results indicate that these exemplary formulations when contacted with a mucosal epithelium yield significant increases in mucosal epithelial cell permeability to peptide YY.

TABLE 2

Influence of Pharmaceutical Formulations Comprising Peptide YY and Intranasal Delivery-Enhancing Agents on Transepithelial Resistance (TER) of EpiAirway Cell Membrane

| Formulation | Mucosal Delivery Enhancing Agent | % TER |
|---|---|---|
| A | PBS pH 7.4 (Control 1) | 100 |
| B | PBS pH 5.0 (Control 2) | 100 |
| C | L-Arginine (10% w/v) | 47.88 |
| D | Poly-L-Arginine (0.5% w/v) | 3.96 |
| E | Gamma-Cyclodextrin (1% w/v) | 91.67 |
| F | Alpha-Cyclodextrin (5% w/v) | 88.91 |
| G | Methyl-β-Cyclodextrin (3% w/v) | 97.51 |
| H | n-Capric Acid Sodium (0.075% w/v) | 47.72 |
| I | Chitosan (0.5% w/v) | 4.77 |
| J | L-α-phosphatidylcholine didecanoyl (3.5% w/v) | 0.49 |
| K | S-Nitroso-N-Acetyl-Penicillamine (0.5% w/v) | 44.35 |
| L | Palmotoyl-DL-Carnitine (0.02% w/v) | 1.76 |
| M | Pluronic-127 (0.3% w/v) | 97.57 |
| N | Sodium Nitroprusside (0.3% w/v) | 92.41 |
| O | Sodium Glycocholate (1% w/v) | 14.25 |
| P | F1: Gelatin, DDPC, MBCD, EDTA | 0.65 |

Permeation kinetics as measured by ELISA Assay: The effect of pharmaceutical formulations of the present invention comprising peptide YY and intranasal delivery-enhancing agents on the permeation of peptide YY across the EpiAirway™ Cell Membrane (mucosal epithelial cell layer) is measured as described above. The results are shown in Table 3. Permeation of peptide YY across the EpiAirway™ Cell Membrane is measured by ELISA assay.

For the exemplary intranasal formulations (e.g., Formulation P) of the present invention, the greatest increase in peptide YY permeation occurred in Formulation P as shown in Table 3. The procedure uses an ELISA assay to determine the concentration of biologically active peptide YY that has permeated the epithelial cells into the surrounding medium over multiple time points. The results show increased permeation of peptide YY in Formulation P compared to Formulation A or B (peptide YY control formulation; 60 μg peptide $YY_{3-36}$ in 100 ml of phosphate buffered saline (PBS) at pH 7.4 or 5.0; Bachem A G, King of Prussia, Pa.). On average the cumulative increase in permeation at 120 minutes using Formulation P exemplary intranasal formulation is about 1195 fold greater than Formulations A or B controls.

TABLE 3

Influence of Pharmaceutical Formulations Comprising Peptide YY and Intranasal Delivery-Enhancing Agents on Permeation of Peptide YY through EpiAirway Cell Membrane by ELISA Assay.

| Formulation | | % Permeation at Time Points (min) | | | | | Total % Permeation | Fold Increase in Permeability |
|---|---|---|---|---|---|---|---|---|
| | Peptide $YY_{3-36}$ (60 μg/100 ml) | 0 | 15 | 30 | 60 | 120 | | |
| A | PBS pH 7.4 (Control 1) | 0 | 0.00171 | 0.00096 | 0.00451 | 0.00327 | 0.01 | 1 |
| B | PBS pH 5.0 (Control 2) | 0 | 0.00093 | 0.00048 | 0.00042 | 0.00367 | 0.01 | 1 |
| C | L-Arginine (10% w/v) | 0 | 0.00119 | 0.00277 | 0.00685 | 0.00566 | 0.02 | 2 |
| D | Poly-L-Arginine (0.5% w/v) | 0 | 0.00324 | 0.01587 | 0.10395 | 0.49656 | 0.62 | 62 |
| E | Gamma-Cyclodextrin (1% w/v) | 0 | 0.00017 | 0.00042 | 0.00028 | 0.0035 | 0 | 1 |
| F | α-Cyclodextrin (5% w/v) | 0 | 0.00031 | 0.000745 | 0.00147 | 0.0031 | 0.01 | 1 |
| G | Methyl-β-Cyclodextrin (3% w/v) | 0 | 0.00028 | 0.00038 | 0.00059 | 0.01028 | 0.01 | 1 |
| H | n-Capric Acid Sodium (0.075% w/v) | 0 | 0.0004 | 0.00131 | 0.00448 | 0.00821 | 0.01 | 1 |
| I | Chitosan (0.5% w/v) | 0 | 0.00086 | 0.01098 | 0.09749 | 0.82126 | 0.93 | 93 |
| J | L-α-phosphatidylcholine didecanoyl (3.5% w/v) | 0 | 0.00934 | 0.02 | 0.08507 | 1.9642 | 2.08 | 208 |
| K | S-Nitroso-N-Acetyl-Penicillamine (0.5% w/v) | 0 | 0.00074 | 0.0032 | 0.0688 | 0.90432 | 0.98 | 98 |
| L | Palmotoyl-DL-Carnitine (0.02% w/v) | 0 | 0.00378 | 0.03422 | 0.15141 | 1.31011 | 1.5 | 150 |
| M | Pluronic-127 (0.3% w/v) | 0 | 0.00025 | 0.00027 | 0.00066 | 0.00395 | 0.01 | 1 |
| N | Sodium Nitroprusside (0.3% w/v) | 0 | 0.00171 | 0.00114 | 0.00079 | 0.05492 | 0.05 | 5 |
| O | Sodium Glycocholate (1% w/v) | 0 | 0.00325 | 0.00313 | 0.09023 | 0.70214 | 0.8 | 80 |
| P | F1 Gelatin, DDPC, MBCD, EDTA | 0 | 0.05864 | 1.3972 | 2.9799 | 7.519 | 11.95 | 1195 |

MTT Assay: The MTT assays were performed using MTT-100, MatTek kits. 300 mL of the MTT solution was added into each well. Tissue inserts were gently rinsed with clean PBS and placed in the MTT solution. The samples were incubated at 37° C. for 3 hours. After incubation the cell culture inserts were then immersed with 2.0 mL of the extractant solution per well to completely cover each insert. The extraction plate was covered and sealed to reduce evaporation. Extraction proceeds overnight at RT in the dark. After the extraction period was complete, the extractant solution was mixed and pipetted into a 96-well microtiter plate. Triplicates of each sample were loaded, as well as extractant blanks. The optical density of the samples was then measured at 550 nm on a plate reader (Molecular Devices).

The MTT assay on an exemplary formulation for enhanced nasal mucosal delivery of peptide YY following the teachings of the instant specification (e.g., Formulation P) compared to control formulation (Formulations A or B) are shown in Table 4. The results for formulations comprising peptide YY and one or more intranasal delivery enhancing agents, for example, Formulation P (experiment performed in three replicates) indicate that there is minimal toxic effect of this exemplary embodiment on viability of the mucosal epithelial tissue.

TABLE 4

Influence of Pharmaceutical Formulations Comprising Peptide YY and Intranasal Delivery-Enhancing Agents on the Viability of EpiAirway Cell Membrane as shown by % MTT

| Formulations | Treatment | % MTT |
| --- | --- | --- |
| A | PBS pH .4 (Control 1) | 100 |
| B | PBS pH 5.0 (Control 2) | 100 |
| C | L-Arginine (10% w/v) | 91.54 |
| D | Poly-L-Arginine (0.5% w/v) | 79.39 |
| E | Gamma-Cyclodextrin (1% w/v) | 100 |
| F | α-Cyclodextrin (5% w/v) | 96.63 |
| G | Methyl-β-Cyclodextrin (3% w/v) | 100 |
| H | n-Capric Acid Sodium (0.075% w/v) | 100 |
| I | Chitosan (0.5% w/v) | 100 |
| J | L-α-phosphatidylcholine didecanoyl (3.5% w/v) | 94.25 |
| K | S-Nitroso-N-Acetyl-Penicillamine (0.5% w/v) | 97.64 |
| L | Palmotoyl-DL-Carnitine (0.02% w/v) | 91.77 |
| M | Pluronic-127 (0.3% w/v) | 100 |
| N | Sodium Nitroprusside (0.3% w/v) | 100 |
| O | Sodium Glycocholate (1% w/v) | 100 |
| P | F1: Gelatin, DDPC, MBCD, EDTA | 88.75 |

LDH Assay: The LDH assay on an exemplary formulation for enhanced nasal mucosal delivery of peptide YY following the teachings of the instant specification (e.g., Formulation P) are shown in Table 5. The results for three replicates of Formulation P indicate that there is minimal toxic effect of this exemplary embodiment on viability of the mucosal epithelial tissue.

TABLE 5

Influence of Pharmaceutical Formulations Comprising Peptide YY and Intranasal Delivery-Enhancing Agents on the Viability of EpiAirway Cell Membrane as shown by % Dead Cells (LDH Assay)

| Formulations | Treatment | % dead cells |
| --- | --- | --- |
| A | PBS pH .4 (Control 1) | 1.0 |
| B | PBS pH 5.0 (Control 2) | 1.1 |
| C | L-Arginine (10% w/v) | 0.8 |
| D | Poly-L-Arginine (0.5% w/v) | 1.4 |
| E | Gamma-Cyclodextrin (1% w/v) | 0.8 |
| F | α-Cyclodextrin (5% w/v) | 0.7 |
| G | Methyl-β-Cyclodextrin (3% w/v) | 0.8 |
| H | n-Capric Acid Sodium (0.075% w/v) | 1.3 |
| I | Chitosan (0.5% w/v) | 0.7 |
| J | L-α-phosphatidylcholine didecanoyl (3.5% w/v) | 1.2 |
| K | S-Nitroso-N-Acetyl-Penicillamine (0.5% w/v) | 0.7 |
| L | Palmotoyl-DL-Carnitine (0.02% w/v) | 0.8 |
| M | Pluronic-127 (0.3% w/v) | 1.0 |
| N | Sodium Nitroprusside (0.3% w/v) | 0.6 |
| O | Sodium Glycocholate (1% w/v) | 0.8 |
| P | F1: Gelatin, DDPC, MBCD, EDTA | 2.0 |

EXAMPLE 3

Formulation P (Peptide YY) of the Present Invention in Combination with Triamcinolone Acetonide Corticosteroid Improves Cell Viability The present example provides an in vitro study to determine the permeability and reduction in epithelial mucosal inflammation of an intranasally administered peptide YY, for example, human peptide YY, in combination with a steroid composition, for example, triamcinolone acetonide, and further in combination with one or more intranasal delivery-enhancing agents. The study involves determination of epithelial cell permeability by TER assay and reduction in epithelial mucosal inflammation as measured by cell viability in an MTT assay by application of an embodiment comprising peptide YY and triamcinolone acetonide.

Formulation P (see Table 1 above) is combined in a formulation with triamcinolone acetonide at a dosage of 0.5, 2.0, 5.0, or 50 µg. Normal dose of triamcinolone acetonide, (Nasacort®, Aventis Pharmaceuticals) for seasonal allergic rhinitis, is 55 µg per spray. Formulation P in combination with triamcinolone acetonide corticosteroid improves cell viability as measured by the MTT assay, while maintaining epithelial cell permeability as measured by TER and ELISA assays.

According to the methods and formulations of the invention, measurement of permeability of Formulation P in the presence or absence of triamcinolone acetonide is performed by transepithelial electrical resistance (TER) assays in an EpiAirway™ cell membrane. TER assays of Formulation P plus triamcinolone acetonide at a concentration of 0.5, 2.0, 5.0, or 50 µg per spray indicate that peptide YY permeability did not decrease and was equal to permeability of Formulation P alone. Formulation P plus triamcinolone acetonide at a triamcinolone acetonide concentration between 0 and 50 µg per spray is typically, at least 10-fold to 100-fold greater than permeability of Formulations A or B (peptide YY control).

According to the methods and formulations of the invention, measurement of permeability of Formulation P in the presence or absence of triamcinolone acetonide is performed by ELISA assay in an EpiAirway™ cell membrane. Similar to the TER assay above, ELISA assay of Formulation P plus triamcinolone acetonide at a concentration of 0.5, 2.0, 5.0, or 50 μg per spray indicate that peptide YY permeability did not decrease and was equal to permeability of Formulation P alone. Formulation P plus triamcinolone acetonide at a triamcinolone acetonide concentration between 0 and 50 μg per spray is typically greater than permeability of Formulations A or B (peptide YY control).

According to the methods and formulations of the invention, MTT assay measured cell viability of Formulation P in the presence or absence of triamcinolone acetonide. Typically, addition of triamcinolone acetonide (at a concentration of 0.5, 2.0, 5.0, or 50 μg per spray) to Formulation P improves cell viability compared to Formulation P in the absence of triamcinolone acetonide.

Addition of triamcinolone acetonide to Formulation P increases cell viability and maintains epithelial permeability as measured by TER assay comparable to Formulation P in the absence of triamcinolone acetonide.

Reduction in epithelial mucosal inflammation of an intranasally administered peptide YY is accomplished with an intranasal formulation of peptide YY in combination with one or more steroid or corticosteroid compound(s) typically high potency compounds or formulations, but also in certain cases medium potency, or low potency compounds or formulations. Overall potency (equivalent dosages) of high, medium, and low potency steroids are given. Typically, an intranasal formulation of peptide YY in combination with a high potency steroid composition includes, but is not limited to, betamethasone (0.6 to 0.75 mg dosage), or dexamethasone (0.75 mg dosage). In an alternative formulation, an intranasal formulation of peptide YY in combination with a medium potency steroid composition includes, but is not limited to, methylprednisolone (4 mg dosage), triamcinolone (4 mg dosage), or prednisolone (5 mg dosage). In a further alternative formulation, an intranasal formulation of peptide YY in combination with a low potency steroid composition includes, but is not limited to hydrocortisone (20 mg dosage) or cortisone (25 mg dosage).

EXAMPLE 4

Preparation of a PYY Formulation Free of a Stabilizer that is a Protein

A PYY formulation suitable for intranasal administration of PYY, which was substantially free of a stabilizer that is a protein was prepared having the formulation listed below.

1. About ¾ of the water was added to a beaker and stirred with a stir bar on a stir plate and the sodium citrate was added until it was completely dissolved.
2. The EDTA was then added and stirred until it was completely dissolved.
3. The citric acid was then added and stirred until it was completely dissolved.
4. The methyl-β-cyclodextrin was added and stirred until it was completely dissolved.
5. The DDPC was then added and stirred until it was completely dissolved.
6. The lactose was then added and stirred until it was completely dissolved.
7. The sorbitol was then added and stirred until it was completely dissolved.
8. The chlorobutanol was then added and stirred until it was completely dissolved.
9. The PYY 3–36 was added and stirred gently until it dissolved.
10. 11 Check the pH to make sure it is 5.0±0.25. Add dilute HCl or dilute NaOH to adjust the pH.
11. Add water to final volume.

TABLE 6

| Reagent | Grade | Vendor | mg/mL | % |
|---|---|---|---|---|
| Chlorobutanol, anhydrous | NF | Spectrum | 5.0 | 0.50 |
| Methyl-β-Cyclodextrin | | Sigma | 45 | 4.5 |
| L-α-Phosphatidylcholine Didecanoyl | | Sigma | 1 | 0.1 |
| Edetate Disodium | USP | Dow Chemicals | 1 | 0.1 |
| Sodium Citrate, Dihydrate | USP | Spectrum | 1.62 | 0.162 |
| Citric Acid, Anhydrous | USP | Sigma | 0.86 | 0.086 |
| α-Lactose monohydrate | | Sigma | 9 | 0.9 |
| Sorbitol | | Sigma | 18.2 | 1.82 |
| PYY 3-36 | GMP | Bachem | 1 | 0.1 |
| Purified Water | | | | |

Formulation pH 5 +/− 0.25
Osmolarity ~250

EXAMPLE 5

A second formulation was prepared as above, except the concentration of PYY 3–36 was 15 mg/mL as shown below in Table 7.

TABLE 7

| Reagent | Grade | Vendor | mg/ml | % |
|---|---|---|---|---|
| Chlorobutanol, anhydrous | NF | Spectrum | 5.0 | 0.50 |
| Methyl-β-Cyclodextrin | | Sigma | 45 | 4.5 |
| L-α-Phosphatidylcholine Didecanoyl | | Sigma | 1 | 0.1 |
| Edetate Disodium | USP | Dow Chemicals | 1 | 0.1 |
| Sodium Citrate, Dihydrate | USP | Spectrum | 1.62 | 0.162 |
| Citric Acid, Anhydrous | USP | Sigma | 0.86 | 0.086 |
| α-Lactose monohydrate | | Sigma | 9 | 0.9 |
| Sorbitol | | Sigma | 18.2 | 1.82 |
| PYY 3-36 | GMP | Bachem | 15 | 0.1 |
| Purified Water | | | | |

Formulation pH 5 +/− 0.25

EXAMPLE 6

Determination of Optimal pH of PYY

Determination of $PYY_{3-36}$ stability vs. pH at 40° C. for 5 days

A. Protocol for formulating PYY (3–36)/pH stability study samples
Osmolarity: Target 250 mM
Using a Citrate/Sodium citrate, tri-basic buffer, 10 mM $$\text{Osmolarity} = \text{no. particles} \times \text{molarity}$$
$$= (1 + 4) \times 10 \text{ mM} = 50 \text{ mM}$$

Therefore bring osmolarity to 250 mM with 100 mM NaCl (2 particles)

B. Made up Stability Samples as Follows (3500 μl)

Final Concentration
Citrate buffer 1400 μL 25 mM (of required final pH) 10 mM
PYY 700 μl 1.5mg/mL 300 ug/ml
Chlorobutanol 350 μl 2.5%, 0.25%
NaCl, 350 μl 1.0M, 100 mM
Check pH and adjust if required
Q.S. to 3500 μL with water Procedure:
120 μl sample in 200 ul silanized inserts in autosampler vials
3 pulls/time point
Samples incubated at 40° C. for 5 days C. Comparison of Target and Actual Final pH of Stability Mixtures

| Target pH | Actual pH |
|---|---|
| 3.0 | 2.99 |
| 3.5 | 3.47 |
| 4.0 | 3.90 |
| 4.5 | 4.42 |
| 5.0 | 4.90 |
| 7.0 | 7.38 |

D. HPLC Procedure
Column: Waters C18 Bondapak 10 μm 4.6×300 mm
HPLC system: Waters Alliance 2690
Detector: Waters 2487 Dual wavelength at 220 nm
Flow rate: 1 ml/mim
Injection volume: 30 μL
Column temp. 30° C.

Mobile Phases:
Buffer A: 0.1% TFA, 1% acetonitrile in water
Buffer B: 0.11% TFA in acetonitrile

| | Gradient: | |
|---|---|---|
| Time (mins) | % A | % B |
| 0 | 75 | 25 |
| 17 | 42 | 58 |
| 19 | 75 | 25 |
| 28 | 75 | 25 |

E. Results and Conclusions:

Results indicate that under the particular conditions used in this study, that the optimal pH for stability is 4.90. There is an increase in stability from 76 to 87% with increasing pH from 2.99 to 4.90. the preferred pH is thus between about 2.0 and about 8.0 and most preferably between 3.0 and 7.5.

At higher pH, i.e. 7.38 there is a large drop in the stability of PYY(3–36) with only 15% of time zero remaining.

EXAMPLE 7

Intranasal Formulation Development

Peptides and proteins are relatively fragile molecules compared to low-molecular-weight therapeutics. The objective of the formulation development phase was to identify a candidate formulation suitable for intranasal delivery. In order to achieve this goal, numerous candidates were tested in order to identify a formulation with acceptable drug stability, delivery across the nasal mucosa, toxicity and preservative effectiveness.

Initially, the effect of pH was examined. FIG. 1 shows the stability of $PYY_{3-36}$ at high temperature (40° C.) at various pHs from 3.0 to 7.4. At physiological pH, there was substantial loss of drug at elevated temperature. Best stability was achieved at about pH 5.0. This pH was chosen for further formulation optimization.

To further optimize stability, various stabilizing agents were tested for their ability to facilitate passage of drug across the nasal mucosa. The enhancers tested were chosen based on their ability to open tight junctions with limited cellular toxicity. To accomplish this, a primary human epithelial cell model (EpiAirway, MatTek, Inc., Ashland Mass.) was employed. This cell line forms a pseudo-stratified columnar epithelial cell layer with tight junctions similar to the respiratory epithelium found in the nose. Drug formulations were placed on the apical side of the tissue layer, and drug quantitation carried out for the basal media. The extent of tight junction opening was measured by decrease in the transepithelial electrical resistance (TEER). Cell viability and cytotoxicity were monitored by MTT and LDH assays, respectively. Data from a representative screening experiment are depicted in FIGS. 2–5.

Figure 2:
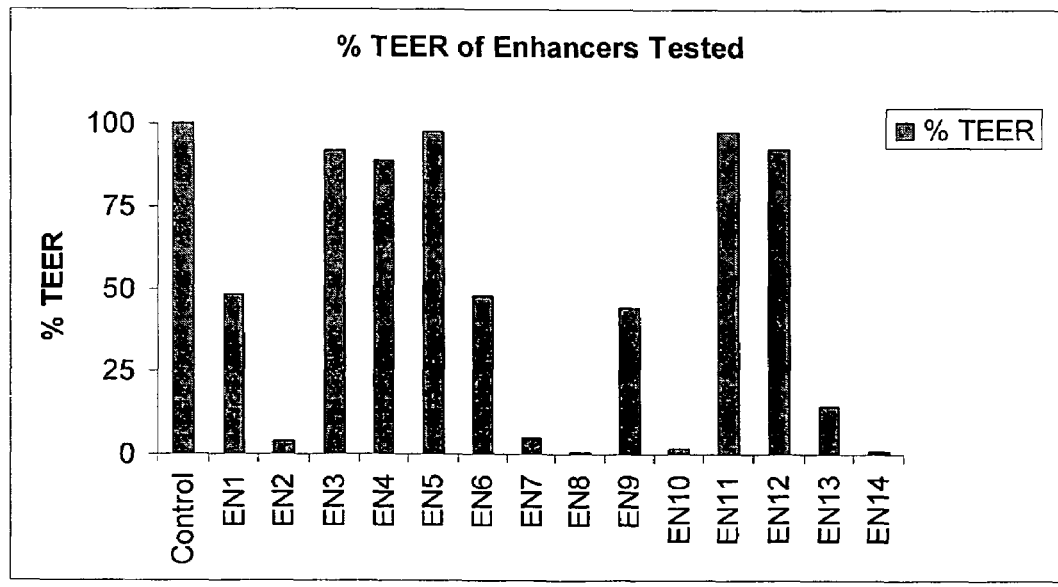
FIG. 2 shows the data for TEER of permeability enhancers.

FIG. 2 shows the data for TEER. In some cases there was little or no decrease in TEER compared to the control, indicating tight junctions which remain closed. In other cases there was a substantial drop in TEER indicating tight junction opening. The results demonstrate that the in vitro cell model is capable of discriminating the ability of different formulations to open the tight junctions.

Figure 3:
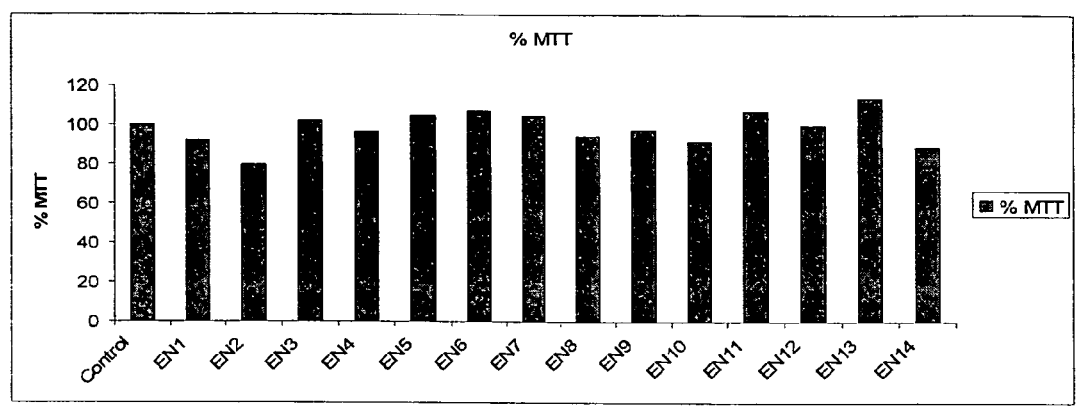
FIG. 3 shows the cell viabilities of candidate PYY formulations.
Figure 4:
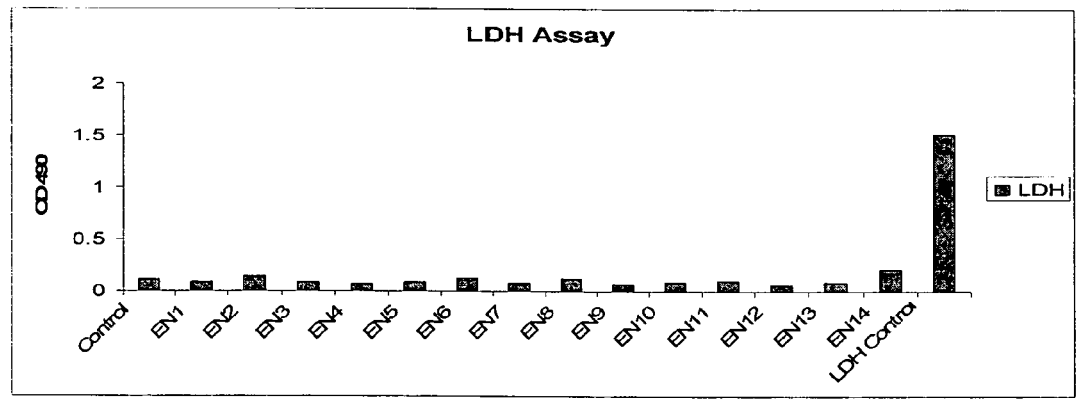
FIG. 4 shows the cytotoxic effects of candidate formulations.
Figure 5:
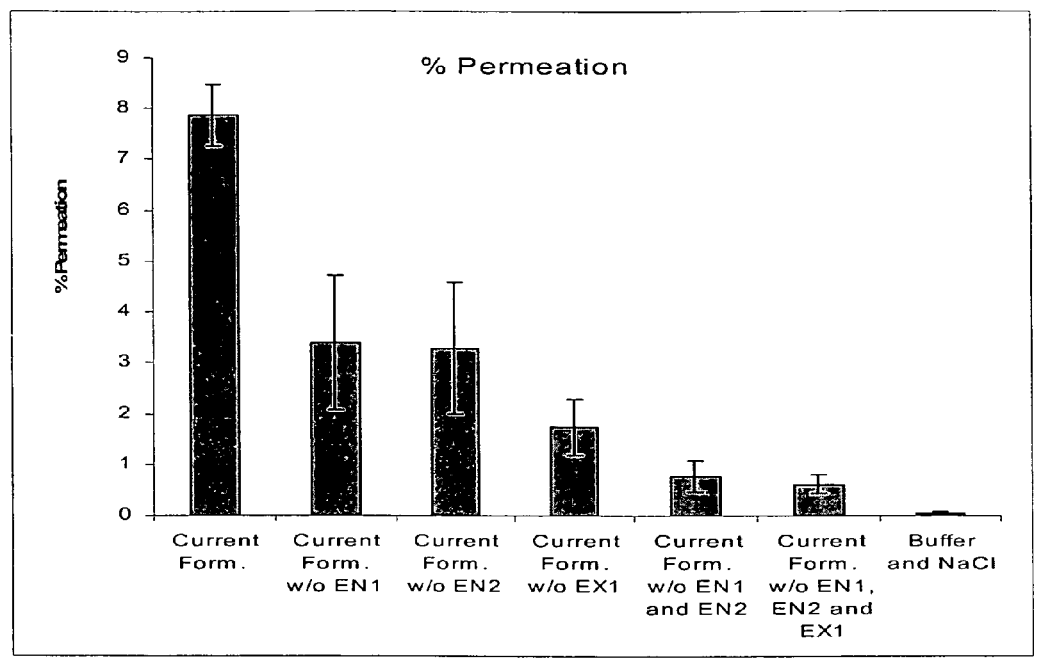
FIG. 5 shows the synergistic contributions of the various components on drug permeation.

In the candidate formulations tested the cell viabilities (FIG. 3; MTT) were good and cyctotoxicities (FIG. 4; LDH) were low.

In total, over 200 different formulations were tested, reflecting the high-throughput nature of the in vitro screening model. Using all the available data, a multivariate analysis was conducted to elucidate the effect each formulation component exerted on each of the 7 output variables (drug permeability, osmolality, stability at refrigerated and accelerated conditions, TEER, and MTT and LDH assays). The multivariate analysis consisted of an initial analysis of each formulation component for some level of correlation with output parameters (p<0.1). With the subset identified, either a linear regression or stepwise logistic selection model was used. The results suggest that one excipient correlated to osmolality and toxicity ($r^2$=0.91 and 0.27, respectively), two correlated to $PYY_{3-36}$ permeation ($r^2$=0.44), three affected stability ($r^2$=0.24), and five impacted paracellular resistance ($r^2$=0.55). The best formulations determined by this process increased at least 30–75 fold the $PYY_{3-36}$ transport compared to simple buffer solutions.

Based on these analyses, an optimized $PYY_{3-36}$ formulation was selected for further development. This optimized formulation contained two stabilizers, two permeation enhancers, one chelating agent, and one preservative in a sodium acetate buffer, pH 5.0. This formulation passed the USP Preservative Effectiveness Test. The synergistic contributions of the various components on drug permeation is presented in FIG. 5. Compared to simple buffer formulations at the same osmolality, the optimized formulation exhibits more than 100-fold increased drug permeation.

Finally, pre-clinical and clinical batches of the optimized formulation were prepared and placed on stability at 5° C. and 25° C. in the final product packaging. Preliminary data, depicted in Table 8 reveal that storage for up to two months at either 5° C. or 25° C. results in 90% or better peptide retention.

TABLE 8

| Time point | 5° C. % PYY | 25° C. % PYY |
|---|---|---|
| 0 | 100.0 | 100.0 |
| 3 days | 99.8 | 100.1 |
| 7 days | 102.6 | 98.4 |
| 10 days | 103.3 | 101.7 |
| 2 weeks | 101.4 | 97.9 |
| 3 weeks | 100.3 | 95.4 |
| 1 month | 100.5 | 96.3 |
| 1.5 months | 100.1 | 90.6 |
| 2 months | 99.8 | 92.3 |

In summary, our process of formulation development has produced a $PYY_{3-36}$ formulation with suitable drug stability, delivery across the nasal mucosa, toxicity and preservative effectiveness, which enables delivery of a 4 kD peptide.

Preclinical Studies

To date, a series of six preclinical studies in rats, rabbits, and dogs have been completed. Plasma $PYY_{3-36}$ levels in all species were determined by a validated proprietary radioimmunoassay method.

Bioavailability (the molar fraction of drug identified in plasma divided by the amount administered nasally) in rats was determined to be approximately 6%, and in rabbits is approximately 8%. These values may understate the true bioavailability, as any peptide degradation in plasma before sampling, or degradation after sampling despite the presence of a proteinase inhibitor, will decrease the measured bioavailability.

Nasal toxicity has been evaluated in rat and rabbit models for up to 14 consecutive days at doses 50× the expected human clinical dose on a mg/kg basis. There were no microscopic or gross pathological findings related to the test article. There were no clinical observations.

Systemic toxicity following intravenous administration was evaluated in rat and rabbit models. At IV doses up to approx 160× the expected human dose (400 μg/kg in the rat and 205 μg/kg in the rabbit) there were no test article related microscopic or macroscopic findings.

Cardiovascular toxicity was assessed in the anesthetized dog model in a dose ranging study design. The highest dosage, an infusion of $PYY_{3-36}$ up to 24 ug/kg over 60 minutes corresponded to 33× the expected human dose on a body surface area basis. The resultant plasma levels, 30 ng/mL, was approximately 380× the basal canine plasma level. At this plasma level, there was no effect on arterial blood pressure, femoral blood flow, or QTc and only minor changes in heart rate [increase from 123 to 148 beats per minute (bpm) mean] and respiratory rate (decrease from 54 to 36) were noted.

Figure 6:
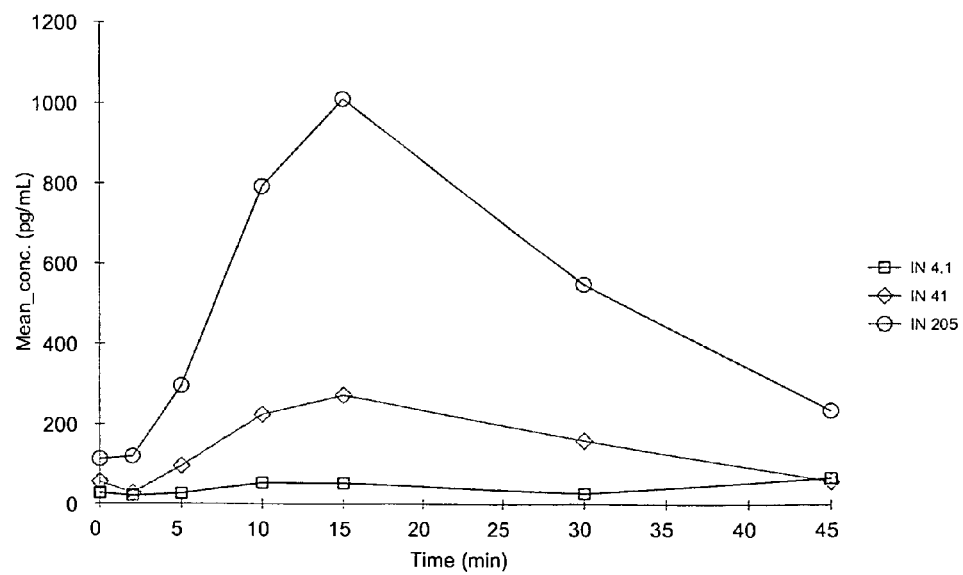
FIG. 6 shows the PYY3–36 in the plasma of rats, the square represents a dose of 4.1 µg/kg, the triangle represents a dose of 41 µg/kg, and the circle represents a dose of 205 µg/kg.
Figure 7:
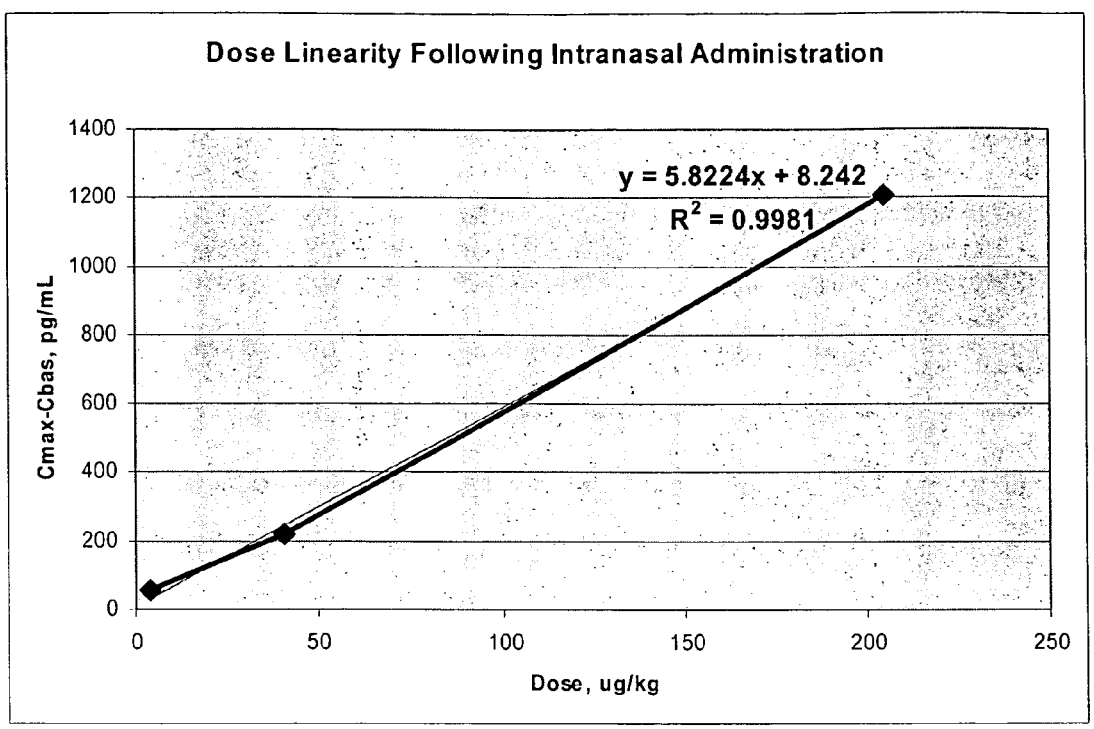
FIG. 7 shows dose linearity following intranasal administration PYY3–36 in rats as Cmax-Cbas pg/mL v. dose as µg/kg.
Figure 8:
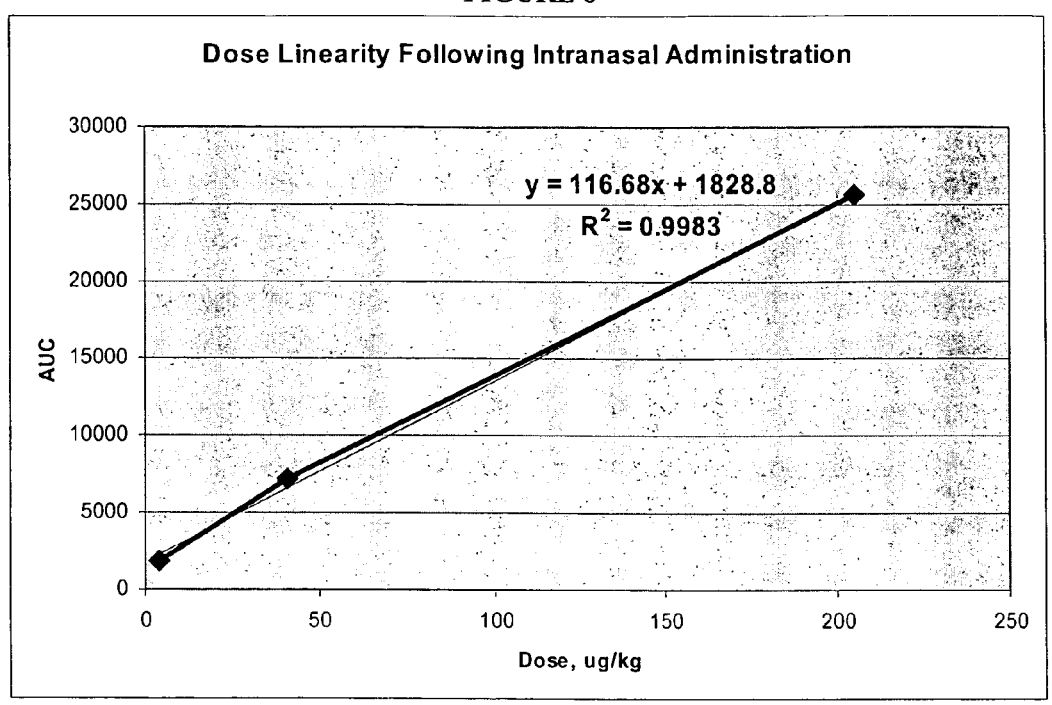
FIG. 8 shows dose linearity following intranasal administration of PYY3–36 in rats as AUC v. dose as µg/kg.
Figure 9:
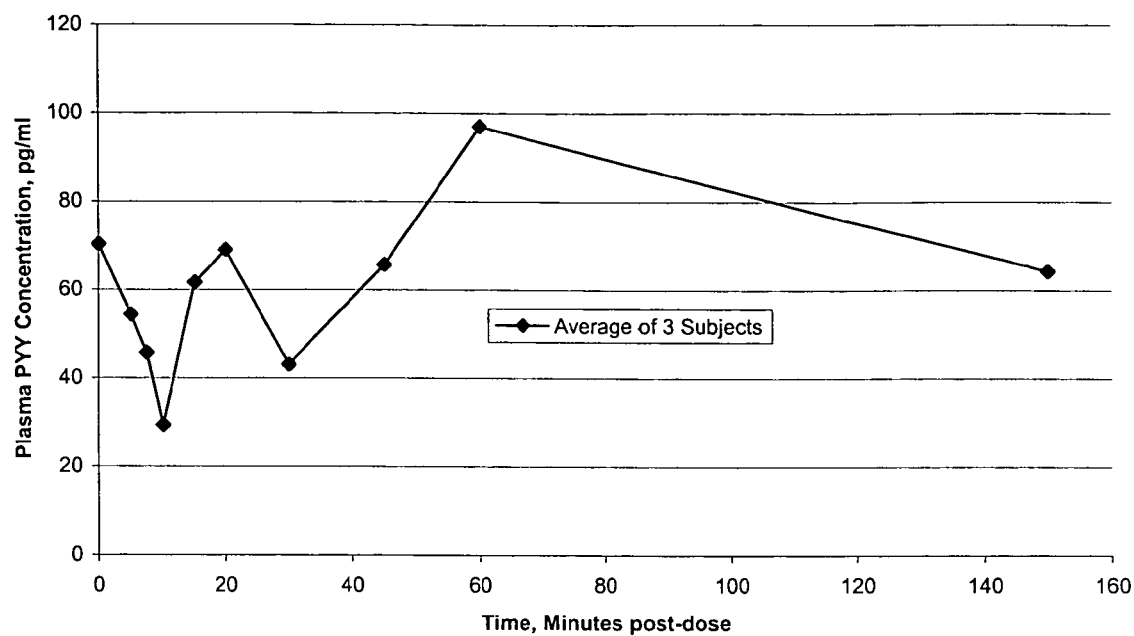
FIG. 9 shows the average plasma concentration of PYY v. time in minutes in three human volunteers who were each administered 20 µg of PYY(3–36) intranasally.
Figure 10:
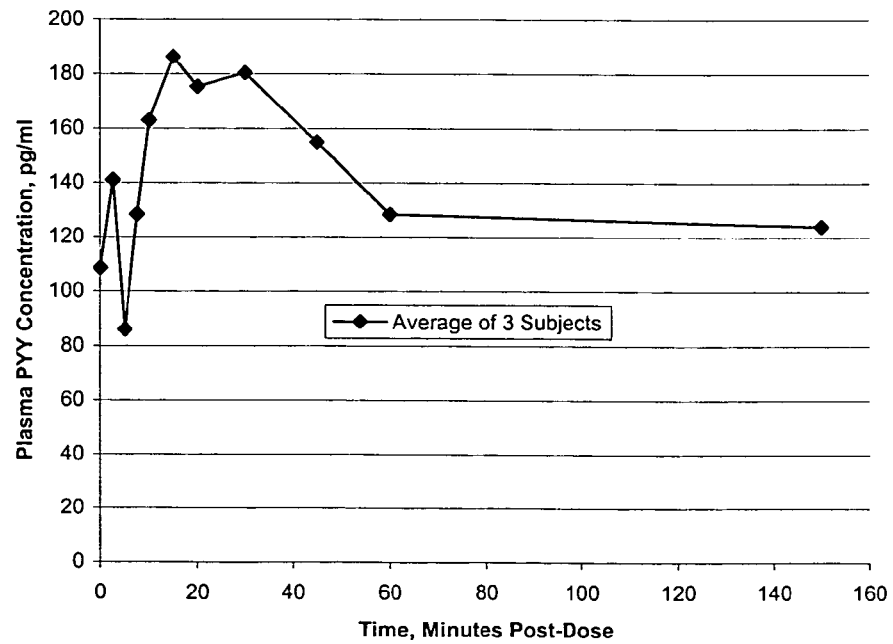
FIG. 10 shows the average plasma concentration of PYY v. time in minutes in three human volunteers who were each administered 50 µg of PYY(3–36) intranasally.
Figure 11:
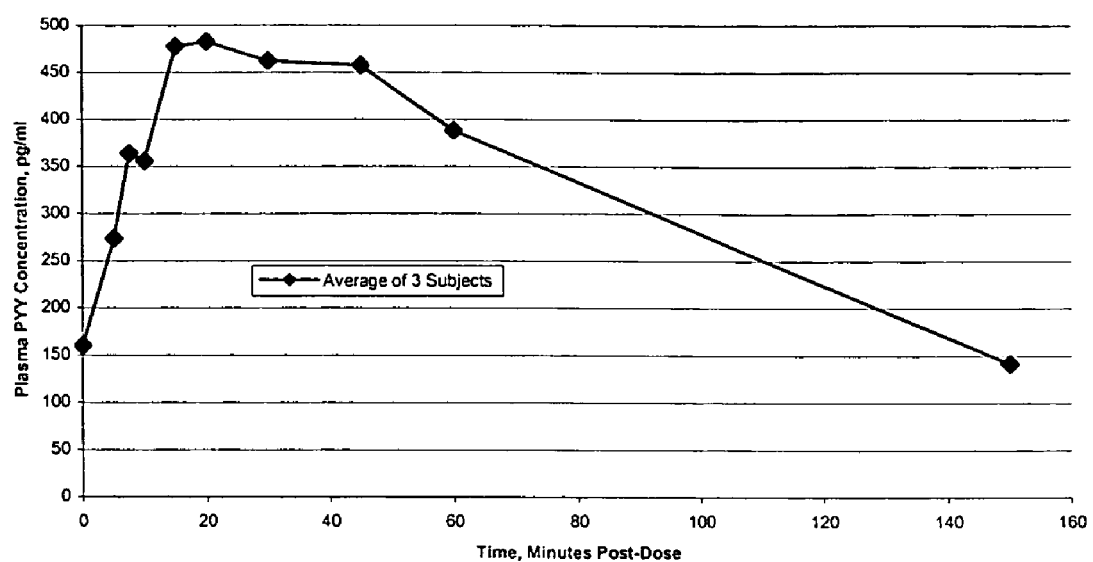
FIG. 11 shows the average plasma concentration of PYY v. time in minutes in three human volunteers who were each administered 100 µg of PYY(3–36) intranasally.
Figure 12:
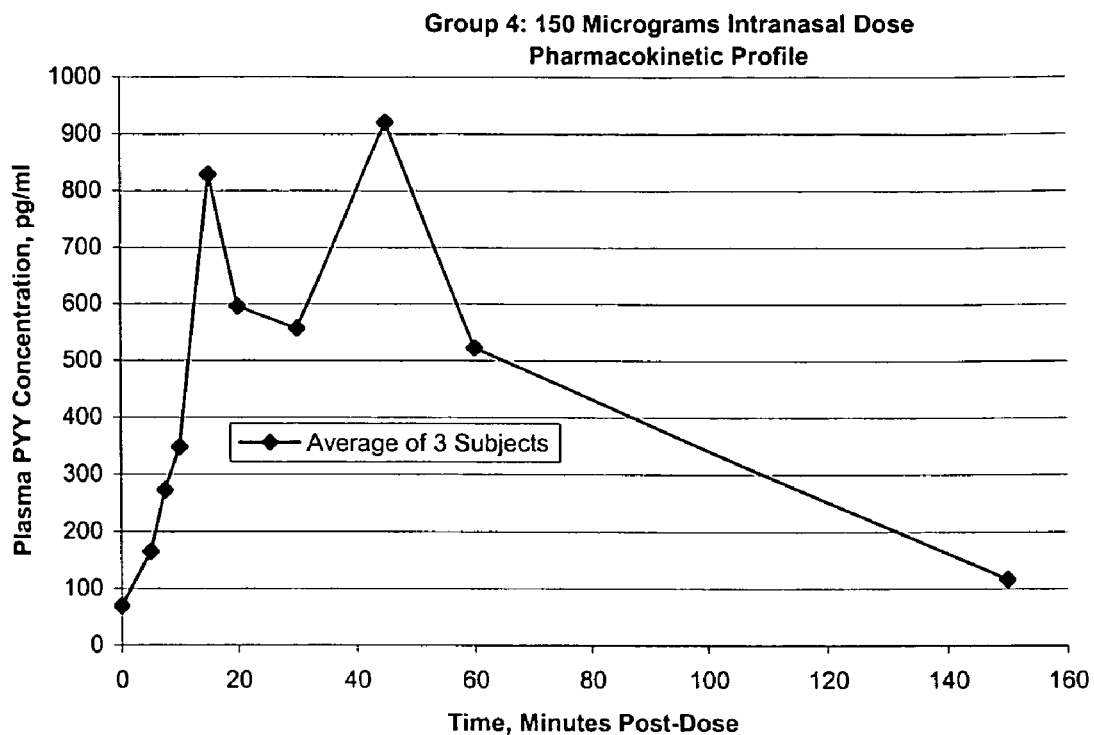
FIG. 12 shows the average plasma concentration of PYY v. time in minutes in three human volunteers who were each administered 150 µg of PYY3–36 intranasally.
Figure 13:
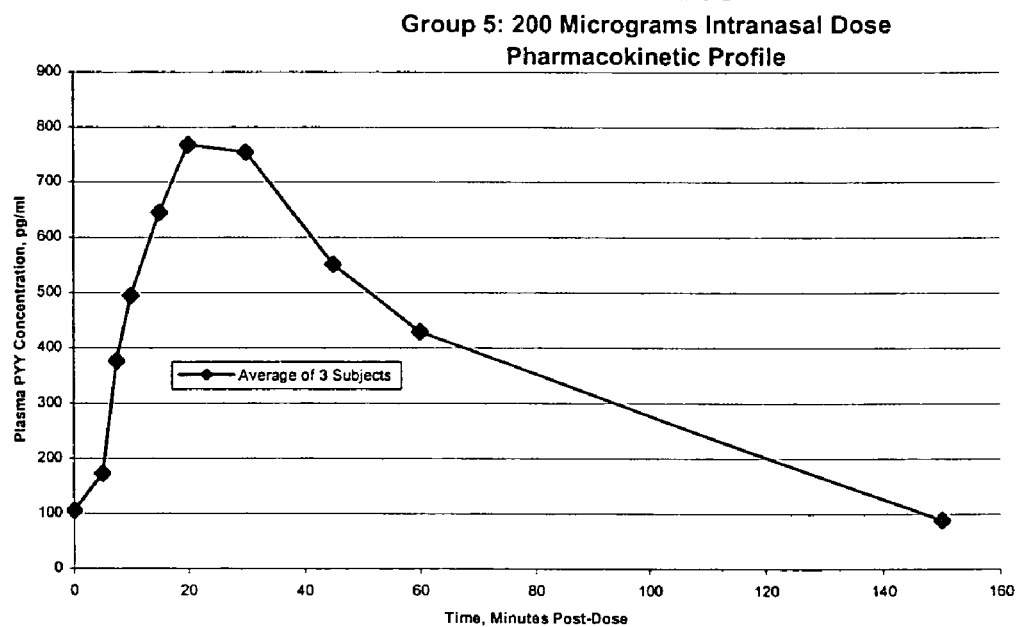
FIG. 13 shows the average plasma concentration of PYY v. time in minutes in three human volunteers who were each administered 200 µg of PYY(3–36) intranasally.
Figure 14:
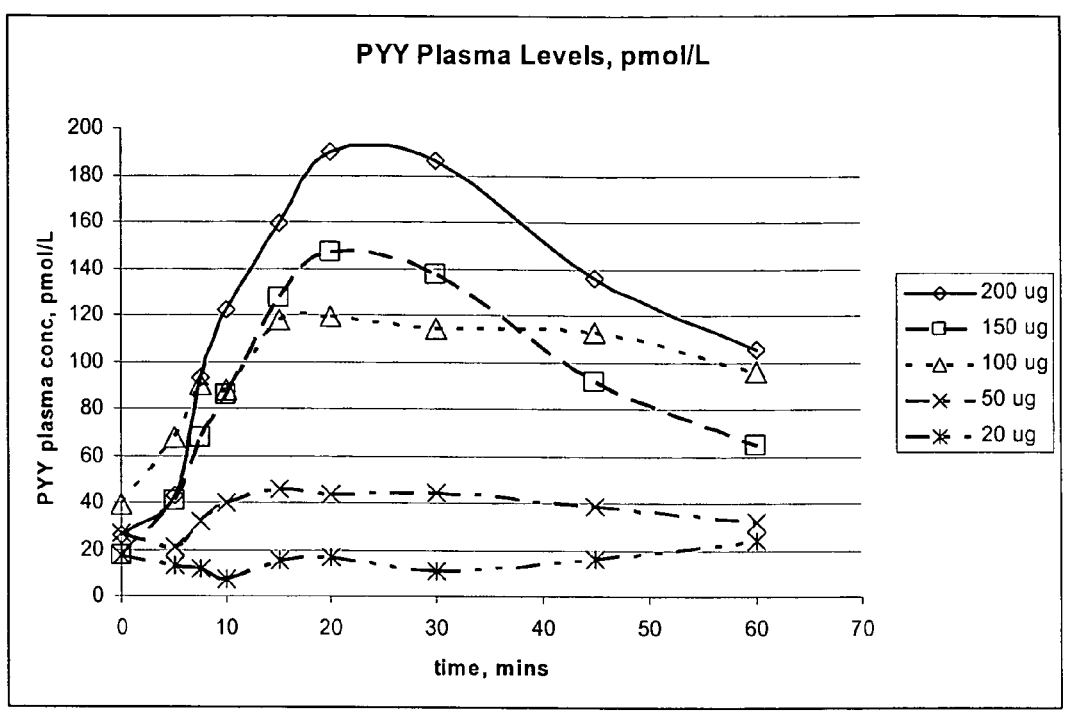
FIG. 14 shows PYY plasma concentration as pmol/L v. time for five groups of healthy human volunteers who received intranasal PYY(3–36). The doses were 200 µg, 150 µg, 100 µg, 50 µg and 20 µg of PYY3–36.
Figure 15:
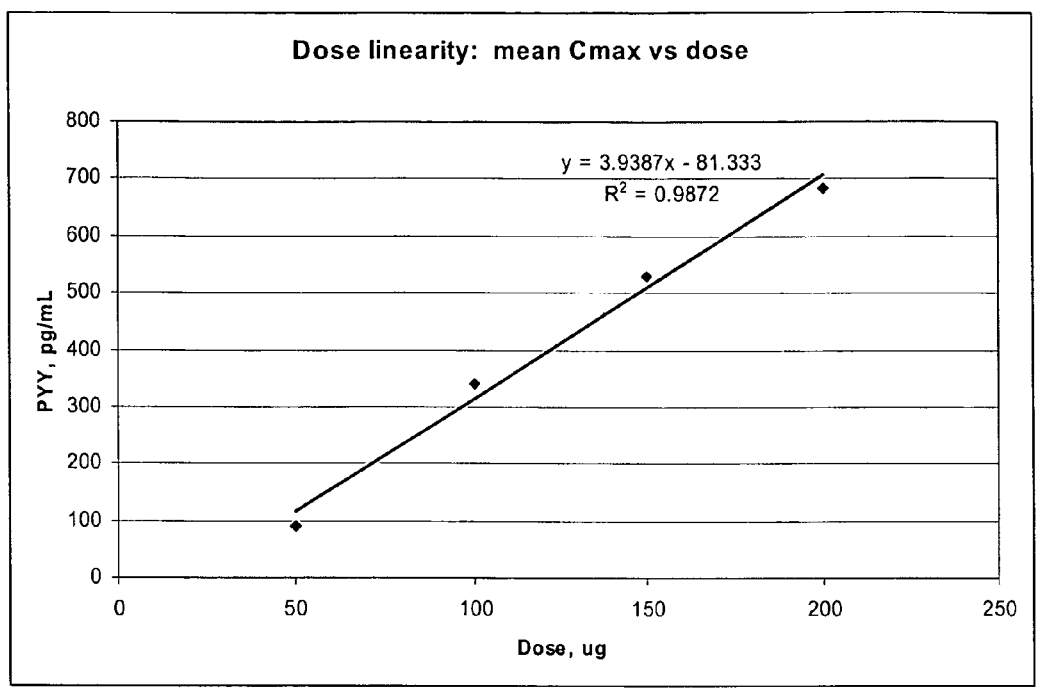
FIG. 15 shows the dose linearity Cmax of PYY in pg/mL vs. dose of PYY(3–36) administered to human volunteers.
Figure 16:
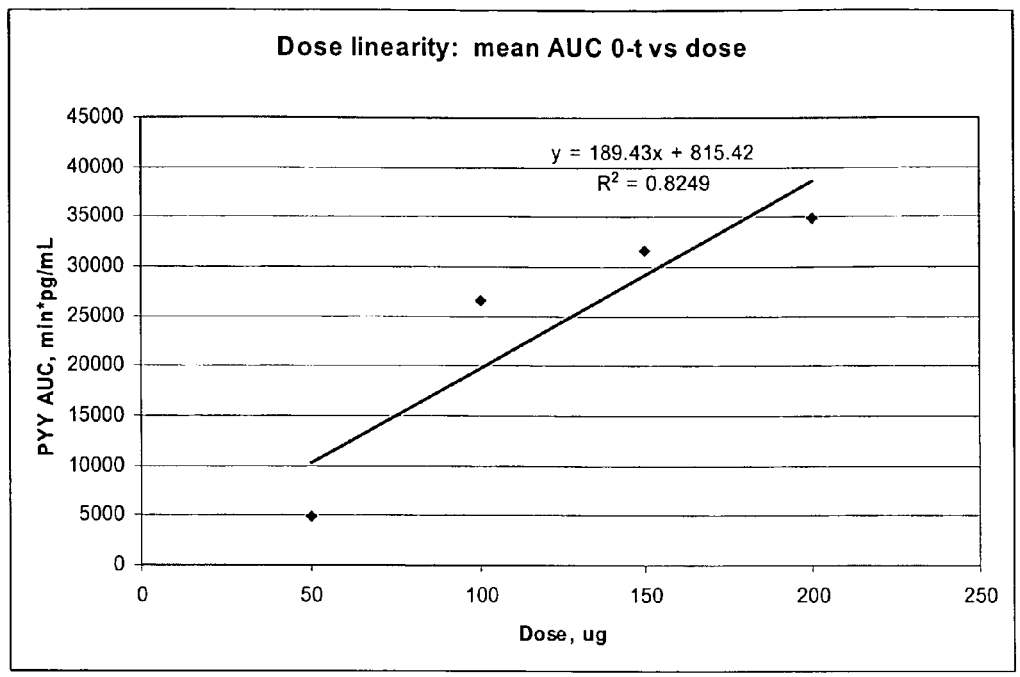
FIG. 16 shows the dose linearity PYY mean AUC in pg/mL vs. dose of PYY(3–36) administered to human volunteers.
Figure 17:
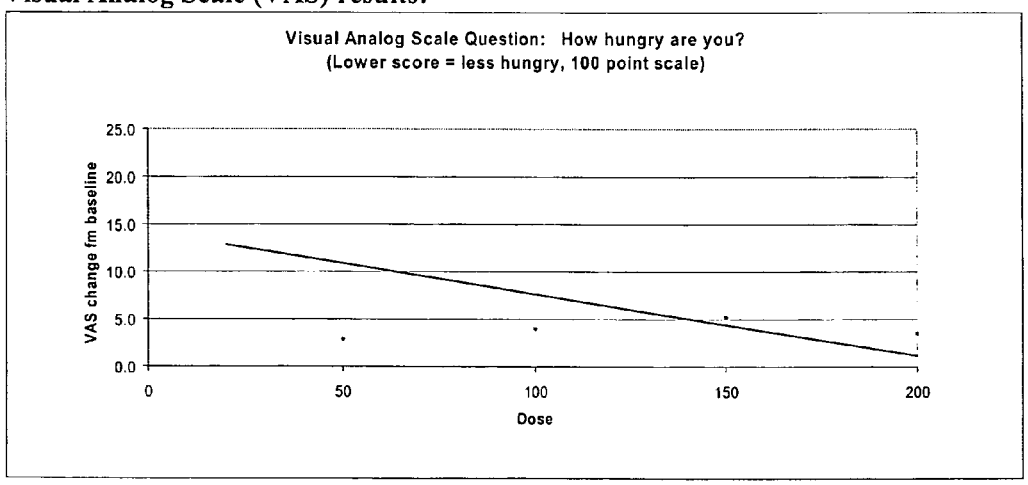
FIG. 17 shows the visual analog scale (VAS) vs. dose of PYY(3–36) administered to the human volunteers. The question was: "How hungry are you?" The lower the score the less hungry an individual was on a 100 point scale.
Figure 18:
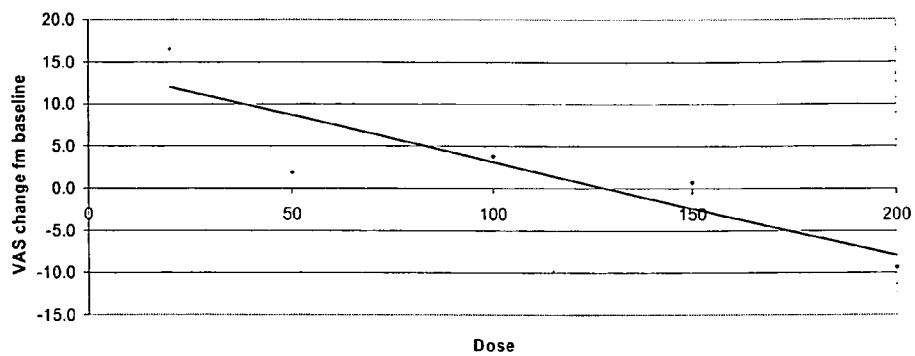
FIG. 18 shows the visual analog scale (VAS) vs. dose of PYY(3–36) administered to the human volunteers. The question was: "How much could you eat?" The lower the score the less hungry an individual was on a 100 point scale.
Figure 19:
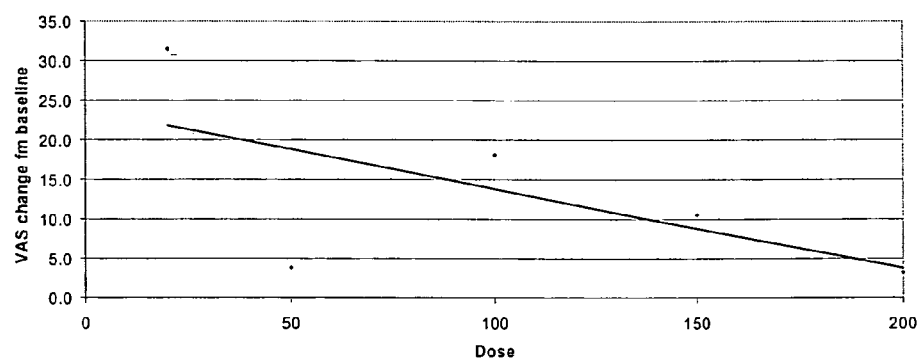
FIG. 19 shows the visual analog scale (VAS) vs. dose of PYY(3–36) administered to the human volunteers. The question was: "How full do you feel?" The lower the score the less full an individual was on a 100 point scale.
Figure 20:
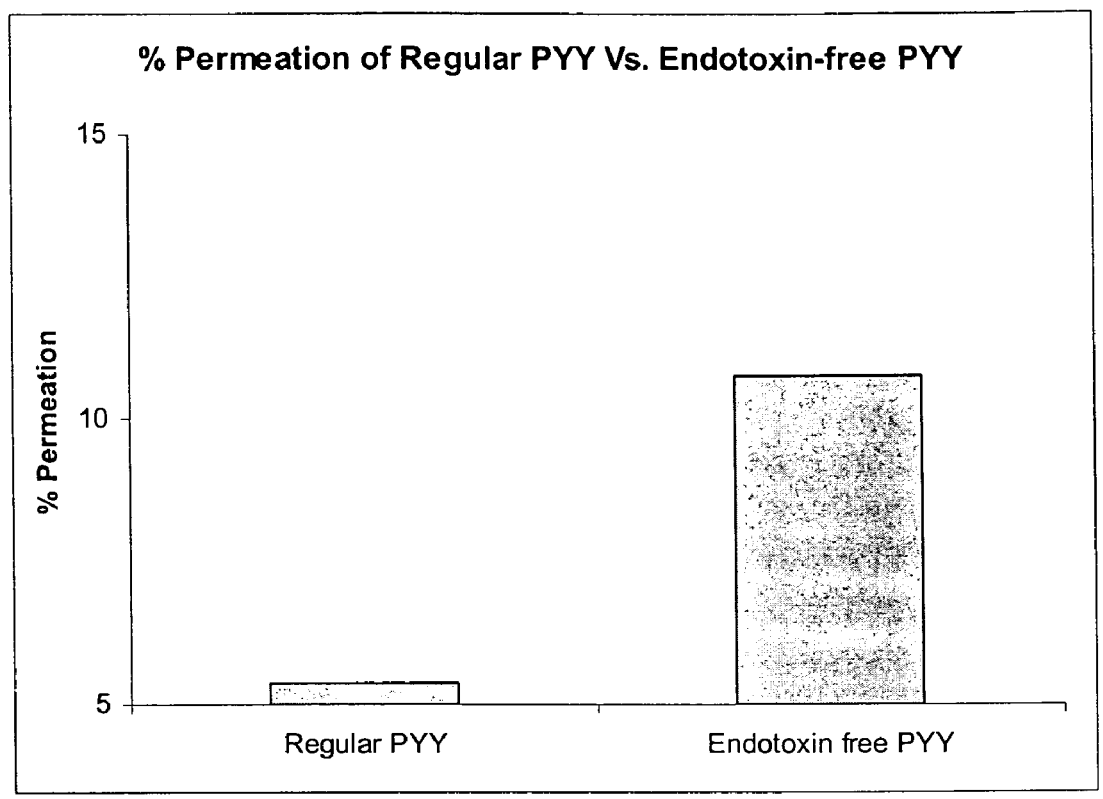
FIG. 20 shows the per cent permeation of PYY(3–36) containing endotoxin vs. endotoxin-free PYY(3–36).

Pharmacokinetic data was collected in these preclinical studies. From one study in rats, the plasma levels following intranasal administration at various doses are shown in FIGS. 6, 7and 8. FIG. 6 shows $PYY_{3-36}$ is seen in the plasma within 5 minutes, peak plasma concentrations (Tmax) are reached in 10–15 minutes, and the terminal elimination half life is approx 15 minutes. Both $C_{max}$ and $AUC_{0-t}$ are linear with respect to intranasal dose.

Clinical Studies

A dose ranging clinical trial has been initiated with the goal of establishing safety, PK, and bioavailability of the intranasal formulation of $PYY_{3-36}$. To date, patients have been enrolled in the first two of five dose cohorts. One patient reported a taste in the back of his throat; there have been no other adverse events to date.

Conclusion

Formulation, preclinical, and initial clinical work have begun on an intranasal formulation of $PYY_{3-36}$. The approach to formulation has resulted in a more than one hundred fold increase in transmembrane permeability of this 4 kD peptide with no increase in cellular toxicity. Preclinical studies have demonstrated a considerable safety margin for nasal, cardiovascular, and systemic toxicity for $PYY_{3-36}$. On the basis on the ongoing dose ranging clinical studies, chronic administration weight loss studies are planned.

EXAMPLE 8A

Clinical Protocol

Nasal Absorption of Intranasal Peptide $YY_{3-36}$ ($PYY_{3-36}$) in Healthy Human Subjects Object of the Present Study:

The object of the present study was to evaluate the absorption of intranasally administered PYY3–36 into the blood stream from the nose. This was a phase I, in clinic, single dose, doses escalation study involving fasted, normal, healthy male and female volunteers. Ascending doses of intranasal PYY3–36 were evaluated between 20 μg to 200 μg to evaluate safety, nasal tolerance and absorption of PYY3–36. Assessment of appetite sensation in each individual was also evaluated.

$PYY_{3-36}$ was administered to 15 healthy humans divided into 5 Groups of 3 individuals each.

Group I.

The first group was administered by an intranasal spray 20 μg of $PYY_{3-36}$ in a 0.1 ml solution.

Group II

The second group received intranasally 50 μg of $PYY_{3-36}$ in a 0.1 ml solution.

Group III

The third group received intranasally 100 μg of $PYY_{3-36}$ in a 0.1 ml solution.

Group IV

The fourth group received intranasally 150 μg of $PYY_{3-36}$ in a 0.1 ml solution.

Group V

The fifth group received intranasally 200 μg of $PYY_{3-36}$ in a 0.1 ml solution.

Blood samples were taken collected and the plasma concentrations of PYY were determined at 0 (i.e., pre-dose), 5, 7.5, 10, 15, 20, 30, 45, 60 minutes post-dose. The subjects were then fed and a blood sample taken and the concentration of PYY was determined 30 minutes postprandial. Plasma concentrations of $PYY_{3-36}$ were determined using a validated analytical procedure.

For each subject, the following PK parameters were calculated, whenever possible, based on the plasma concentrations of $PYY_{3-36}$, according to the model independent approach:

$C_{max}$ Maximum observed concentration.

$t_{max}$ Time to maximum concentration.

AUC$_{0-t}$ Area under the concentration-time curve from time 0 to the time of last measurable concentration, calculated by the linear trapezoidal rule.

The following parameters were calculated when the data permits accurate estimation of these parameters:

AUC$_{0-\infty}$ Area under the concentration-time curve extrapolated to infinity, calculated using the formula:

$$AUC_{0-\infty} = AUC_{0-t} + \frac{C_t}{K_e}$$

where $C_t$ is the last measurable concentration and $K_e$ is the apparent terminal phase rate constant.

$K_e$ Apparent terminal phase rate constant, where $K_e$ is the magnitude of the slope of the linear regression of the log concentration versus time profile during the terminal phase.

$t_{1/2}$ Apparent terminal phase half-life (whenever possible), where $t_{1/2}=(\ln 2)/K_e$.

PK calculations were performed using commercial software such as WinNonlin (Pharsight Corporation, Version 3.3, or higher). The results are shown in the graphs below.

DISCUSSION AND CONCLUSION

Background:

Each dosing group included three subjects who were dosed intranasally once with a formulation of this invention that contained a specified dose of synthetic, pyrogen-free human PYY$_{3-36}$. Five dosing groups were organized, with escalating doses of PYY$_{3-36}$ in the formulation. Blood samples were drawn at specified intervals into blood collection tubes that contained lithium heparin (to inhibit coagulation) and aprotinin (to preserve PYY$_{3-36}$). Plasma from each blood sample was collected by centrifugation and stored in frozen aliquots. One frozen aliquot of each blood sample was shipped to Nastech Analytical Services and arrived frozen. Each sample was stored frozen until assayed for PYY concentration by radioimmunoassay (RIA).

Observations:

Group 1: This group of subjects was dosed with 20 micrograms of PYY$_{3-36}$. Plasma PYY concentrations for the subjects varied from a minimum of "less than 20 pg/ml" (below the lower limit of quantitation of the radioimmunoassay) to a maximum of 159 pg/ml. The trends of concentrations observed are not consistent with significant absorption of drug into the blood of the subjects studied.

Group 2: This group of subjects was dosed with 50 micrograms of PYY$_{3-36}$. Plasma PYY concentrations for the subjects varied from a minimum of 50 pg/ml to a maximum of 255 pg/ml. The trends of concentrations observed are consistent with significant absorption of drug into the blood of the subjects studied.

Group 3: This group of subjects was dosed with 100 micrograms of PYY$_{3-36}$. Plasma PYY concentrations for the subjects varied from a minimum of 87 pg/ml to a maximum of 785 pg/ml. The trends of concentrations observed are consistent with significant absorption of drug into the blood of the subjects studied.

Group 4: This group of subjects was dosed with 150 micrograms of PYY$_{3-36}$. Plasma PYY concentrations for the subjects varied from a minimum of 45 pg/ml to a maximum of 2022 pg/ml. The trends of concentrations observed are consistent with significant absorption of drug into the blood of the subjects studied.

Group 5: This group of subjects was dosed with 200 micrograms of PYY$_{3-36}$. Plasma PYY concentrations for the subjects varied from a minimum of 48 pg/ml to a maximum of 1279 pg/ml. The trends of concentrations observed are consistent with significant absorption of drug into the blood of the subjects studied.

These results are consistent with a dose dependent absorption of PYY$_{3-36}$.

Additional Observations and Data:

Summary of Findings:

At intranasal doses of 50 μg-200 μg, there is dose dependent plasma uptake of PYY.

The duration of elevated plasma concentrations is considerably longer than would have been predicted, with an elimination half-life calculated at 55 minutes.

Cmax and AUC 0-t show good linearity with dose.

There is considerable inter-subject variability at a given dose.

Surprisingly, this study failed to detect postprandial elevation of PYY although the quantity of food actually eaten was not measured and if too little was eaten could explain the observations.

Visual-analog scale hunger questions suggest decreased hunger with increasing doses of PYY.

Nausea and lightheadedness appear to be related to very high plasma concentration of PYY.

Notes:

In some cases pMol/L are used as the PYY measurement units; in other analyses, pg/mL are used. The conversion factor is pmol/L*4.05=pg/mL.

In some cases, the 150-minute time point is displayed in plots. Strictly speaking, this is a postprandial datapoint, and may therefore confound PK evaluation. However, an unexpected finding described in more detail below is that the 30-minute postprandial time point is no different from the baseline value.

PYY Plasma Concentrations:

The PYY assay described in this specification has been validated for its own PYY plasma concentration assay. Using this assay, samples from each time point were assayed in triplicate. Note that out of the 180 data points, 3 (1.6%) appear to be biologically implausible "outliers." The data throughout this preliminary analysis use a dataset in which these three data points were removed.

TABLE 9

Descriptive PK parameters:
Calculated PK parameters include:

| Tmax (min) | Cmax (pg/mL) | AUC 0-last (min * pg/mL) | AUC 0-inf (min * pg/mL) | $T_{1/2}$ (min) |
|---|---|---|---|---|
| 20 | 60 | 47 | 3850 | | |
| 50 | 18 | 89 | 4960 | 12379 | 112 |
| 100 | 32 | 342 | 26535 | 41102 | 27 |
| 150 | 23 | 530 | 31659 | 39476 | 39 |
| 200 | 23 | 683 | 34823 | 48618 | 42 |

Examination of the mean PK plots suggests a dose response from 50–200 μg doses, but that the 20 μg dose is in the noise. Therefore, many of the subsequent analyses will be based on data only from the 50–200 μg doses. We also propose that, because PYY is an endogenous molecule, the AUC 0-t is more relevant than AUC 0-inf.

Tmax and T$_{1/2}$ (elimination half life):

|  | Tmax (min) | T$_{1/2}$ (min) |
|---|---|---|
| Mean values for 50–200 μg dose groups: | 24 | 55 |

The Tmax of 24 minutes is typical for a nasal product. The elimination half life of 55 minutes is considerably longer than would have been expected. Literature references indicated a t$_{1/2}$ typically of 5–10 minutes. The elimination half-life may also be affected by some continued uptake from the nasal mucosa occurring after the Tmax and by formulation components that effect peptide metabolism. Alternatively, because the assay described in this specification employs an extraction procedure, the assay will capture both free and protein-bound PYY, whereas an assay that does not use an extraction may assay primarily the free fraction.

From this analysis of mean VAS change from baseline (mean of 10, 30, and 60 minute values minus baseline) vs. dose, one observes:

For VAS Q1 "How hungry do you feel?" subjects were less hungry after receiving higher PYY doses. For VAS Q3, "How much do you think you can eat?" subjects thought they could eat less after receiving higher doses of PYY. However, for VAS Q2 "How full do you feel?" subjects felt less full after receiving higher doses of PYY. This suggests that the sensation follow PYY administration does not include fullness, bloating, or gastric hypercontractility.

EXAMPLE 8B

PYY Human Administration and Weight Loss

The following PYY Nasal formulation was made.

| Reagent | Grade | Vendor | Cat # | Lot # | F.W. | mg/ml | % |
|---|---|---|---|---|---|---|---|
| Chlorobutanol, anhydrous | NF | Spectrum | CH123 | RI1646 | 177.46 | 2.5 | 0.25 |
| Methyl-β-Cyclodextrin |  | Sigma | C-4555 | 81K1179 |  | 45 | 4.5 |
| L-α-Phosphatidylcholine Didecanoyl |  | Sigma | P-7081 | 55H8377 | 565.7 | 1 | 0.1 |
| Edetate Disodium (EDTA) | USP | Dow Chemicals |  | 1034N-00269-2 | 372.2 | 1 | 0.1 |
| Sodium Citrate, Dihydrate | USP | Spectrum | S0165 | RH1056 | 294.1 | 1.6 | 0.16 |
| Citric Acid, Anhydrous | USP | Sigma | C-1857 | 062K003 | 192.13 | 0.9 | 0.09 |
| PYY(3-36), endotoxin-free |  | Phoenix | 059-02 | 420338 | 4049.71 | 2 | 0.2 |
| Purified Water |  |  |  |  |  |  |  |

Formulation pH 5 +/− 0.25

One or two sprays were administered daily to a human subject over 10 day period and a weight loss of 2.5 pounds was recorded. During periods ranging from 10 minutes to 12 hours after administration the subject recorded reduced hunger.

EXAMPLE 9

A study was conducted comparing the ability of endotoxin-free PYY(3–36) (SEQ ID NO: 2) vs. non-endotoxin-free PYY(3–36) to permeate the bronchial epithelium according of to the procedure of Example 1. It was determined that about twice the amount of endotoxin-free PYY (3–36) permeated the bronchial epithelium as compared to PYY(3–36) formulation that contained endotoxin.

Both formulations contained Chlorobutanol 2.5 mg/ml, 2. mg/ml of DDPC, 10 mg/ml of albumin, 1 mg/ml of EDTA (edetate disodium) and 45 mg/ml of M-B-CD. One formulation contained endotoxin-free PYY(3–36) and the other formulation contained 70 EUs or greater of endotoxin.

The average MTT of the PYY(3–36) formulation containing endotoxin was 91.72% while the endotoxin-free PYY(3–36) formulation had an average MTT of 100.16%.

The average permeation of the PYY(3–36) formulation containing endotoxin was 5.36%, while the average permeation of the endotoxin-free PYY(3–36) formulation was 10.75%.

A number of known mucosal delivery enhancing excipients can be effectively combined with endotoxin-free Y2 receptor binding peptides, especially endotoxin-free PYY3–36, and can be used to improve non-infusion formulations, especially oral delivery. Such excipients are contained in the following patent applications that are incorporated by reference: U.S. Patent applications 20030225300, 20030198658, 20030133953, 20030078302, 20030045579, 20030012817, 20030012817, 20030008900, 20020155993, 20020127202, 20020120009, 20020119910, 20020065255, 20020052422, 20020040061, 20020028250, 20020013497, 20020001591, 20010039258, 20010003001.

EXAMPLE 10

Total Extraction Radioimmunoassay for the Determination of the Concentration of PYY in Plasma 1.0 Introduction:

A radioimmunoassay was developed to measure the concentration of Human Peptide YY(3–36) (hPYY) in human plasma. Samples are collected with anticoagulant (EDTA) and protease inhibitor (aprotinin) and frozen. The assay is a four day process. Samples, controls, and standards are extracted in alcohol and dried on Day 1. All samples are reconstituted and mixed with a polyclonal rabbit antiserum directed against hPYY on Day 2. Iodinated hPYY is added on Day 3. Specific precipitating agents (Goat anti-Rabbit IgG and Normal Rabbit Serum) are added on Day 4. Bound tracer is separated from free tracer by centrifugation, and the bound tracer is counted in the gamma counter. Concentration is calculated by interpolation of a standard curve and assay performance is controlled with Quality Control samples.

2.0 Materials:
2.1 Peninsula PYY kit (Peninsula Laboratories, Cat. No. S-2043-0001)
2.2 Reagent Alcohol (Fisher Inc., Cat. No. A995-4) (or equivalent)
2.3 Stripped human plasma (with Lithium Heparin, fasted, pooled) Golden West Biologics Inc. (Cat. No., SD1020-H) (Analytical SOP # A-003)
2.4 Ice Baths (Fisher, Cat No. 11-676-36) (or equivalent)
2.5 Disposable 10 mL pipettes (Fisher Cat. No. 13-678-11E) (or equivalent)
2.6 Standard Synthetic Human PYY from Nastech QC (3-36) (Bachem Cat.
No. H8585)
2.7 Distilled Water (Milli-Q Millipore, Cat. No. ZMQ56VFT1) (or equivalent)
2.8 Triton X-100 (Sigma, Cat. No. T-9284) (or equivalent)
2.9 Aluminum Foil (Fisher, Cat. No. 01-213-3) (or equivalent)
2.10 Aprotinin (ICN Biomedicals Inc. Cat. No. 190779) (or equivalent)
2.11 12×75 mm tubes (Evergreen Scientific, Cat. No. 214-2023-010) (or equivalent)
2.12 12×75 mm tube caps (Evergreen Scientific, Cat. No. 300-2912-G20) (or equivalent)
2.13 1.5 mL microfuge tubes (Fisher, Cat. No. 05-402-25) (or equivalent)
2.14

3.0 Instruments:
3.1 Wallac WIZARD 1470 Automatic Gamma Counter (Perkin Elmer, Model No. 1470-002) (or equivalent)
3.2 Isotemp Basic Freezer, −70° C. (Kendro Laboratory Products, Model No. C90-3A31) (or equivalent)
3.3 CentriVap Concentrator (Labconco, Cat. No. 7810000) (or equivalent)
3.4 VX-2500 Multi-tube Vortexer (VWR, Cat. No. 58816-115) (or equivalent)
3.5 Marathon 21000R Centrifuge (Fisher, Cat. No. 04-977-21000R) (or equivalent)
3.6 Swinging bucket rotor (Fisher, Cat. No. 04-976-006) (or equivalent)
3.7 Motorized pipette-aid (Fisher, Cat. No. 13-681-15E) (or equivalent)
3.8 Eppendorf Micropipette
   3.8.1 2 μL–20 μL (Fisher, Cat. No. 21-371-6) (or equivalent)
   3.8.2 20 μL–200 μL (Fisher, Cat. No.21-371-10) (or equivalent)
   3.8.3 100 μL–1000 μL (Fisher, Cat. No. 21-371-13) (or equivalent)
3.9 Eppendorf Repeating Pipettor (Fisher, Cat. No. 21-380-9) (or equivalent)
3.10 Eppendorf Repeating Pipettor Combi-tips
   3.10.1 2.5 mL (Fisher, Cat. No.21-381-331) (or equivalent)
   3.10.2 25 mL (Fisher, Cat. No.21-381-115) (or equivalent)
3.11 Positive displacement pipette (Fisher, Cat. No. 21-169-10A) (or equivalent)

4.0 Procedure

Day 1
4.1 Thaw necessary reagents and samples for the assay. Prepare RIA buffer to 1× concentration (RIAB) if sufficient amount is not available.
4.2 Prepare standard curve samples in pooled stripped human plasma. Prepare as follows if using a starting concentration of 12.8 μg/mL.
   4.2.1 Add 990 μL RIAB to tube O.
   4.2.2 Add 990 μL pooled plasma to tube A.
   4.2.3 Add 500 μL pooled plasma to tubes B–H.
   4.2.4 Add 10 μL 12.8 μg/mL Standard to tube O. Vortex.
   4.2.5 Add 10 μL solution from tube O to tube A. Vortex.
   4.2.6 Add 500 μL solution from tube A to tube B. Vortex.
   4.2.7 Add 500 μL solution from tube B to tube C. Vortex.
   4.2.8 Repeat dilutions as in 4.2.7 through tube H. (See Diagram #1)
4.3 Dilute unknown human plasma samples to be tested if necessary. Samples should be diluted in pooled stripped human plasma.
4.4 Add 1.2 mL of cold alcohol to empty tubes for NSB, TB, all Standards, QC samples, and human plasma samples to be tested.
4.5 Add 400 μL of pooled stripped human plasma to NSB and TB tubes. Cap, Vortex.
4.6 Add 400 μL of each prepared Standard sample from 4.2.5 to 4.2.8 to respective standard curve tubes H-A (See Diagram #1). Cap, Vortex.
4.7 Add 400 μL of QC samples to respective tubes. Cap, Vortex.
4.8 Add 400 μL of each sample to be tested its respective tube. Cap, Vortex.
4.9 Incubate all samples on ice for 30–60 minutes.
4.10 Turn on the cold-trap switch on the Concentrator.
4.11 Centrifuge all tubes at 3000 rpm, 4° C. for 15 minutes.
4.12 Transfer 1.3 mL of supernatant from each sample to a new set of empty tubes. Store in an ice bath or at 2–8° C. if not spun immediately.
4.13 Place samples in the Concentrator.
4.14 Samples should spin for two hours at 40° C., then at ambient temperature for a total of 5 hours or until dry.
4.15 Remove dried samples, cover and store overnight at 2–8° C.

Day 2
4.16 Remove the dried tubes from the 2–8° C. cooler.
4.17 Add 100 μL of 4×RIA buffer concentrate to each tube.
4.18 Add 100 μL of 0.6% TX100 to each tube. (Attachment #1) Vortex for a minimum of 30 seconds to ensure all extracts are fully reconstituted.
4.19 Incubate all samples on ice for 30–60 minutes.
4.20 Add 200 μL of distilled water to each tube. Vortex.
4.21 Transfer 100 μL of each sample extract to respective tube.
   Note: NSB, TB, TC, Standard Curve samples, and QCs are typically run in triplicate, requiring three tubes per sample. Human plasma samples many be tested in any variation (up to three replicates) depending on sample availability.
4.22 Prepare Rabbit anti-PYY as described in the Peninsula Laboratories kit insert.
4.23 Add 100 μL RIAB to each NSB tube.
4.24 Add 200 μL RIAB to each TC tube.
4.25 Add 100 μL Rabbit anti-PYY to all remaining tubes. Vortex.
4.26 Cover with foil and store overnight at 2–8° C.

Day 3
4.27 Remove the tubes from the 2–8° C. cooler.
4.28 Prepare $^{125}$I-Peptide YY tracer (Attachment #2).
4.29 Add 100 μL of prepared tracer to all tubes. Cap and vortex.
4.30 Store overnight at 2–8° C.

Day 4
4.31 Remove the tubes from the 2–8° C. cooler.
4.32 Prepare Goat anti-Rabbit IgG serum (GARGG) and Normal Rabbit Serum (NRS) as described in the Peninsula Laboratories kit insert.
4.33 Add 100 μL GARGG to each tube (except TC tubes).
4.34 Add 100 μL NRS to each tube (except TC tubes). Vortex.
4.35 Incubate 90–120 minutes at room temperature.
4.36 Add 500 μL RIAB to tubes to be centrifuged immediately (except TC tubes). Vortex.
  Note: 500 μL RIAB should be added to tubes just prior to centrifugation. Only add RIAB to the number of tubes that are ready to be centrifuged. 500 μL RIAB should be added to additional tubes when they are ready to be centrifuged.
4.37 Centrifuge tubes (containing 500 μL RIAB) at 3000 rpm at 4° C., for 15 minutes. Do not centrifuge TC tubes.
4.38 Aspirate supernatant from centrifuged tubes.
4.39 Place tubes in designated black racks for counting on the Gamma counter. The first rack should have the appropriate Program number attached. All racks that follow should contain no program number. Samples should beadded in the following order:
  4.39.1 NSB tubes
  4.39.2 TB tubes
  4.39.3 TC tubes
  4.39.4 Standard tubes (increasing concentration)
  4.39.5 QC samples (3 concentrations)
  4.39.6 Unknown human samples
  4.39.7 QC samples (3 concentrations)
4.40 Place an empty black rack with the Stop label attached after all samples to be counted.
4.41 Press 'Start' on the Gamma Counter keypad to start counting.
4.42 Press 'E' for enter on the Gamma Counter keypad to display CPM results.

5.0 Evaluation of Results
5.1 The following guidelines are applied to the identification and rejection of outliers in the assay. In order for a result to qualify as an outlier and not be included in the final calculation of results, all of the following conditions must be met.
  5.1.1 QCs and unknown samples:
    5.1.1.1 % CV of all replicates must be great than 20%.
    5.1.1.2 There must be at least three results to evaluate.
    5.1.1.3 The difference between the suspected outlier and the result next closest in value must be greater than 20%.
    5.1.1.4 The difference between the high and low remaining results must be less than 20%.
  5.1.2 Standard Curve samples:
    5.1.2.1 % CV of all replicates much be greater than 15%.
    5.1.2.2 There must be at least three results to evaluate.
    5.1.2.3 The difference between the suspected outlier and the result next closest in value must be greater than 15%.
    5.1.2.4 The difference between the high and low remaining results must be less than 15%.

6.0 Assay Specifications
6.1 QC samples are prepared at the following concentrations. Two QC samples at each concentration are tested in an assay. Four of the six QC samples tested must be within the following ranges (±30% of nominal concentration). At least one of the two QCs tested at any concentration must be within range of the assay for data to be acceptable.

| | | |
|---|---|---|
| 6.1.1 | QC1 (100 pg/mL) | 70–130 pg/mL |
| 6.1.2 | QC2 (200 pg/mL) | 140–260 pg/mL |
| 6.1.3 | QC3 (500 pg/mL) | 350–650 pg/mL |

6.2 Standard curve parameter requirements TBD.

PYY RIA Standard:

| Tube designation | Concentration of Standard |
|---|---|
| A | 1280 pg/mL |
| B | 640 pg/mL |
| C | 320 pg/mL |
| D | 160 pg/mL |
| E | 80 pg/mL |
| F | 40 pg/mL |
| G | 20 pg/mL |
| H | 10 pg/mL |

Attachment #1
  0.6% TX-100
Reagent: 0.6% TX-100
Materials: Milli-Q Distilled Water
  TX-100
Preparation:
  1) Measure 50 mL of Milli-Q Distilled Water
  2) Add 300 μL of TX-100 using positive displacement pipette
  3) Mix well.

Attachment #2
  $^{125}$I-Peptide PYY Tracer
Reagent: $^{125}$I-Peptide PYY Tracer
Materials: 1×RIA Buffer $^{125}$I-Peptide PYY
Preparation:
  1) Reconstitute tracer with 1 mL of 1×RIA Buffer.
  2) Measure the quantity of the tracer on the Gamma Counter. Transfer 10 μL of reconstituted tracer to a tube. Place it in a black rack for the Gamma Counter with Program #30 attached.
  3) Place rack on the Gamma Counter with the Stop rack behind it.
  4) Press 'Start" to begin counting, then 'E' to view CPM results.
  5) Determine amount of tracer (X μL) to prepare and RIAB (Y mL) needed as follows:

$$X \ \mu L = \frac{(5 \ \mu L)(cpm \ \text{value})(\# \ \text{tubes} + 10)}{(cpm \ \text{from stock solution})}$$

$$Y \ mL = (0.1)(\# \ \text{tubes} + 10)$$

6) Combine X μL of $^{125}$I-Peptide YY with Y mL of RIAB. Mix well.

EXAMPLE 11

Preparation of an NPY Formulation Free of a Stabilizer that is a Protein

A PYY formulation suitable for intranasal administration of NPY, which is substantially free of a stabilizer that is a protein is prepared having the formulation listed below.
1. About ¾ of the water is added to a beaker and stirred with a stir bar on a stir plate and the sodium citrate is added until it is completely dissolved.
2. The EDTA is then added and stirred until it is completely dissolved.
3. The citric acid is then added and stirred until it is completely dissolved.
4. The methyl-β-cyclodextrin is added and stirred until it is completely dissolved.
5. The DDPC is then added and stirred until it is completely dissolved.
6. The lactose is then added and stirred until it is completely dissolved.
7. The sorbitol is then added and stirred until it is completely dissolved.
8. The chlorobutanol is then added and stirred until it is completely dissolved.
9. The NPY(3–36) is added and stirred gently until it dissolved.
10. Check the pH to make sure it is 5.0±0.25. Add dilute HCl or dilute NaOH to adjust the pH.
11. Add water to final volume.

TABLE 10

| Reagent | Grade | Vendor | mg/mL | % |
|---|---|---|---|---|
| Chlorobutanol, anhydrous | NF | Spectrum | 5.0 | 0.50 |
| Methyl-β-Cyclodextrin | | Sigma | 45 | 4.5 |
| L-α-Phosphatidylcholine Didecanoyl | | Sigma | 1 | 0.1 |
| Edetate Disodium (EDTA) | USP | Dow Chemicals | 1 | 0.1 |
| Sodium Citrate, Dihydrate | USP | Spectrum | 1.62 | 0.162 |
| Citric Acid, Anhydrous | USP | Sigma | 0.86 | 0.086 |
| α-Lactose monohydrate | | Sigma | 9 | 0.9 |
| Sorbitol | | Sigma | 18.2 | 1.82 |
| NPY(3-36) | GMP | Bachem | 1 | 0.1 |
| Purified Water | | | | |

Formulation pH 5 +/− 0.25
Osmolarity ~250

EXAMPLE 12

A second formulation is prepared as above, except the concentration of NPY(3–36) is 15 mg/mL as shown below in Table 13.

TABLE 11

| Reagent | Grade | Vendor | mg/ml | % |
|---|---|---|---|---|
| Chlorobutanol, anhydrous | NF | Spectrum | 5.0 | 0.50 |
| Methyl-β-Cyclodextrin | | Sigma | 45 | 4.5 |
| L-α-Phosphatidylcholine Didecanoyl | | Sigma | 1 | 0.1 |
| Edetate Disodium | USP | Dow Chemicals | 1 | 0.1 |
| Sodium Citrate, Dihydrate | USP | Spectrum | 1.62 | 0.162 |
| Citric Acid, Anhydrous | USP | Sigma | 0.86 | 0.086 |
| α-Lactose monohydrate | | Sigma | 9 | 0.9 |
| Sorbitol | | Sigma | 18.2 | 1.82 |
| NPY(3-36) | GMP | Bachem | 15 | 0.1 |
| Purified Water | | | | |

Formulation pH 5 +/− 0.25

EXAMPLE 13

Preparation of Pancreatic Peptide (PP) Formulation Free of a Stabilizer that is a Protein A PYY formulation suitable for intranasal administration of PP, which is substantially free of a stabilizer that is a protein is prepared having the formulation listed below.
1. About ¾ of the water is added to a beaker and stirred with a stir bar on a stir plate and the sodium citrate is added until it is completely dissolved.
2. The EDTA is then added and stirred until it is completely dissolved.
3. The citric acid is then added and stirred until it is completely dissolved.
4. The methyl-β-cyclodextrin is added and stirred until it is completely dissolved.
5. The DDPC is then added and stirred until it is completely dissolved.
6. The lactose is then added and stirred until it is completely dissolved.
7. The sorbitol is then added and stirred until it is completely dissolved.
8. The chlorobutanol is then added and stirred until it is completely dissolved.
9. The PP(3–36) is added and stirred gently until it dissolved.
10. 11 Check the pH to make sure it is 5.0±0.25. Add dilute HCl or dilute NaOH to adjust the pH.
11. Add water to final volume.

TABLE 12

| Reagent | Grade | Vendor | mg/mL | % |
|---|---|---|---|---|
| Chlorobutanol, anhydrous | NF | Spectrum | 5.0 | 0.50 |
| Methyl-β-Cyclodextrin | | Sigma | 45 | 4.5 |
| L-α-Phosphatidylcholine Didecanoyl | | Sigma | 1 | 0.1 |
| Edetate Disodium | USP | Dow Chemicals | 1 | 0.1 |
| Sodium Citrate, Dihydrate | USP | Spectrum | 1.62 | 0.162 |
| Citric Acid, Anhydrous | USP | Sigma | 0.86 | 0.086 |
| α-Lactose monohydrate | | Sigma | 9 | 0.9 |
| Sorbitol | | Sigma | 18.2 | 1.82 |
| PP(3-36) | GMP | Bachem | 1 | 0.1 |
| Purified Water | | | | |

Formulation pH 5 +/− 0.25
Osmolarity ~250

EXAMPLE 14

A second formulation is prepared as above, except the concentration of PP(3–36) is 15 mg/mL as shown below in Table 13.

TABLE 13

| Reagent | Grade | Vendor | mg/ml | % |
|---|---|---|---|---|
| Chlorobutanol, anhydrous | NF | Spectrum | 5.0 | 0.50 |
| Methyl-β-Cyclodextrin | | Sigma | 45 | 4.5 |
| L-α-Phosphatidylcholine Didecanoyl | | Sigma | 1 | 0.1 |
| Edetate Disodium | USP | Dow Chemicals | 1 | 0.1 |
| Sodium Citrate, Dihydrate | USP | Spectrum | 1.62 | 0.162 |
| Citric Acid, Anhydrous | USP | Sigma | 0.86 | 0.086 |
| α-Lactose monohydrate | | Sigma | 9 | 0.9 |
| Sorbitol | | Sigma | 18.2 | 1.82 |
| PP(3-36) | GMP | Bachem | 15 | 0.1 |
| Purified Water | | | | |

Formulation pH 5 +/− 0.25

EXAMPLE 15

This example describes a pharmaceutical composition product comprising an aqueous solution formulation of a Y2 receptor binding compound at a concentration sufficient to produce therapeutically effective plasma concentrations and an actuator to produce an aerosol of said solution, wherein the spray pattern ellipticity ratio of said aerosol is between 1.00 and 1.40 when measured at a height of between 0.5 cm and 10 cm distance from the actuator tip.

Surprisingly a PYY(3–36) formulation of the instant specification can be aerosolized and still be therapeutically effective (as shown in Example 8a). The volume of the aerosol can be between about 5 microliters and 2.5 ml, preferably between 20 and 200 microliters.

This test method describes the procedure for characterizing plume geometry of Y2 receptor binding compound nasal solution formulations using the SprayView NSP system. The plume geometry is characterized using a SprayView High Speed Optical Spray Characterization System (SprayView NSP) with Integrated SprayView NSx actuation station (Image Therm Engineering, Inc., Sudbury, Mass.) according to the methods described in U.S. Pat. No. 6,665,421 and U.S. Patent Application Publication No. 20030018416, published Jan. 23, 2003.

Using the formulation of table 14 or placebo the spray characterization and droplet size of the formulation in both a 1 mL and a 3 mL bottle both having a nasal Spray Pump w/Safety Clip, Pfeiffer SAP #60548, which delivers a dose of 0.1 mL per squirt and has a diptube length of 36.05 mm.

The droplet size data are shown in the following table.

Droplet Size for Nasal Spray Bottle and Pfeiffer SAP #60548

|  |  | $D_{10}$ | $D_{50}$ | $D_{90}$ | Span | % <10 micrometer |
|---|---|---|---|---|---|---|
| 1 mL | Y2 Receptor binding compound (PYY) | 33.36 | 229.21 | 704.66 | 3.23 | 0.29 |
| 3 mL | Y2 receptor binding compound (PYY) | 23.26 | 92.31 | 610.46 | 6.60 | 0.59 |

Below are listed the spray pattern and plume geometry results

| Spray Pattern |  | Major Axis | Minor Axis | Ellipticity Ratio | Dmin | Dmax | Ovality | Pattern Area |
|---|---|---|---|---|---|---|---|---|
| active | 1 mL | 25.0 | 21.1 | 1.2 | 20.1 | 26.4 | 1.3 | 419.4 |
|  | 3 mL | 26.5 | 22.6 | 1.2 | 22.1 | 29.1 | 1.3 | 468.2 |

| Plume Geometry |  | Angle | Width |
|---|---|---|---|
| active | 1 mL | 48.5 | 27.1 |
|  | 3 mL | 44.8 | 25.0 |

EXAMPLE 16

Subcutaneous Injection of PYY

PYY3–36/PEG Sustained Release Formulation 10.3 milligrams of a PYY3–36 is weighed out and suspended in 0.5 ml of PEG 400 (Sigma Chemical) by gentle shaking to yield a dispersible suspension containing about 20.6 mg PYY3–36/ml.

EXAMPLE 17

Controlled Release Potential of PYY in a Protamine Vehicle

PYY3–36 is prepared in 10 mM sodium acetate, 10 mM zinc acetate, 0.4 mM protamine sulfate, pH 5.5 buffer. This can be use to administered PYY3–36 by means of a subcutaneous injection, which is released as a slow controlled release formulation.

EXAMPLE 18

An aqueous solution of PYY3–36 1 mg/mL (100 mL) and 2% atelocollagen (a collagen which is obtained by removing the telopeptide region by treating collagen with an enzyme (e.g. pepsin) in order to make it safer) (50 g) are homogeneously mixed by stirring while preventing the occurrence of foam as much as possible. The mixture is lyophilized and pulverized at a low temperature using liquid nitrogen. The pulverized product thus obtained is suspended in sesame oil to give an oily suspension type, sustained-release preparation of PYY

EXAMPLE 19

An aqueous solution of PYY 1 mg/mL (100 mL) and 2% collagen (50 g) are homogeneously mixed by stirring while preventing the occurrence of foam as much as possible. The mixture is lyophilized and pulverized at a low temperature using liquid nitrogen. The pulverized product thus obtained is suspended in sesame oil to give an oily suspension type of PYY3–36.

EXAMPLE 20

An aqueous solution of PYY3–36 1 mg/mL (100 mL), 2% atelocollagen (50 g), human serum albumin (150 mg) and thimerosal (120 .mu.µg) are homogeneously mixed while preventing the occurrence of foam as much as possible. The mixture is lyophilized and pulverized at a low temperature using liquid nitrogen. The pulverized product thus obtained is suspended in sesame oil to give an oily suspension type, sustained-release preparation of PYY3–36 suitable for subcutaneous injection.

EXAMPLE 21

An aqueous solution of PYY3–36 1 mg/mL (100 mL) and gelatin (1 g) are homogeneously mixed at 60° C. while preventing the occurrence of foam as much as possible. The mixture is lyophilized and pulverized at a low temperature using liquid nitrogen. The pulverized product thus obtained is suspended in sesame oil to give an oily suspension type, sustained-release preparation containing PYY3–36.

EXAMPLE 22

The pulverized product prepared in the same manner as described in Example 1 is suspended in castor oil to give an oily suspension type, sustained-release preparation containing PYY3–36.

EXAMPLE 23

The pulverized PYY3–36 product prepared in the same manner as described in Example 1 is suspended in polyethylene glycol to give a suspension type, sustained-release preparation wherein containing PYY3–36.

EXAMPLE 24

The pulverized product prepared in the same manner as described in Example 1 is suspended in iodinated poppy seed oil fatty acids ethyl esters (sold by Libiodol Ultrafluid—Kodama Shoji) to give an oily suspendion suspension type, sustained-release preparation PYY3–36 suitable for subcutaneous injection.

EXAMPLE 25

Gelatin (10 g) is dissolved in distilled water (100 ml). To the solution (5 ml) is added 20 mg of PYY3–36, and the mixture is lyophilized. The lyophilized product is pulverized at a low temperature using liquid nitrogen to obtain a powder of PYY3–36—gelatin composite. The powdery composite (100 mg) is suspended in sesame oil (5 mL) to give a sustained-release oily suspension suitable for subcutaneous injection.

EXAMPLE 26

PYY3–36 (1 mg) is dissolved in a phosphate buffer containing 2% atelocollagen (2 ml), and the solution is lyophilized. The composite thus obtained is pulverized at a low temperature using liquid nitrogen and then suspended in polyethylene glycol (3 ml) to give a sustained-release oily suspension suitable for subcutaneous injection.

EXAMPLE 27

PYY3–36 (1 mg) is dissolved in a phosphate buffer containing 2% atelocollagen (2 ml), and the solution is lyophilized. The composite thus obtained is pulverized at a low temperature using liquid nitrogen and then suspended in cotton seed oil (5 ml) to give a sustained-release oily suspension of PYY3–36 suitable for subcutaneous injection.

EXAMPLE 28

PYY3–36 (3 mg) is dissolved in 10% aqueous gelatin solution (3 mL) and the solution is lyophilized. The composite thus obtained is pulverized at a low temperature using liquid nitrogen, and the pulverized product is suspended in polyethylene glycol (5 ml) to give a sustained-release oily suspension of PYY3–36 suitable for subcutaneous injection.

EXAMPLE 29

PYY Formulations Having Varying Osmolarity

| Sample | Composition | Comments |
|---|---|---|
| 1 | 1 mg/mL PYY, 45 mg/mL M-b-CD, 1 mg/mL EDTA, 1 mg/mL DDPC, 10 mM citrate buffer pH 3.8, 25 mM lactose, 100 mM sorbitol, 0.5% CB | pH 3.8 and 225 mOsm |
| 2 | 1 mg/mL PYY, 45 mg/mL M-b-CD, 1 mg/mL EDTA, 1 mg/mL DDPC, 10 mM citrate buffer pH 4.1, 25 mM lactose, 100 mM sorbitol, 0.5% CB | pH 4.1 and 225 mOsm |
| 3 | 1 mg/mL PYY, 45 mg/mL M-b-CD, 1 mg/mL EDTA, 1 mg/mL DDPC, 10 mM citrate buffer pH 4.3, 25 mM lactose, 100 mM sorbitol, 0.5% CB | pH 4.3 and 225 mOsm |
| 4 | 1 mg/mL PYY, 45 mg/mL M-b-CD, 1 mg/mL EDTA, 1 mg/mL DDPC, 10 mM citrate buffer pH 4.7, 25 mM lactose, 100 mM sorbitol, 0.5% CB | pH 4.7 and 225 mOsm |
| 5 | 1 mg/mL PYY, 45 mg/mL M-b-CD, 1 mg/mL EDTA, 1 mg/mL DDPC, 10 mM citrate buffer pH 5.0, 25 mM lactose, 100 mM sorbitol, 0.5% CB | Current lead formulation; pH 5.0 and 225 mOsm |
| 6 | 1 mg/mL PYY, 45 mg/mL M-b-CD, 1 mg/mL EDTA, 1 mg/mL DDPC, 10 mM citrate buffer pH 5.3, 25 mM lactose, 100 mM sorbitol, 0.5% CB | pH 5.3 and 225 mOsm |
| 7 | 1 mg/mL PYY, 45 mg/mL M-b-CD, 1 mg/mL EDTA, 1 mg/mL DDPC, 10 mM citrate buffer pH 5.00, 52.5 mM NaCl, 0.5% CB | pH 5.0 and 200 mOsm |
| 8 | 1 mg/mL PYY, 45 mg/mL M-b-CD, 1 mg/mL EDTA, 1 mg/mL DDPC, 10 mM citrate buffer pH 5.00, 65.0 mM NaCl, 0.5% CB | pH 5.0 and 225 mOsm |
| 9 | 1 mg/mL PYY, 45 mg/mL M-b-CD, 1 mg/mL EDTA, 1 mg/mL DDPC, 10 mM citrate buffer pH 5.00, 77.5 mM NaCl, 0.5% CB | pH 5.0 and 250 mOsm |
| 10 | 1 mg/mL PYY, 45 mg/mL M-b-CD, 1 mg/mL EDTA, 1 mg/mL DDPC, 10 mM citrate buffer pH 5.00, 90.0 mM NaCl, 0.5% CB | pH 5.0 and 275 mOsm |
| 11 | 1 mg/mL PYY, 45 mg/mL M-b-CD, 1 mg/mL EDTA, 1 mg/mL DDPC, 10 mM citrate buffer pH 5.00, 102.5 mM NaCl, 0.5% CB | pH 5.0 and 300 mOsm |
| 12 | 1 mg/mL PYY, 45 mg/mL M-b-CD, 1 mg/mL EDTA, 1 mg/mL DDPC, 57.5 mM citrate buffer pH 5.00, 0.5% CB | Increase citrate buffer concentration; pH 5.0 and 225 mOsm |

-continued

| Sample | Composition | Comments |
|---|---|---|
| 13 | 1 mg/mL PYY, 45 mg/mL M-b-CD, 1 mg/mL EDTA, 1 mg/mL DDPC, 10 mM citrate buffer pH 5.00, 0.5% CB | No sugars; pH 5.0 and 90 mOsm |
| 14 | 1 mg/mL PYY, 45 mg/mL M-b-CD, 1 mg/mL EDTA, 1 mg/mL DDPC, 10 mM citrate buffer pH 5.00, 25 mM Trehalose, 40 mM NaCl, 0.5% CB | Trehalose and NaCl; pH 5.0 and 225 mOsm |
| 15 | 1 mg/mL PYY, 45 mg/mL M-b-CD, 1 mg/mL EDTA, 1 mg/mL DDPC, 10 mM citrate buffer pH 5.00, 1% Pluronic F 68, 60 mM NaCl, 0.5% CB | Pluronic F68 and NaCl; pH 5.0 and 225 mOsm |
| 16 | 1 mg/mL PYY, 45 mg/mL M-b-CD*, 1 mg/mL EDTA, 1 mg/mL DDPC, 10 mM citrate buffer pH 5.0, 25 mM lactose, 100 mM sorbitol, 0.5% CB | Current lead formulation; pH 5.0 and 225 mOsm |
| 17 | 1 mg/mL PYY, 45 mg/mL M-b-CD*, 1 mg/mL EDTA, 1 mg/mL DDPC, 10 mM citrate buffer pH 5.0, 25 mM lactose, 100 mM sorbitol, 0.2% sorbic acid | 0.2% sorbic acid |
| 18 | 1 mg/mL PYY, 10 mM citrate (pH 5), 135 mM NaCl | Perm Control |
| 19 | Media | MTT std, TER control |
| 20 | 9% Triton X-100 | LDH control |

EXAMPLE 30

Preparation of an Alternative PYY Formulation Free of a Stabilizer that is a Protein A PYY formulation suitable for intranasal administration of PYY, which was substantially free of a stabilizer that is a protein was prepared having the formulation listed below.

12. About ¾ of the water was added to a beaker and stirred with a stir bar on a stir plate and the sodium citrate was added until it was completely dissolved.
13. The EDTA was then added and stirred until it was completely dissolved.
14. The citric acid was then added and stirred until it was completely dissolved.
15. The methyl-β-cyclodextrin was added and stirred until it was completely dissolved.
16. The DDPC was then added and stirred until it was completely dissolved.
17. The lactose was then added and stirred until it was completely dissolved.
18. The sorbitol was then added and stirred until it was completely dissolved.
19. The chlorobutanol was then added and stirred until it was completely dissolved.
20. The PYY 3–36 was added and stirred gently until it dissolved.
21. 11 Check the pH to make sure it is 5.0±0.25. Add dilute HCl or dilute NaOH to adjust the pH.
22. Add water to final volume.

| Reagent | Grade | Vendor | mg/mL | % |
|---|---|---|---|---|
| CholorbutanolChlorobutanol, anhydrous | NF | Spectrum | 5.0 | 0.50 |
| Methyl-β-Cyclodextrin | | Sigma | 45 | 4.5 |
| L-α-Phosphatidylcholine Didecanoyl | | Sigma | 1 | 0.1 |
| Edetate Disodium | USP | Dow Chemicals | 1 | 0.1 |
| Sodium Citrate, Dihydrate | USP | Spectrum | 1.75 | 0.175 |
| Citric Acid, Anhydrous | USP | Sigma | 0.78 | 0.078 |
| α-Lactose monohydrate | | Sigma | 9 | 0.9 |
| Sorbitol | | Sigma | 18.2 | 1.82 |
| PYY 3-36 | GMP | Bachem | 1 | 0.1 |
| Purified Water | | | | |

Formulation pH 5 +/− 0.25
Osmolarity ~225

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation.

What is claimed is:

1. A method for treating a mammal for obesity, inducing weight-loss or to induce satiety in the mammal comprised of intranasally administering to said mammal a therapeutically effective amount of a composition comprising a Y2 receptor-binding peptide, and L-α-phosphatidylcholine didecanoyl (DDPC), resulting in an increase in concentration of the Y2 receptor-binding peptide in the mammal by at least 5 pmol per liter of plasma to about 60 pmol per liter of plasma.

2. The method of claim 1 wherein the mammal is human.

3. The method of claim 2 wherein the Y2 receptor-binding peptide is a PYY peptide.

4. The method of claim 3 wherein the Y2 receptor binding peptide is administered from 30 to 90 minutes prior to when the human eats food.

5. The method of claim 4 wherein the Y2 receptor-binding peptide is a PYY(3–36) peptide comprised of the amino acid sequence of SEQ ID NO: 2.

6. A method for treating a mammal for obesity, inducing weight-loss or to induce satiety in the mammal comprised of intranasally administering to said mammal 40 μg to 200 μg of a Y2 receptor binding peptide.

7. The method of claim 6 wherein the mammal is human.

8. The method of claim 7 wherein the Y2 receptor-binding peptide is a PYY peptide.

9. The method of claim 8 wherein the Y2 receptor binding peptide is administered from 30 to 90 minutes prior to when the human eats food.

10. The method of claim 9 wherein the Y2 receptor-binding peptide is a PYY(3–36) peptide comprised of the amino acid sequence of SEQ ID NO: 2.

11. A method for treating a mammal for obesity, inducing weight-loss or to induce satiety in the mammal comprised of intranasally administering to said mammal 45 μg to 150 μg of a composition comprising a Y2 receptor-binding peptide, and L-α-phosphatidylcholine didecanoyl (DDPC).

12. The method of claim 11 wherein the mammal is human.

13. The method of claim 12 wherein the Y2 receptor-binding peptide is a PYY peptide.

14. The method of claim 13 wherein the Y2 receptor binding peptide is administered from 30 to 90 minutes prior to when the human eats food.

15. The method of claim 14 wherein the Y2 receptor-binding peptide is a PYY(3–36) peptide comprised of the amino acid sequence of SEQ ID NO: 2.

16. A method for treating a mammal for obesity, inducing weight-loss or to induce satiety in the mammal comprised of intranasally administering to said mammal 50 μg to 100 μg of a composition comprising a Y2 receptor-binding peptide, and L-α-phosphatidylcholine didecanoyl (DDPC).

17. The method of claim 16 wherein the mammal is human.

18. The method of claim 17 wherein the Y2 receptor-binding peptide is a PYY peptide.

19. The method of claim 18 wherein the Y2 receptor binding peptide is administered from 30 to 90 minutes prior to when the human eats food.

20. The method of claim 19 wherein the Y2 receptor-binding peptide is a PYY(3–36) peptide comprised of the amino acid sequence of SEQ ID NO: 2.

21. A method for treating a mammal for obesity, inducing weight-loss or to induce satiety in the mammal comprised of intranasally administering to said mammal about 55 μg to about 85 μg of a composition comprising a Y2 receptor-binding peptide and L-α-phosphatidylcholine didecanoyl (DDPC).

22. The method of claim 21 wherein the mammal is human.

23. The method of claim 22 wherein the Y2 receptor-binding peptide is a PYY peptide.

24. The method of claim 23 wherein the Y2 receptor binding peptide is administered from 30 to 90 minutes prior to when the human eats food.

25. The method of claim 24 wherein the Y2 receptor-binding peptide is a PYY(3–36) peptide comprised of the amino acid sequence of SEQ ID NO: 2.

26. A method for treating a mammal for obesity, inducing weight-loss or to induce satiety in the mammal comprised of intranasally administering to said mammal 65 μg to 75 μg of a composition comprising a Y2 receptor-binding peptide, and L-α-phosphatidylcholine didecanoyl (DDPC).

27. The method of claim 26 wherein the mammal is human.

28. The method of claim 1 wherein the composition is further comprised of at least two polyols.

29. The method of claim 28 wherein the polyols are selected from the group consisting of sucrose, mannitol, sorbitol, lactose, L-arabinose, D-erythrose, D-ribose, D-xylose, D-mannose, trehalose, D-galactose, lactulose, cellobiose, gentibiose, glycerin and polyethylene glycol.

30. The method of claim 29 wherein the polyols are lactose and sorbitol.

31. The method of claim 1 wherein the chelating agent is ethylene diamine tetraacetic acid (EDTA) or ethylene glycol tetraacetic acid (EGTA).

32. The method of claim 31 wherein the chelating agent is ethylenediamine tetraacetic acid (EDTA).

33. The method of claim 1 wherein the solubilizing agent is selected from the group consisting of a cyclodextran, hydroxypropyl-β-cyclodextran, sulfobutylether-β-cyclodextran and methyl-β-cyclodextrin.

34. The method of claim 33 wherein the solubilizing agent is a methyl-β-cyclodextrin.

35. The method of claim 1 wherein the composition is an aqueous PYY composition.

36. The method of claim 35 wherein the aqueous PYY composition has a pH from about 3 to about 6.

37. The method of claim 36 wherein the aqueous PYY composition has a pH of about 5.0±0.3.

38. The method of claim 11 wherein the composition is further comprised of at least two polyols.

39. The method of claim 38 wherein the polyols are selected from the group consisting of sucrose, mannitol, sorbitol, lactose, L-arabinose, D-erythrose, D-ribose, D-xylose, D-mannose, trehalose, D-galactose, lactulose, cellobiose, gentibiose, glycerin and polyethylene glycol.

40. The method of claim 39 wherein the polyols are lactose and sorbitol.

41. The method of claim 11 wherein the chelating agent is ethylene diamine tetraacetic acid (EDTA) or ethylene glycol tetraacetic acid (EGTA).

42. The method of claim 41 wherein the chelating agent is ethylenediamine tetraacetic acid (EDTA).

43. The method of claim 11 wherein the solubilizing agent is selected from the group consisting of a cyclodextran, hydroxypropyl-β-cyclodextran, sulfobutylether-β-cyclodextran and methyl-β-cyclodextrin.

44. The method of claim 43 wherein the solubilizing agent is a methyl-β-cyclodextrin.

45. The method of claim 11 wherein the composition is an aqueous PYY composition further comprised of water.

46. The method of claim 45 wherein the aqueous PYY composition has a pH from about 3 to about 6.

47. The method of claim 46 wherein the aqueous PYY composition has a pH of about 5.0±0.3.

48. The method of claim 35 wherein the aqueous PYY composition is free of a protein stabilizer.

49. The method of claim 35 wherein the aqueous PYY composition is an emulsion.

50. The method of claim 35 wherein the aqueous PYY composition is a solution.

* * * * *

UNITED STATES PATENT AND TRADEMARK OFFICE
CERTIFICATE OF CORRECTION

PATENT NO.       : 7,186,692 B2
APPLICATION NO.  : 10/869649
DATED            : March 6, 2007
INVENTOR(S)      : Steven C. Quay et al.

It is certified that error appears in the above-identified patent and that said Letters Patent is hereby corrected as shown below:

Title Page,
Item (56) References Cited,

OTHER PUBLICATIONS:
Page 2,
Col. 2, line 8, "Hiroyuki Minakata," reference, delete "amphipihlic" and insert -- amphiphilic --.
Col. 2, line 29, "Inui Akio," reference, delete "Amerian" and insert -- American" --.
Col. 2, line 42, "Grandt, D.;" reference, delete "PYY(93-36)," and insert -- PYY(3-36), --.
Col. 2, line 58, "Margaret Dos Santos Medeiros," reference, delete "Vo 134," and insert -- Vol. 134, --.

Page 3,
Col. 1, line 26, "R.L. Batterham," reference, delete "Clincal" and insert -- Clinical --.
Col. 1, line 29, "Von E. Niebergall-Roth, S." reference, delete "gastrointestinaltrakies," and insert -- gastrointestinaltraktes, --.
Col. 1, line 37, "Chen, C. H.;" reference, delete "Neurogastroenlarol.Motil." and insert --Neurogastroenterol.Motil. --.

Column 1,
Line 44, after "as well" insert -- as --.

Column 6,
Line 20, delete "a" and insert -- an --.

Column 10,
Line 65, delete "A mucosally".

Column 14,
Line 47, delete "last1 1" and insert -- last 11 --.

Column 15,
Line 6, delete "NPY26-36" and insert -- NPY(26-36) --.

Column 17,
Line 8, delete "dihyropyridine." and insert -- dihydropyridine. --.

Column 34,
Line 27, after "effects" insert -- . --.

UNITED STATES PATENT AND TRADEMARK OFFICE
CERTIFICATE OF CORRECTION

| | |
|---|---|
| PATENT NO. | : 7,186,692 B2 |
| APPLICATION NO. | : 10/869649 |
| DATED | : March 6, 2007 |
| INVENTOR(S) | : Steven C. Quay et al. |

It is certified that error appears in the above-identified patent and that said Letters Patent is hereby corrected as shown below:

Column 60,
Line 62, delete "The a Y2" and insert -- The Y2 --.

Column 66,
Line 36, after "mg/mL" insert -- . --.

Column 72,
Line 33, delete "A G," and insert -- AG, --.

Column 76,
Line 5, delete "11 Check" and insert -- Check --.

Column 83,
Line 67, delete "according of to" and insert -- according to --.

Column 84,
Line 19, delete "PYY3-36," and insert -- PYY(3-36), --.

Column 86,
Line 52, delete "many" and insert -- may --.

Column 87,
Lines 23-24, delete "beadded" and insert -- be added --.
Line 47, delete "great" and insert -- greater --.
Line 56, delete "much" and insert -- must --.

Column 90,
Line 28, delete "11 Check" and insert -- Check --.

Column 92,
Line 20, delete "can be use to administered" and insert -- can be used to administer --.

Column 93,
Line 44, delete "suspendion".

UNITED STATES PATENT AND TRADEMARK OFFICE
CERTIFICATE OF CORRECTION

PATENT NO. : 7,186,692 B2
APPLICATION NO. : 10/869649
DATED : March 6, 2007
INVENTOR(S) : Steven C. Quay et al.

It is certified that error appears in the above-identified patent and that said Letters Patent is hereby corrected as shown below:

Column 96,
Line 21, delete "Cholorbutanol".

Signed and Sealed this

Thirteenth Day of November, 2007

JON W. DUDAS
*Director of the United States Patent and Trademark Office*

SEQUENCE LISTING

```
<160> NUMBER OF SEQ ID NOS: 105

<210> SEQ ID NO 1
<211> LENGTH: 36
<212> TYPE: PRT
<213> ORGANISM: Homo sapiens

<400> SEQUENCE: 1

Tyr Pro Ile Lys Pro Glu Ala Pro Gly Glu Asp Ala Ser Pro Glu Glu
 1               5                  10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 2
<211> LENGTH: 34
<212> TYPE: PRT
```

<213> ORGANISM: Homo sapiens

<400> SEQUENCE: 2

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 3
<211> LENGTH: 15
<212> TYPE: PRT
<213> ORGANISM: Homo sapiens

<400> SEQUENCE: 3

Ala Ser Leu Arg His Tyr Leu Asn Leu Val Thr Arg Gln Arg Tyr
1               5                   10                  15

<210> SEQ ID NO 4
<211> LENGTH: 33
<212> TYPE: PRT
<213> ORGANISM: Homo sapiens

<400> SEQUENCE: 4

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Leu Val Thr Arg Gln Arg
            20                  25                  30

Tyr

<210> SEQ ID NO 5
<211> LENGTH: 32
<212> TYPE: PRT
<213> ORGANISM: Homo sapiens

<400> SEQUENCE: 5

Pro Glu Ala Pro Gly Glu Asp Ala Ser Pro Glu Glu Leu Asn Arg Tyr
1               5                   10                  15

Tyr Ala Ser Leu Arg His Tyr Leu Asn Leu Val Thr Arg Gln Arg Tyr
            20                  25                  30

<210> SEQ ID NO 6
<211> LENGTH: 31
<212> TYPE: PRT
<213> ORGANISM: Homo sapiens

<400> SEQUENCE: 6

Glu Ala Pro Gly Glu Asp Ala Ser Pro Glu Glu Leu Asn Arg Tyr Tyr
1               5                   10                  15

Ala Ser Leu Arg His Tyr Leu Asn Leu Val Thr Arg Gln Arg Tyr
            20                  25                  30

<210> SEQ ID NO 7
<211> LENGTH: 30
<212> TYPE: PRT
<213> ORGANISM: Homo sapiens

<400> SEQUENCE: 7

Ala Pro Gly Glu Asp Ala Ser Pro Glu Glu Leu Asn Arg Tyr Tyr Ala
1               5                   10                  15

Ser Leu Arg His Tyr Leu Asn Leu Val Thr Arg Gln Arg Tyr 20          25          30

<210> SEQ ID NO 8
<211> LENGTH: 29
<212> TYPE: PRT
<213> ORGANISM: Homo sapiens

<400> SEQUENCE: 8

Pro Gly Glu Asp Ala Ser Pro Glu Glu Leu Asn Arg Tyr Tyr Ala Ser
1               5                   10                  15

Leu Arg His Tyr Leu Asn Leu Val Thr Arg Gln Arg Tyr
            20                  25

<210> SEQ ID NO 9
<211> LENGTH: 28
<212> TYPE: PRT
<213> ORGANISM: Homo sapiens

<400> SEQUENCE: 9

Gly Glu Asp Ala Ser Pro Glu Glu Leu Asn Arg Tyr Tyr Ala Ser Leu
1               5                   10                  15

Arg His Tyr Leu Asn Leu Val Thr Arg Gln Arg Tyr
            20                  25

<210> SEQ ID NO 10
<211> LENGTH: 27
<212> TYPE: PRT
<213> ORGANISM: Homo sapiens

<400> SEQUENCE: 10

Glu Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 11
<211> LENGTH: 26
<212> TYPE: PRT
<213> ORGANISM: Homo sapiens

<400> SEQUENCE: 11

Asp Ala Ser Pro Glu Glu Leu Asn Arg Tyr Tyr Ala Ser Leu Arg His
1               5                   10                  15

Tyr Leu Asn Leu Val Thr Arg Gln Arg Tyr
            20                  25

<210> SEQ ID NO 12
<211> LENGTH: 25
<212> TYPE: PRT
<213> ORGANISM: Homo sapiens

<400> SEQUENCE: 12

Ala Ser Pro Glu Glu Leu Asn Arg Tyr Tyr Ala Ser Leu Arg His Tyr
1               5                   10                  15

Leu Asn Leu Val Thr Arg Gln Arg Tyr
            20                  25

<210> SEQ ID NO 13
<211> LENGTH: 24
<212> TYPE: PRT
<213> ORGANISM: Homo sapiens

<400> SEQUENCE: 13

Ser Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 14
<211> LENGTH: 23
<212> TYPE: PRT
<213> ORGANISM: Homo sapiens

<400> SEQUENCE: 14

Pro Glu Glu Leu Asn Arg Tyr Tyr Ala Ser Leu Arg His Tyr Leu Asn
1               5                   10                  15

Leu Val Thr Arg Gln Arg Tyr
            20

<210> SEQ ID NO 15
<211> LENGTH: 22
<212> TYPE: PRT
<213> ORGANISM: Homo sapiens

<400> SEQUENCE: 15

Glu Glu Leu Asn Arg Tyr Tyr Ala Ser Leu Arg His Tyr Leu Asn Leu
1               5                   10                  15

Val Thr Arg Gln Arg Tyr
            20

<210> SEQ ID NO 16
<211> LENGTH: 21
<212> TYPE: PRT
<213> ORGANISM: Homo sapiens

<400> SEQUENCE: 16

Glu Leu Asn Arg Tyr Tyr Ala Ser Leu Arg His Tyr Leu Asn Leu Val
1               5                   10                  15

Thr Arg Gln Arg Tyr
            20

<210> SEQ ID NO 17
<211> LENGTH: 20
<212> TYPE: PRT
<213> ORGANISM: Homo sapiens

<400> SEQUENCE: 17

Leu Asn Arg Tyr Tyr Ala Ser Leu Arg His Tyr Leu Asn Leu Val Thr
1               5                   10                  15

Arg Gln Arg Tyr
            20

<210> SEQ ID NO 18
<211> LENGTH: 19
<212> TYPE: PRT
<213> ORGANISM: Homo sapiens

<400> SEQUENCE: 18

Asn Arg Tyr Tyr Ala Ser Leu Arg His Tyr Leu Asn Leu Val Thr Arg
1               5                   10                  15

Gln Arg Tyr

<210> SEQ ID NO 19
<211> LENGTH: 18

```
<212> TYPE: PRT
<213> ORGANISM: Homo sapiens

<400> SEQUENCE: 19

Arg Tyr Tyr Ala Ser Leu Arg His Tyr Leu Asn Leu Val Thr Arg Gln
 1               5                  10                  15

Arg Tyr

<210> SEQ ID NO 20
<211> LENGTH: 17
<212> TYPE: PRT
<213> ORGANISM: Homo sapiens

<400> SEQUENCE: 20

Tyr Tyr Ala Ser Leu Arg His Tyr Leu Asn Leu Val Thr Arg Gln Arg
 1               5                  10                  15

Tyr

<210> SEQ ID NO 21
<211> LENGTH: 16
<212> TYPE: PRT
<213> ORGANISM: Homo sapiens

<400> SEQUENCE: 21

Tyr Ala Ser Leu Arg His Tyr Leu Asn Leu Val Thr Arg Gln Arg Tyr
 1               5                  10                  15

<210> SEQ ID NO 22
<211> LENGTH: 36
<212> TYPE: PRT
<213> ORGANISM: Homo sapiens

<400> SEQUENCE: 22

Tyr Pro Ser Lys Pro Asp Asn Pro Gly Glu Asp Ala Pro Ala Glu Asp
 1               5                  10                  15

Met Ala Arg Tyr Tyr Ser Ala Leu Arg His Tyr Ile Asn Leu Ile Thr
                20                  25                  30

Arg Gln Arg Tyr
         35

<210> SEQ ID NO 23
<211> LENGTH: 11
<212> TYPE: PRT
<213> ORGANISM: Homo sapiens

<400> SEQUENCE: 23

His Tyr Ile Asn Leu Ile Thr Arg Gln Arg Tyr
 1               5                  10

<210> SEQ ID NO 24
<211> LENGTH: 34
<212> TYPE: PRT
<213> ORGANISM: Homo sapiens

<400> SEQUENCE: 24

Ser Lys Pro Asp Asn Pro Gly Glu Asp Ala Pro Ala Glu Asp Met Ala
 1               5                  10                  15

Arg Tyr Tyr Ser Ala Leu Arg His Tyr Ile Asn Leu Ile Thr Arg Gln
                20                  25                  30

Arg Tyr
```

```
<210> SEQ ID NO 25
<211> LENGTH: 33
<212> TYPE: PRT
<213> ORGANISM: Homo sapiens

<400> SEQUENCE: 25

Lys Pro Asp Asn Pro Gly Glu Asp Ala Pro Ala Glu Asp Met Ala Arg
 1               5                  10                  15

Tyr Tyr Ser Ala Leu Arg His Tyr Ile Asn Leu Ile Thr Arg Gln Arg
             20                  25                  30

Tyr

<210> SEQ ID NO 26
<211> LENGTH: 32
<212> TYPE: PRT
<213> ORGANISM: Homo sapiens

<400> SEQUENCE: 26

Pro Asp Asn Pro Gly Glu Asp Ala Pro Ala Glu Asp Met Ala Arg Tyr
 1               5                  10                  15

Tyr Ser Ala Leu Arg His Tyr Ile Asn Leu Ile Thr Arg Gln Arg Tyr
             20                  25                  30

<210> SEQ ID NO 27
<211> LENGTH: 31
<212> TYPE: PRT
<213> ORGANISM: Homo sapiens

<400> SEQUENCE: 27

Asp Asn Pro Gly Glu Asp Ala Pro Ala Glu Asp Met Ala Arg Tyr Tyr
 1               5                  10                  15

Ser Ala Leu Arg His Tyr Ile Asn Leu Ile Thr Arg Gln Arg Tyr
             20                  25                  30

<210> SEQ ID NO 28
<211> LENGTH: 30
<212> TYPE: PRT
<213> ORGANISM: Homo sapiens

<400> SEQUENCE: 28

Asn Pro Gly Glu Asp Ala Pro Ala Glu Asp Met Ala Arg Tyr Tyr Ser
 1               5                  10                  15

Ala Leu Arg His Tyr Ile Asn Leu Ile Thr Arg Gln Arg Tyr
             20                  25                  30

<210> SEQ ID NO 29
<211> LENGTH: 29
<212> TYPE: PRT
<213> ORGANISM: Homo sapiens

<400> SEQUENCE: 29

Pro Gly Glu Asp Ala Pro Ala Glu Asp Met Ala Arg Tyr Tyr Ser Ala
 1               5                  10                  15

Leu Arg His Tyr Ile Asn Leu Ile Thr Arg Gln Arg Tyr
             20                  25

<210> SEQ ID NO 30
<211> LENGTH: 28
<212> TYPE: PRT
<213> ORGANISM: Homo sapiens

<400> SEQUENCE: 30
```

-continued

Gly Glu Asp Ala Pro Ala Glu Asp Met Ala Arg Tyr Tyr Ser Ala Leu
1               5                   10                  15

Arg His Tyr Ile Asn Leu Ile Thr Arg Gln Arg Tyr
            20                  25

<210> SEQ ID NO 31
<211> LENGTH: 27
<212> TYPE: PRT
<213> ORGANISM: Homo sapiens

<400> SEQUENCE: 31

Glu Asp Ala Pro Ala Glu Asp Met Ala Arg Tyr Tyr Ser Ala Leu Arg
1               5                   10                  15

His Tyr Ile Asn Leu Ile Thr Arg Gln Arg Tyr
            20                  25

<210> SEQ ID NO 32
<211> LENGTH: 26
<212> TYPE: PRT
<213> ORGANISM: Homo sapiens

<400> SEQUENCE: 32

Asp Ala Pro Ala Glu Asp Met Ala Arg Tyr Tyr Ser Ala Leu Arg His
1               5                   10                  15

Tyr Ile Asn Leu Ile Thr Arg Gln Arg Tyr
            20                  25

<210> SEQ ID NO 33
<211> LENGTH: 25
<212> TYPE: PRT
<213> ORGANISM: Homo sapiens

<400> SEQUENCE: 33

Ala Pro Ala Glu Asp Met Ala Arg Tyr Tyr Ser Ala Leu Arg His Tyr
1               5                   10                  15

Ile Asn Leu Ile Thr Arg Gln Arg Tyr
            20                  25

<210> SEQ ID NO 34
<211> LENGTH: 24
<212> TYPE: PRT
<213> ORGANISM: Homo sapiens

<400> SEQUENCE: 34

Pro Ala Glu Asp Met Ala Arg Tyr Tyr Ser Ala Leu Arg His Tyr Ile
1               5                   10                  15

Asn Leu Ile Thr Arg Gln Arg Tyr
            20

<210> SEQ ID NO 35
<211> LENGTH: 23
<212> TYPE: PRT
<213> ORGANISM: Homo sapiens

<400> SEQUENCE: 35

Ala Glu Asp Met Ala Arg Tyr Tyr Ser Ala Leu Arg His Tyr Ile Asn
1               5                   10                  15

Leu Ile Thr Arg Gln Arg Tyr
            20

<210> SEQ ID NO 36
<211> LENGTH: 22

<212> TYPE: PRT
<213> ORGANISM: Homo sapiens

<400> SEQUENCE: 36

Glu Asp Met Ala Arg Tyr Tyr Ser Ala Leu Arg His Tyr Ile Asn Leu
1               5                   10                  15

Ile Thr Arg Gln Arg Tyr
            20

<210> SEQ ID NO 37
<211> LENGTH: 21
<212> TYPE: PRT
<213> ORGANISM: Homo sapiens

<400> SEQUENCE: 37

Asp Met Ala Arg Tyr Tyr Ser Ala Leu Arg His Tyr Ile Asn Leu Ile
1               5                   10                  15

Thr Arg Gln Arg Tyr
            20

<210> SEQ ID NO 38
<211> LENGTH: 20
<212> TYPE: PRT
<213> ORGANISM: Homo sapiens

<400> SEQUENCE: 38

Met Ala Arg Tyr Tyr Ser Ala Leu Arg His Tyr Ile Asn Leu Ile Thr
1               5                   10                  15

Arg Gln Arg Tyr
            20

<210> SEQ ID NO 39
<211> LENGTH: 19
<212> TYPE: PRT
<213> ORGANISM: Homo sapiens

<400> SEQUENCE: 39

Ala Arg Tyr Tyr Ser Ala Leu Arg His Tyr Ile Asn Leu Ile Thr Arg
1               5                   10                  15

Gln Arg Tyr

<210> SEQ ID NO 40
<211> LENGTH: 18
<212> TYPE: PRT
<213> ORGANISM: Homo sapiens

<400> SEQUENCE: 40

Arg Tyr Tyr Ser Ala Leu Arg His Tyr Ile Asn Leu Ile Thr Arg Gln
1               5                   10                  15

Arg Tyr

<210> SEQ ID NO 41
<211> LENGTH: 17
<212> TYPE: PRT
<213> ORGANISM: Homo sapiens

<400> SEQUENCE: 41

Tyr Tyr Ser Ala Leu Arg His Tyr Ile Asn Leu Ile Thr Arg Gln Arg
1               5                   10                  15

Tyr

```
<210> SEQ ID NO 42
<211> LENGTH: 16
<212> TYPE: PRT
<213> ORGANISM: Homo sapiens

<400> SEQUENCE: 42

Tyr Ser Ala Leu Arg His Tyr Ile Asn Leu Ile Thr Arg Gln Arg Tyr
 1               5                  10                  15

<210> SEQ ID NO 43
<211> LENGTH: 15
<212> TYPE: PRT
<213> ORGANISM: Homo sapiens

<400> SEQUENCE: 43

Ser Ala Leu Arg His Tyr Ile Asn Leu Ile Thr Arg Gln Arg Tyr
 1               5                  10                  15

<210> SEQ ID NO 44
<211> LENGTH: 14
<212> TYPE: PRT
<213> ORGANISM: Homo sapiens

<400> SEQUENCE: 44

Ala Leu Arg His Tyr Ile Asn Leu Ile Thr Arg Gln Arg Tyr
 1               5                  10

<210> SEQ ID NO 45
<211> LENGTH: 13
<212> TYPE: PRT
<213> ORGANISM: Homo sapiens

<400> SEQUENCE: 45

Leu Arg His Tyr Ile Asn Leu Ile Thr Arg Gln Arg Tyr
 1               5                  10

<210> SEQ ID NO 46
<211> LENGTH: 12
<212> TYPE: PRT
<213> ORGANISM: Homo sapiens

<400> SEQUENCE: 46

Arg His Tyr Ile Asn Leu Ile Thr Arg Gln Arg Tyr
 1               5                  10

<210> SEQ ID NO 47
<211> LENGTH: 36
<212> TYPE: PRT
<213> ORGANISM: Homo sapiens

<400> SEQUENCE: 47

Ala Ser Leu Glu Pro Glu Tyr Pro Gly Asp Asn Ala Thr Pro Glu Gln
 1               5                  10                  15

Met Ala Gln Tyr Ala Ala Glu Leu Arg Arg Tyr Ile Asn Met Leu Thr
                20                  25                  30

Arg Pro Arg Tyr
        35

<210> SEQ ID NO 48
<211> LENGTH: 11
<212> TYPE: PRT
<213> ORGANISM: Homo sapiens

<400> SEQUENCE: 48
```

```
Arg Tyr Ile Asn Met Leu Thr Arg Pro Arg Tyr
 1               5                  10
```

<210> SEQ ID NO 49
<211> LENGTH: 34
<212> TYPE: PRT
<213> ORGANISM: Homo sapiens

<400> SEQUENCE: 49

```
Leu Glu Pro Glu Tyr Pro Gly Asp Asn Ala Thr Pro Glu Gln Met Ala
 1               5                  10                  15

Gln Tyr Ala Ala Glu Leu Arg Arg Tyr Ile Asn Met Leu Thr Arg Pro
             20                  25                  30

Arg Tyr
```

<210> SEQ ID NO 50
<211> LENGTH: 33
<212> TYPE: PRT
<213> ORGANISM: Homo sapiens

<400> SEQUENCE: 50

```
Glu Pro Glu Tyr Pro Gly Asp Asn Ala Thr Pro Glu Gln Met Ala Gln
 1               5                  10                  15

Tyr Ala Ala Glu Leu Arg Arg Tyr Ile Asn Met Leu Thr Arg Pro Arg
             20                  25                  30

Tyr
```

<210> SEQ ID NO 51
<211> LENGTH: 32
<212> TYPE: PRT
<213> ORGANISM: Homo sapiens

<400> SEQUENCE: 51

```
Pro Glu Tyr Pro Gly Asp Asn Ala Thr Pro Glu Gln Met Ala Gln Tyr
 1               5                  10                  15

Ala Ala Glu Leu Arg Arg Tyr Ile Asn Met Leu Thr Arg Pro Arg Tyr
             20                  25                  30
```

<210> SEQ ID NO 52
<211> LENGTH: 31
<212> TYPE: PRT
<213> ORGANISM: Homo sapiens

<400> SEQUENCE: 52

```
Glu Tyr Pro Gly Asp Asn Ala Thr Pro Glu Gln Met Ala Gln Tyr Ala
 1               5                  10                  15

Ala Glu Leu Arg Arg Tyr Ile Asn Met Leu Thr Arg Pro Arg Tyr
             20                  25                  30
```

<210> SEQ ID NO 53
<211> LENGTH: 30
<212> TYPE: PRT
<213> ORGANISM: Homo sapiens

<400> SEQUENCE: 53

```
Tyr Pro Gly Asp Asn Ala Thr Pro Glu Gln Met Ala Gln Tyr Ala Ala
 1               5                  10                  15

Glu Leu Arg Arg Tyr Ile Asn Met Leu Thr Arg Pro Arg Tyr
             20                  25                  30
```

<210> SEQ ID NO 54

-continued

<211> LENGTH: 29
<212> TYPE: PRT
<213> ORGANISM: Homo sapiens

<400> SEQUENCE: 54

Pro Gly Asp Asn Ala Thr Pro Glu Gln Met Ala Gln Tyr Ala Ala Glu
1               5                   10                  15

Leu Arg Arg Tyr Ile Asn Met Leu Thr Arg Pro Arg Tyr
            20                  25

<210> SEQ ID NO 55
<211> LENGTH: 28
<212> TYPE: PRT
<213> ORGANISM: Homo sapiens

<400> SEQUENCE: 55

Gly Asp Asn Ala Thr Pro Glu Gln Met Ala Gln Tyr Ala Ala Glu Leu
1               5                   10                  15

Arg Arg Tyr Ile Asn Met Leu Thr Arg Pro Arg Tyr
            20                  25

<210> SEQ ID NO 56
<211> LENGTH: 27
<212> TYPE: PRT
<213> ORGANISM: Homo sapiens

<400> SEQUENCE: 56

Asp Asn Ala Thr Pro Glu Gln Met Ala Gln Tyr Ala Ala Glu Leu Arg
1               5                   10                  15

Arg Tyr Ile Asn Met Leu Thr Arg Pro Arg Tyr
            20                  25

<210> SEQ ID NO 57
<211> LENGTH: 26
<212> TYPE: PRT
<213> ORGANISM: Homo sapiens

<400> SEQUENCE: 57

Asn Ala Thr Pro Glu Gln Met Ala Gln Tyr Ala Ala Glu Leu Arg Arg
1               5                   10                  15

Tyr Ile Asn Met Leu Thr Arg Pro Arg Tyr
            20                  25

<210> SEQ ID NO 58
<211> LENGTH: 25
<212> TYPE: PRT
<213> ORGANISM: Homo sapiens

<400> SEQUENCE: 58

Ala Thr Pro Glu Gln Met Ala Gln Tyr Ala Ala Glu Leu Arg Arg Tyr
1               5                   10                  15

Ile Asn Met Leu Thr Arg Pro Arg Tyr
            20                  25

<210> SEQ ID NO 59
<211> LENGTH: 24
<212> TYPE: PRT
<213> ORGANISM: Homo sapiens

<400> SEQUENCE: 59

Thr Pro Glu Gln Met Ala Gln Tyr Ala Ala Glu Leu Arg Arg Tyr Ile
1               5                   10                  15

Asn Met Leu Thr Arg Pro Arg Tyr
            20

<210> SEQ ID NO 60
<211> LENGTH: 23
<212> TYPE: PRT
<213> ORGANISM: Homo sapiens

<400> SEQUENCE: 60

Pro Gln Met Ala Gln Tyr Ala Ala Glu Leu Arg Arg Tyr Ile Asn
1               5                   10                  15

Met Leu Thr Arg Pro Arg Tyr
            20

<210> SEQ ID NO 61
<211> LENGTH: 22
<212> TYPE: PRT
<213> ORGANISM: Homo sapiens

<400> SEQUENCE: 61

Glu Gln Met Ala Gln Tyr Ala Ala Glu Leu Arg Arg Tyr Ile Asn Met
1               5                   10                  15

Leu Thr Arg Pro Arg Tyr
            20

<210> SEQ ID NO 62
<211> LENGTH: 21
<212> TYPE: PRT
<213> ORGANISM: Homo sapiens

<400> SEQUENCE: 62

Gln Met Ala Gln Tyr Ala Ala Glu Leu Arg Arg Tyr Ile Asn Met Leu
1               5                   10                  15

Thr Arg Pro Arg Tyr
            20

<210> SEQ ID NO 63
<211> LENGTH: 20
<212> TYPE: PRT
<213> ORGANISM: Homo sapiens

<400> SEQUENCE: 63

Met Ala Gln Tyr Ala Ala Glu Leu Arg Arg Tyr Ile Asn Met Leu Thr
1               5                   10                  15

Arg Pro Arg Tyr
            20

<210> SEQ ID NO 64
<211> LENGTH: 19
<212> TYPE: PRT
<213> ORGANISM: Homo sapiens

<400> SEQUENCE: 64

Ala Gln Tyr Ala Ala Glu Leu Arg Arg Tyr Ile Asn Met Leu Thr Arg
1               5                   10                  15

Pro Arg Tyr

<210> SEQ ID NO 65
<211> LENGTH: 18
<212> TYPE: PRT
<213> ORGANISM: Homo sapiens

<400> SEQUENCE: 65

-continued

Gln Tyr Ala Ala Glu Leu Arg Arg Tyr Ile Asn Met Leu Thr Arg Pro
1               5                   10                  15
Arg Tyr

<210> SEQ ID NO 66
<211> LENGTH: 17
<212> TYPE: PRT
<213> ORGANISM: Homo sapiens

<400> SEQUENCE: 66

Tyr Ala Ala Glu Leu Arg Arg Tyr Ile Asn Met Leu Thr Arg Pro Arg
1               5                   10                  15
Tyr

<210> SEQ ID NO 67
<211> LENGTH: 16
<212> TYPE: PRT
<213> ORGANISM: Homo sapiens

<400> SEQUENCE: 67

Ala Ala Glu Leu Arg Arg Tyr Ile Asn Met Leu Thr Arg Pro Arg Tyr
1               5                   10                  15

<210> SEQ ID NO 68
<211> LENGTH: 15
<212> TYPE: PRT
<213> ORGANISM: Homo sapiens

<400> SEQUENCE: 68

Ala Glu Leu Arg Arg Tyr Ile Asn Met Leu Thr Arg Pro Arg Tyr
1               5                   10                  15

<210> SEQ ID NO 69
<211> LENGTH: 14
<212> TYPE: PRT
<213> ORGANISM: Homo sapiens

<400> SEQUENCE: 69

Glu Leu Arg Arg Tyr Ile Asn Met Leu Thr Arg Pro Arg Tyr
1               5                   10

<210> SEQ ID NO 70
<211> LENGTH: 13
<212> TYPE: PRT
<213> ORGANISM: Homo sapiens

<400> SEQUENCE: 70

Leu Arg Arg Tyr Ile Asn Met Leu Thr Arg Pro Arg Tyr
1               5                   10

<210> SEQ ID NO 71
<211> LENGTH: 12
<212> TYPE: PRT
<213> ORGANISM: Homo sapiens

<400> SEQUENCE: 71

Arg Arg Tyr Ile Asn Met Leu Thr Arg Pro Arg Tyr
1               5                   10

<210> SEQ ID NO 72
<211> LENGTH: 36
<212> TYPE: PRT
<213> ORGANISM: Rat

```
<400> SEQUENCE: 72

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
            35

<210> SEQ ID NO 73
<211> LENGTH: 36
<212> TYPE: PRT
<213> ORGANISM: Pig

<400> SEQUENCE: 73

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
            35

<210> SEQ ID NO 74
<211> LENGTH: 36
<212> TYPE: PRT
<213> ORGANISM: Guinea pig

<400> SEQUENCE: 74

Tyr Pro Ser Lys Pro Glu Ala Pro Gly Ser Asp Ala Ser Pro Glu Glu
1               5                   10                  15

Leu Ala Arg Tyr Tyr Ala Ser Leu Arg His Tyr Leu Asn Leu Val Thr
            20                  25                  30

Arg Gln Arg Tyr
            35

<210> SEQ ID NO 75
<211> LENGTH: 36
<212> TYPE: PRT
<213> ORGANISM: Rat

<400> SEQUENCE: 75

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35

<210> SEQ ID NO 76
<211> LENGTH: 36
<212> TYPE: PRT
<213> ORGANISM: Rabbit

<400> SEQUENCE: 76

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
            35
```

<210> SEQ ID NO 77
<211> LENGTH: 36
<212> TYPE: PRT
<213> ORGANISM: Dog

<400> SEQUENCE: 77

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 78
<211> LENGTH: 36
<212> TYPE: PRT
<213> ORGANISM: Pig

<400> SEQUENCE: 78

Tyr Pro Ser Lys Pro Asp Asn Pro Gly Glu Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
        35

<210> SEQ ID NO 79
<211> LENGTH: 36
<212> TYPE: PRT
<213> ORGANISM: Cow

<400> SEQUENCE: 79

Tyr Pro Ser Lys Pro Asp Asn Pro Gly Glu Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
        35

<210> SEQ ID NO 80
<211> LENGTH: 36
<212> TYPE: PRT
<213> ORGANISM: Sheep

<400> SEQUENCE: 80

Tyr Pro Ser Lys Pro Asp Asn Pro Gly Asp Asp Ala Pro Ala Glu Asp
1               5                   10                  15

Leu Ala Arg Tyr Tyr Ser Ala Leu Arg His Tyr Ile Asn Leu Ile Thr
            20                  25                  30

Arg Gln Arg Tyr
        35

<210> SEQ ID NO 81
<211> LENGTH: 36
<212> TYPE: PRT
<213> ORGANISM: Guinea pig

<400> SEQUENCE: 81

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 82
<211> LENGTH: 36
<212> TYPE: PRT
<213> ORGANISM: Sheep

<400> SEQUENCE: 82

Ala Pro Leu Glu Pro Val Tyr Pro Gly Asp Asn Ala Thr Pro Glu Gln
 1               5                  10                  15

Met Ala Gln Tyr Ala Ala Asp Leu Arg Arg Tyr Ile Asn Met Leu Thr
            20                  25                  30

Arg Pro Arg Tyr
        35

<210> SEQ ID NO 83
<211> LENGTH: 36
<212> TYPE: PRT
<213> ORGANISM: Pig

<400> SEQUENCE: 83

Ala Pro Leu Glu Pro Val Tyr Pro Gly Asp Asp Ala Thr Pro Glu Gln
 1               5                  10                  15

Met Ala Gln Tyr Ala Ala Glu Leu Arg Arg Tyr Ile Asn Met Leu Thr
            20                  25                  30

Arg Pro Arg Tyr
        35

<210> SEQ ID NO 84
<211> LENGTH: 36
<212> TYPE: PRT
<213> ORGANISM: Dog

<400> SEQUENCE: 84

Ala Pro Leu Glu Pro Val Tyr Pro Gly Asp Asp Ala Thr Pro Glu Gln
 1               5                  10                  15

Met Ala Gln Tyr Ala Ala Glu Leu Arg Arg Tyr Ile Asn Met Leu Thr
            20                  25                  30

Arg Pro Arg Tyr
        35

<210> SEQ ID NO 85
<211> LENGTH: 36
<212> TYPE: PRT
<213> ORGANISM: Cat

<400> SEQUENCE: 85

Ala Pro Leu Glu Pro Val Tyr Pro Gly Asp Asn Ala Thr Pro Glu Gln
 1               5                  10                  15

Met Ala Gln Tyr Ala Ala Glu Leu Arg Arg Tyr Ile Asn Met Leu Thr
            20                  25                  30

Arg Pro Arg Tyr
        35

<210> SEQ ID NO 86
<211> LENGTH: 36
<212> TYPE: PRT

```
<213> ORGANISM: Cow

<400> SEQUENCE: 86

Ala Pro Leu Glu Pro Glu Tyr Pro Gly Asp Ala Thr Pro Glu Gln
 1               5                  10                  15

Met Ala Gln Tyr Ala Ala Glu Leu Arg Arg Tyr Ile Asn Met Leu Thr
            20                  25                  30

Arg Pro Arg Tyr
        35

<210> SEQ ID NO 87
<211> LENGTH: 36
<212> TYPE: PRT
<213> ORGANISM: Rat

<400> SEQUENCE: 87

Ala Pro Leu Glu Pro Met Tyr Pro Gly Asp Tyr Ala Thr His Glu Gln
 1               5                  10                  15

Arg Ala Gln Tyr Glu Thr Gln Leu Arg Arg Tyr Ile Asn Thr Leu Thr
            20                  25                  30

Arg Pro Arg Tyr
        35

<210> SEQ ID NO 88
<211> LENGTH: 36
<212> TYPE: PRT
<213> ORGANISM: mouse

<400> SEQUENCE: 88

Ala Pro Leu Glu Pro Met Tyr Pro Gly Asp Tyr Ala Thr Pro Glu Gln
 1               5                  10                  15

Met Ala Gln Tyr Glu Thr Gln Leu Arg Arg Tyr Ile Asn Thr Leu Thr
            20                  25                  30

Arg Pro Arg Tyr
        35

<210> SEQ ID NO 89
<211> LENGTH: 37
<212> TYPE: PRT
<213> ORGANISM: Guinea pig

<400> SEQUENCE: 89

Ala Pro Leu Glu Pro Val Tyr Pro Gly Asp Asn Ala Thr Pro Glu Gln
 1               5                  10                  15

Gln Met Ala Gln Tyr Ala Ala Glu Met Arg Arg Tyr Ile Asn Met Leu
            20                  25                  30

Thr Arg Pro Arg Tyr
        35

<210> SEQ ID NO 90
<211> LENGTH: 22
<212> TYPE: PRT
<213> ORGANISM: Homo sapiens

<400> SEQUENCE: 90

Asp Glu Leu Asn Arg Tyr Tyr Ala Ser Leu Arg His Tyr Leu Asn Leu
 1               5                  10                  15

Val Thr Arg Gln Arg Tyr
            20
```

<210> SEQ ID NO 91
<211> LENGTH: 24
<212> TYPE: PRT
<213> ORGANISM: Homo sapiens

<400> SEQUENCE: 91

Thr Pro Glu Glu Leu Asn Arg Tyr Tyr Ala Ser Leu Arg His Tyr Leu
1               5                   10                  15

Asn Leu Val Thr Arg Gln Arg Tyr
            20

<210> SEQ ID NO 92
<211> LENGTH: 25
<212> TYPE: PRT
<213> ORGANISM: Homo sapiens

<400> SEQUENCE: 92

Val Ser Pro Glu Glu Leu Asn Arg Tyr Tyr Ala Ser Leu Arg His Tyr
1               5                   10                  15

Leu Asn Leu Val Thr Arg Gln Arg Tyr
            20                  25

<210> SEQ ID NO 93
<211> LENGTH: 26
<212> TYPE: PRT
<213> ORGANISM: Homo sapiens

<400> SEQUENCE: 93

Glu Ala Ser Pro Glu Glu Leu Asn Arg Tyr Tyr Ala Ser Leu Arg His
1               5                   10                  15

Tyr Leu Asn Leu Val Thr Arg Gln Arg Tyr
            20                  25

<210> SEQ ID NO 94
<211> LENGTH: 27
<212> TYPE: PRT
<213> ORGANISM: Homo sapiens

<400> SEQUENCE: 94

Asp Asp Ala Ser Pro Glu Glu Leu Asn Arg Tyr Tyr Ala Ser Leu Arg
1               5                   10                  15

His Tyr Leu Asn Leu Val Thr Arg Gln Arg Tyr
            20                  25

<210> SEQ ID NO 95
<211> LENGTH: 30
<212> TYPE: PRT
<213> ORGANISM: Homo sapiens

<400> SEQUENCE: 95

Val Pro Gly Glu Asp Ala Ser Pro Glu Glu Leu Asn Arg Tyr Tyr Ala
1               5                   10                  15

Ser Leu Arg His Tyr Leu Asn Leu Val Thr Arg Gln Arg Tyr
            20                  25                  30

<210> SEQ ID NO 96
<211> LENGTH: 31
<212> TYPE: PRT
<213> ORGANISM: Homo sapiens

<400> SEQUENCE: 96

Asp Ala Pro Gly Glu Asp Ala Ser Pro Glu Glu Leu Asn Arg Tyr Tyr
1               5                   10                  15

```
Ala Ser Leu Arg His Tyr Leu Asn Leu Val Thr Arg Gln Arg Tyr
            20                  25                  30

<210> SEQ ID NO 97
<211> LENGTH: 33
<212> TYPE: PRT
<213> ORGANISM: Homo sapiens

<400> SEQUENCE: 97

Gln Pro Glu Ala Pro Gly Glu Asp Ala Ser Pro Glu Leu Asn Arg
 1               5                  10                  15

Tyr Tyr Ala Ser Leu Arg His Tyr Leu Asn Leu Val Thr Arg Gln Arg
            20                  25                  30

Tyr

<210> SEQ ID NO 98
<211> LENGTH: 33
<212> TYPE: PRT
<213> ORGANISM: Homo sapiens

<400> SEQUENCE: 98

Arg Pro Glu Ala Pro Gly Glu Asp Ala Ser Pro Glu Leu Asn Arg
 1               5                  10                  15

Tyr Tyr Ala Ser Leu Arg His Tyr Leu Asn Leu Val Thr Arg Gln Arg
            20                  25                  30

Tyr

<210> SEQ ID NO 99
<211> LENGTH: 33
<212> TYPE: PRT
<213> ORGANISM: Homo sapiens

<400> SEQUENCE: 99

Asn Pro Glu Ala Pro Gly Glu Asp Ala Ser Pro Glu Leu Asn Arg
 1               5                  10                  15

Tyr Tyr Ala Ser Leu Arg His Tyr Leu Asn Leu Val Thr Arg Gln Arg
            20                  25                  30

Tyr

<210> SEQ ID NO 100
<211> LENGTH: 34
<212> TYPE: PRT
<213> ORGANISM: Homo sapiens

<400> SEQUENCE: 100

Val Lys Pro Glu Ala Pro Gly Glu Asp Ala Ser Pro Glu Leu Asn
 1               5                  10                  15

Arg Tyr Tyr Ala Ser Leu Arg His Tyr Leu Asn Leu Val Thr Arg Gln
            20                  25                  30

Arg Tyr

<210> SEQ ID NO 101
<211> LENGTH: 34
<212> TYPE: PRT
<213> ORGANISM: Homo sapiens

<400> SEQUENCE: 101

Leu Lys Pro Glu Ala Pro Gly Glu Asp Ala Ser Pro Glu Leu Asn
 1               5                  10                  15
```

```
Arg Tyr Tyr Ala Ser Leu Arg His Tyr Leu Asn Leu Val Thr Arg Gln
            20                  25                  30

Arg Tyr

<210> SEQ ID NO 102
<211> LENGTH: 27
<212> TYPE: PRT
<213> ORGANISM: Homo sapiens

<400> SEQUENCE: 102

Asp Asp Ala Ser Pro Asp Glu Leu Asn Arg Tyr Tyr Ala Ser Leu Arg
 1               5                  10                  15

His Tyr Leu Asn Leu Val Thr Arg Gln Arg Tyr
            20                  25

<210> SEQ ID NO 103
<211> LENGTH: 31
<212> TYPE: PRT
<213> ORGANISM: Homo sapiens

<400> SEQUENCE: 103

Asp Ala Pro Gly Glu Asp Ala Thr Pro Glu Glu Leu Asn Arg Tyr Tyr
 1               5                  10                  15

Ala Ser Leu Arg His Tyr Leu Asn Leu Val Thr Arg Gln Arg Tyr
            20                  25                  30

<210> SEQ ID NO 104
<211> LENGTH: 33
<212> TYPE: PRT
<213> ORGANISM: Homo sapiens

<400> SEQUENCE: 104

Asn Pro Glu Ala Pro Gly Glu Asp Ala Ser Pro Asp Glu Leu Asn Arg
 1               5                  10                  15

Tyr Tyr Ala Ser Leu Arg His Tyr Leu Asn Leu Val Thr Arg Gln Arg
            20                  25                  30

Tyr

<210> SEQ ID NO 105
<211> LENGTH: 34
<212> TYPE: PRT
<213> ORGANISM: Homo sapeins

<400> SEQUENCE: 105

Leu Lys Pro Glu Ala Pro Gly Asp Asp Ala Ser Pro Glu Glu Leu Asn
 1               5                  10                  15

Arg Tyr Tyr Ala Ser Leu Arg His Tyr Leu Asn Leu Val Thr Arg Gln
            20                  25                  30

Arg Tyr
```